(12) United States Patent
Wells et al.

(10) Patent No.: US 6,780,613 B1
(45) Date of Patent: Aug. 24, 2004

(54) GROWTH HORMONE VARIANTS

(75) Inventors: James A. Wells, Burlingame, CA (US); Brian C. Cunningham, Piedmont, CA (US)

(73) Assignee: Genentech, Inc., South San Francisco, CA (US)

(*) Notice: Subject to any disclaimer, the term of this patent is extended or adjusted under 35 U.S.C. 154(b) by 1826 days.

(21) Appl. No.: 08/479,884

(22) Filed: Jun. 7, 1995

Related U.S. Application Data

(60) Division of application No. 08/190,723, filed on Feb. 2, 1994, which is a continuation of application No. 07/960,227, filed on Oct. 13, 1992, now abandoned, which is a continuation of application No. 07/875,204, filed on Apr. 27, 1992, now abandoned, which is a continuation of application No. 07/428,066, filed on Oct. 26, 1989, now abandoned, which is a continuation-in-part of application No. 07/264,611, filed on Oct. 28, 1988, now abandoned.

(51) Int. Cl.$^7$ .......................... C12N 1/21; C12N 15/18; C12N 15/63; C07K 14/61
(52) U.S. Cl. .................. 435/69.4; 435/243; 435/320.1; 435/325; 530/399; 536/23.51
(58) Field of Search .................... 536/23.51; 435/252.3, 435/240.2, 320.1, 69.4; 530/399

(56) References Cited

U.S. PATENT DOCUMENTS

| | | | |
|---|---|---|---|
| 4,446,235 A | 5/1984 | Seeburg | 435/91 |
| 4,665,160 A | 5/1987 | Seeburg | 530/399 |
| 4,670,393 A | 6/1987 | Seeburg | 435/240 |
| 4,699,897 A | 10/1987 | Jones et al. | 514/4 |
| 4,732,973 A | 3/1988 | Borr et al. | 530/350 |
| 4,871,835 A | * 10/1989 | Aviv et al. | 530/399 |
| 4,888,286 A | 12/1989 | Crea | 435/172.3 |
| 5,085,862 A | 2/1992 | Klein et al. | 424/92 |
| 5,204,244 A | 4/1993 | Fell et al. | 435/69.6 |
| 5,350,836 A | 9/1994 | Kopchick et al. | 530/399 |
| 5,681,809 A | * 10/1997 | Kopchick et al. | 514/2 |
| 6,238,915 B1 | 5/2001 | Chihara | |

FOREIGN PATENT DOCUMENTS

| | | |
|---|---|---|
| EP | 0 089 666 A | 9/1983 |
| EP | 8807578 | 6/1988 |
| EP | 0 320 308 A2 | 6/1989 |
| WO | WO 88/07084 | 9/1988 |
| WO | WO 88/07578 | 10/1988 |

OTHER PUBLICATIONS

Nicoll et al. Endocrine Reviews (1986) 7, 169–203.*
Rudinger et al. Peptide Hormones, University Park Press, Baltimore, pp. 1–7, 1976.*
Abdel–Maeguid, S. S. et al., "Three–dimensional structure of a genetically engineered variant of porcine growth hormone", 84 *Proc. Natl. Acad. Sci. USA* 6434–6437 (1987).
Bajt et al., Characterization of a Gain of Function Mutation of Integrin αIIβ3 (Platelet Glycoprotein IIb–IIIa), 267 *J. Biol. Chem.* 22211–22216 (1992).
Barlow, D. J. et al., "Continuous and discontinuous protein antigenic determinants", 322 *Nature* 747–748 (1986).
Bennett et al., "High Resolution Analysis of Functional Determinants of Human Tissue–type Plasminogen Activator", 266 *J. Biol. Chem.* 5191–5201 (1991).
Berendt et al., "The Binding Site on ICAM–1 for Plasmodium falciparum–Infected Erythrocytes Overlaps, but is Distinct LFA–1 Binding Site", 68 *Cell* 71–81 (1992).
Berlot et al., "Identification of Effector–Activating Residues of G sα", 68 *Cell* 911–922 (1992).
Bettler et al., "Immunoglobulin E–binding Site in Fc Receptor FcRII/CD23) Identified by Homolog–scanning Mutagenesis", 267 *J. Biol. Chem.* 185–191 (1992).
Boutin, J. M. et al., "Cloning and Expression of the Rat Prolactin Receptor, a Member of the Growth Hormone/ Prolactin Receptor Gene Family", 53 *Cell* 69–77 (1988).
Burstein et al., "Immunoreactivity and receptor binding of mixed recombinants of human growth hormone and chorionic somatomammotropin", 75 *Proc. Natl. Acad. Sci. USA* 5391–5394 (1978).
Camble, R. et al., "Properties of Interferon–α2 Analogues Produced from Synthetic Genes in Peptides: Strucuture and Function", *Proceedings of the Ninth American Peptide Symposium* 375–384 (Deber et al. eds. 1985).
Chang, C. N. et al., "High–level secretion of human growth hormone by *Escherichia coli*", 55 *Gene* 189–196 (1987).
Clayton et al., "Substitution of murine for human CD4 residues identifies amino acids critical for HIV–gp120 binding", 355 *Nature* 363–366 (1988).
Cunningham, B., "Improvement in the alkaline stability of subtilisin using an efficient random mutagenesis and screening procedure", 108 *Chemical Abstracts 11* (1988).

(List continued on next page.)

*Primary Examiner*—Christine J. Saoud
(74) *Attorney, Agent, or Firm*—Gates & Cooper LLP

(57) ABSTRACT

The invention provides methods for the systematic analysis of the structure and function of polypeptides by identifying active domains which influence the activity of the polypeptide with a target substance. Such active domains are determined by substituting selected amino acid segments of the polypeptide with an analogous polypeptide segment from an analog to the polypeptide. The analog has a different activity with the target substance as compared to the parent polypeptide. The activities of the segment-substituted polypeptides are compared to the same activity for the parent polypeptide for the target. A comparison of such activities provides an indication of the location of the active domain in the parent polypeptide. The invention also provides methods for identifying the active amino acid residues within the active domain of the parent polypeptide. The method comprises substituting a scanning amino acid for one of the amino acid residues within the active domain of the parent polypeptide and assaying the residue-substituted polypeptide so formed with a target substance. The invention further provides polypeptide variants comprising segment-substituted and residue-substituted growth hormones, prolactins and placental lactogens.

51 Claims, 55 Drawing Sheets

OTHER PUBLICATIONS

Cunningham, B. et al., "Receptor and Antibody Epitopes in Human Growth Hormone Identified by Homolog–Scanning Mutagenesis", 243 *Science* 1330–1336 (1989).

Cunningham, B. et al., "High–Resolution Epitope Mapping of hGH–Receptor Interactions by Alanine–Scanning Mutagenesis", 244 *Science* 1081–1085 (1989).

Ge et al., "Functional Domains of *Bacillus thuringiensis* Insecticidal Crystal Proteins", 266 *J. Biol. Chem.* 17954–17958 (1991).

Geysen et al., 81 *P.N.A.S., USA* 3998–4002 (1984).

Goeddel et al., "Direct expression in *Escherichia coli* of a DNA sequence coding for human growth hormone", 281 *Nature* 544–548 (1979).

Gray et al., "Periplasmic production of correctly processed human growth in Escherichia coli: nature and bacterial signal sequences are interchangeable", 39 *Gene* 247–254 (1985).

Hotta et al., 149 *Biochem. and Biophys. Res. Comm.* 531–537 (1987).

Huang et al., 223 *FEBS Letters* 294–298 (1987).

Jones, P. T. et al., "Replacing the complementarity–determining regions in a human antibody with those from a mouse", 321 *Nature* 522–525 (1986).

Kobilka, B. et al., "Chemeric α2–, β2–Adrenergic Receptors: Delineation of Domains Involved in Effector Coupling and Ligand Binding Specificity", 240 *Science* 1310–1316 (1988).

Kostyo, J. L. et al., "Biological characterization of purified native 20–kDa human growth hormone", 925 *Biochemica et Biohysica Acta* 314 (1987).

Krivi, G. G. et al., "Immunohistochemcial Expression of Insulin–like growth factor I during Skeletal Muscle Regeneration in Normal . . . ", Abstract I–18, *Int'l. Symp. on Growth Hormone; Basic and Clin. Aspects*, Final Program, sponsored by Serono Sympsoia, USA (Jun. 14–18, 1987).

Laskowski, M. et al., "Postivie Darwinian Selection in Evolution of Protein Inhibitors of Serine Proteinases", 52 *Cold Spring Harbor Symp. Quant. Biol.* 545 (1987).

Leung, D. W. et al., "Growth hormone receptor and serum binding protein: purification, cloning and expression", 330 *Nature* 537–543 (1987).

Lewis, U. J. et al., "A Naturally Occurring Structural Variant of Human Growth Hormone", 253 *J. Biol. Chem.* 2679–2687 (1978).

Lewis, U. J., "Variants of Growth Hormone and Prolactin and Their Posttranslational Modifications", 46 *Ann. Rev. Physiol.* 33–42 (1984).

Li, C. H., "Human growth hormone: 1974–1981", 46 *Mol. Cell. Biochem.* 31–41 (1982).

Marseigne et al., 31 *J. Med. Chem.* 966–970 (1988).

Mills, J. B. et al., "Fragments of Human Growth Hormone Produced by Digestion with Thrombin: Chemistry and Biological Properties", 107 *Endocrinology* 319–399 (1980).

Nakashima et al., "Alanine–scanning Mutagenesis of the Epidermal Growth Factor–like Domains of Human Thrombomodulin Identifies Critical Residues for Its Cofactor Activtiy", 268 *J. Biol. Chem.* 2888–2892 (1993).

Russell et al., "Recombinant Hormones from Fragments of Human Growth Hormone and Human Placental Lactogen", 256 *J. Biol. Chem.* 296–300 (1981).

Seeberg, P. H., "The Human Growth Hormone Gene Family: Nucleotide Sequences Show Recent Divergence and Predict a New Polypeptide Hormone", 1 *DNA* 239–249 (1982).

Sourouton, M. C. et al., "Localization of Highly Immunogenic Region on the Acetylcholine Receptor Alpha–Subunit", 135 *Biochem. Biophys. Res. Commun.* 82–89 (1986).

Tokunaga, T. et al., "Synthesis and expression of a human growth hormone (somatotropin) gene mutated to change cysteine–165 to alanine", 153 *Eur. J. Biochem.* 445–449 (1985).

Venuti et al., "The Impact of Biotechnology on Drug Discovery", *Ann. Reports in Medicinal Chem.* 289–298 (Vinick ed. 1989).

Wells, J., "Systematic Mutational Analysis of Protein–Protein Interfaces", 202 *Methods in Enzymology* 390–411 (1991).

Werther et al., "Localization and Characterization of Insulin Receptors in Rat Brain and Pituitary Gland Using In–Vitro Autoradiography and Computerized Densitometry", 121 *Endocrinol.* 1562–1570 (1987).

Wertman et al., "Systematic Mutational Analysis of the Yeast ACT1 Gene", 132 *Genetics* 337–350 (1992).

Wharton, R. P. et al., "Substituting and α–Helix Switches the Sequence–Specific DNA Interactions of a Repressor", 38 *Cell* 361–369 (1984).

Wharton, R. P. et al., "Changing the binding specificity of a repressor by redesigning an α–helix", 316 *Nature* 601–605 (1985).

Wharton, R. P. et al., 38 *Nature* 316–369 (1985).

Wu and Wallace, "The Ligation Amplification Reaction (LAR)—Amplification of Specific DNA Sequences Using Sequential Rounds of Template–Dependent Ligation", 4 *Genomics* 560–569 (1989).

Zhang et al., "Toward a Simplification of the Protein Folding Problem: A Stablizing Polyalanine α–Helix Ingineered in T4 Lysozyme", 30 *Biochemistry* 2012–2017 (1991).

Zoller et al., "New molecular biology methods of protein engineering", 1 *Current Opinion in Structural Biology* 605–610 (1991).

\* cited by examiner

FIG.—3

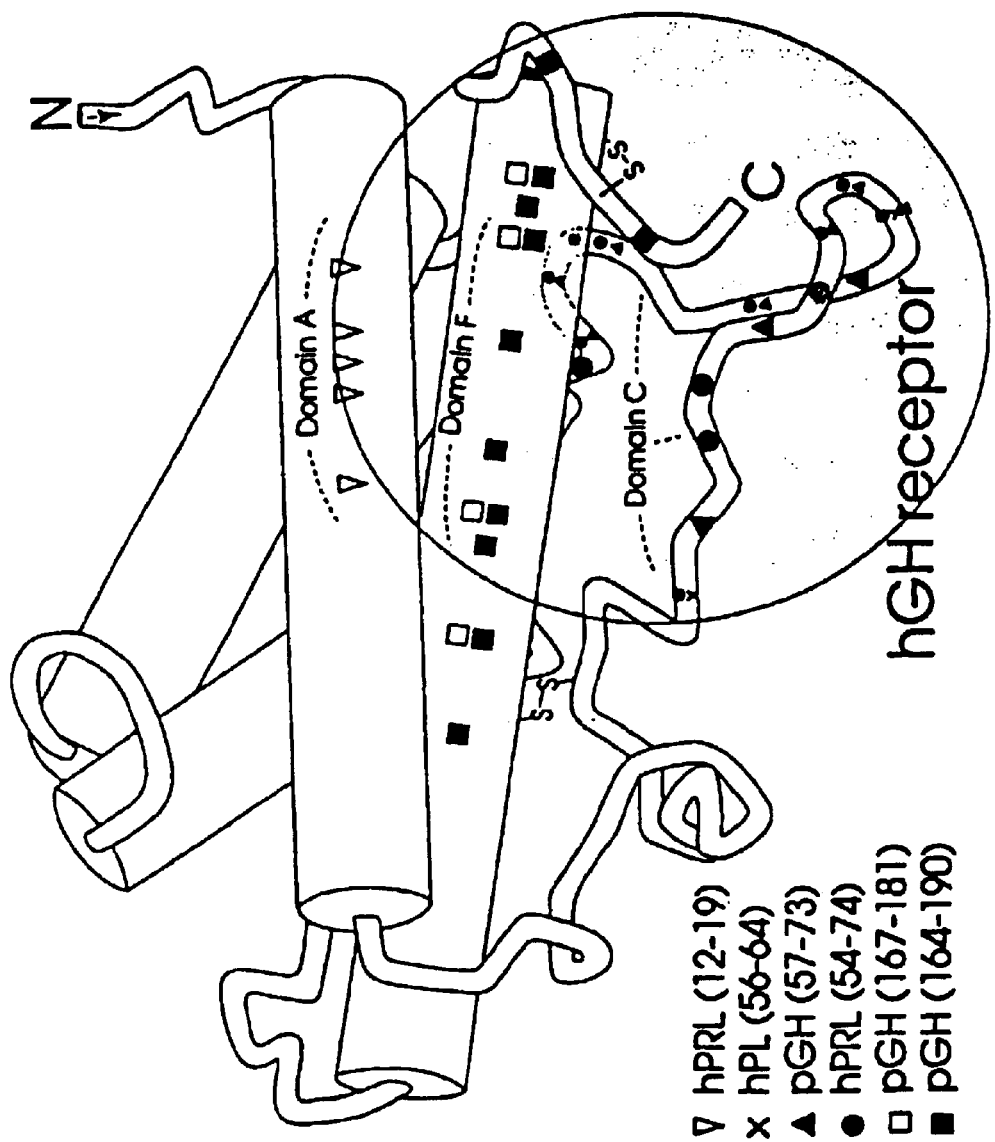
FIG.—5

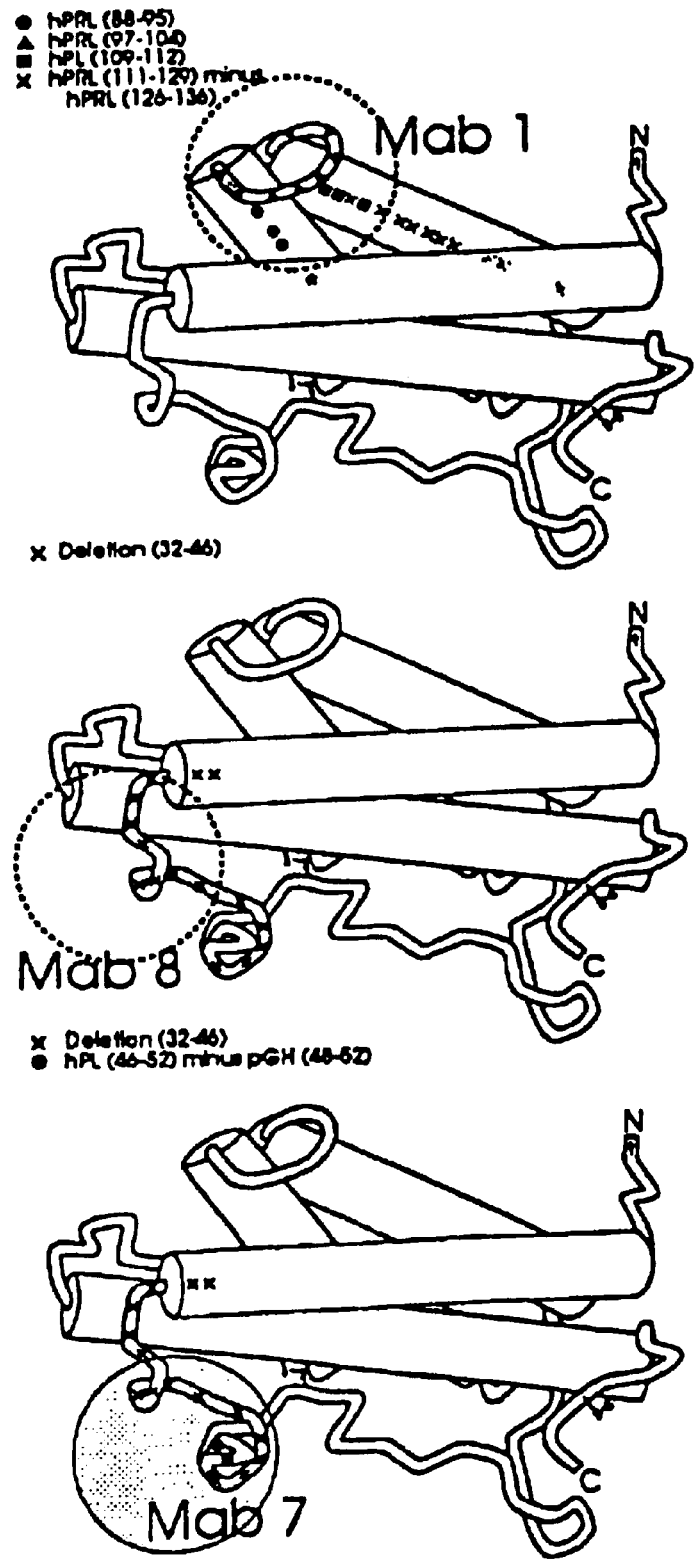
FIG.—6A

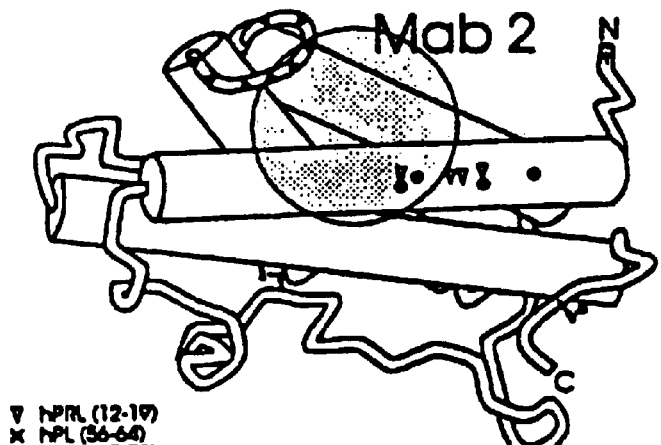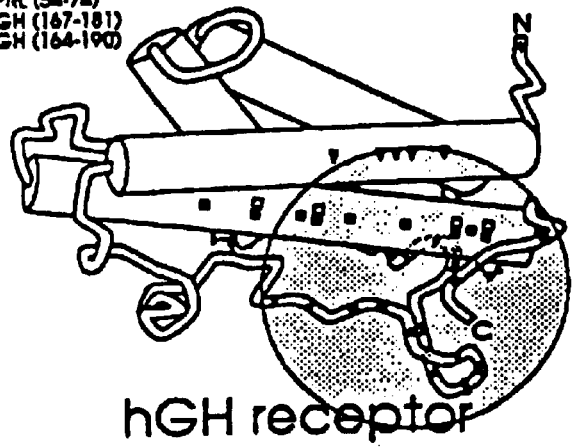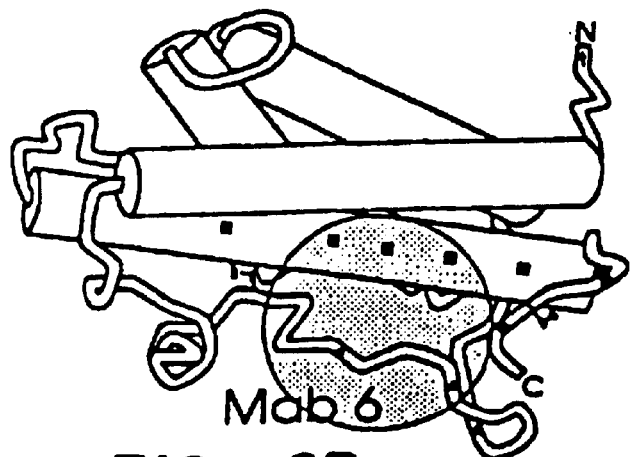
FIG.—6B

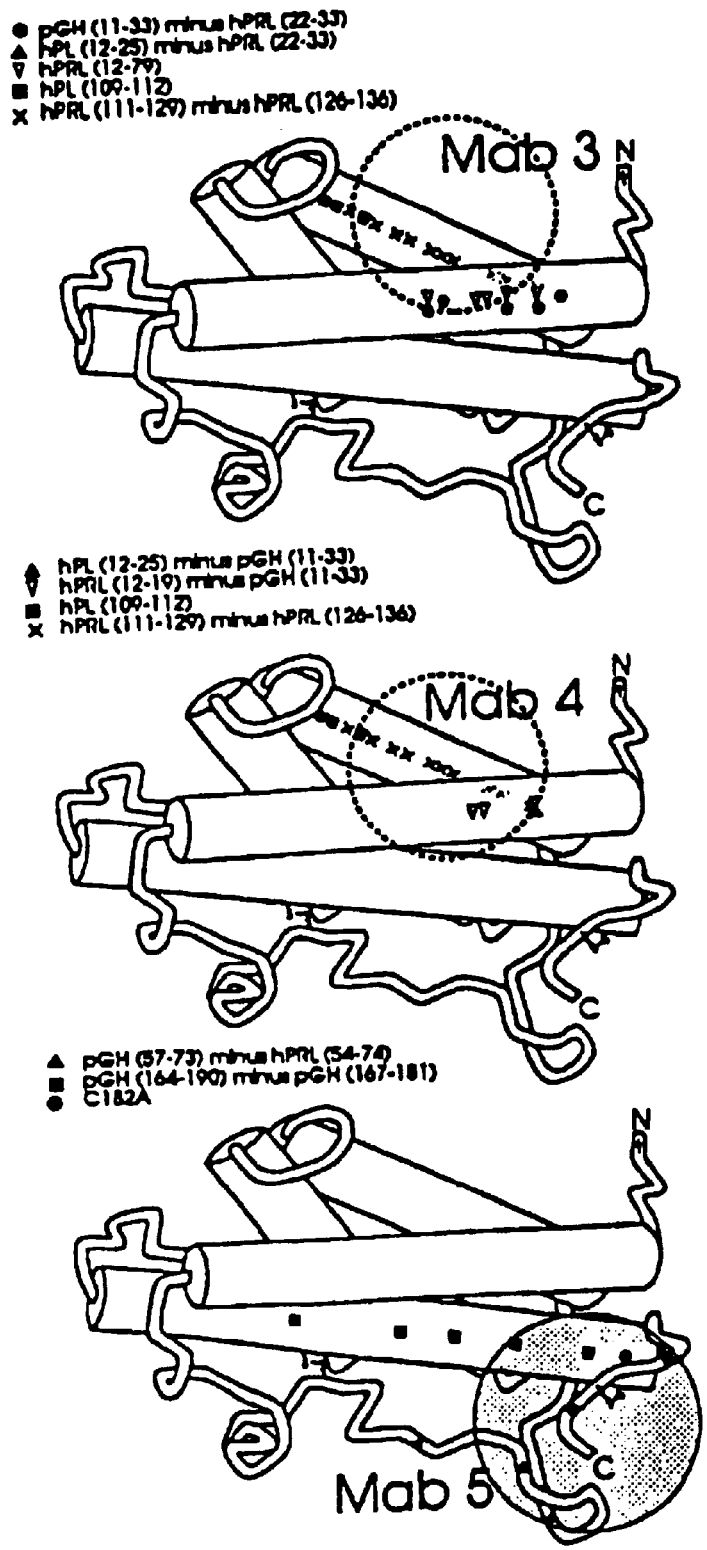
FIG.—6C

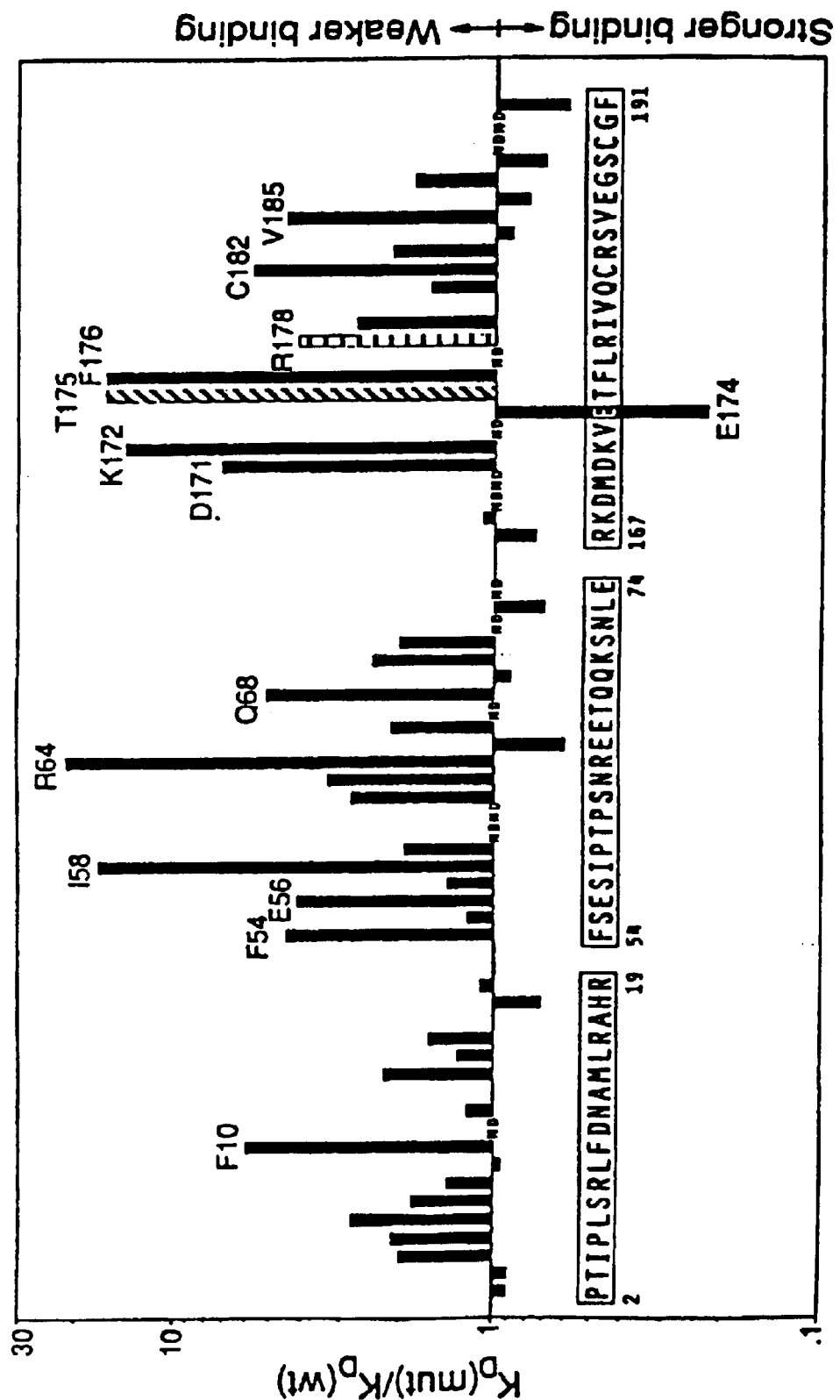
FIG.—7 hGH Synthetic Gene

```
                                         -20                                                          -10                                                     -1
     Met Lys Lys Asn Ile Ala Phe Leu Leu Ala Ser Met Phe Val Phe Ser Ile Ala Thr Asn Ala Tyr Ala
  1  ATG AAA AAG AAT ATC GCA TTT CTT CTT GCA TCT ATG TTC GTT TTT TCT ATT GCT ACA AAT GCC TAT GCA
                                                                                                                                                          NsiI

+1                                                  10                                                     20
     Phe Pro Thr Ile Pro Leu Ser Arg Leu Phe Asp Asn Ala Met Leu Arg Ala His Arg Leu His Gln Leu Ala
  79 TTC CCA ACT ATA CCA CTA AGT CGA CTA TTC GAT AAC GCT ATG CTT CGG GCC CAT CGT CTT CAT CAG CTA GCC
                                       SalI                                         ApaI                                                                   XhoI

Phe Asp Thr Tyr Gln Glu Phe Glu Glu Ala Tyr Ile Pro Lys Glu Gln Lys Tyr Ser Phe Leu Gln Asn Pro
 142 TTT GAC ACC TAC CAG GAG TTT GAA GAG GCC TAT ATC CCC AAG GAA CAG AAG TAT TCA TTC CTG CAG AAC CCC
                                                         StuI                                                                                              PstI 50                                                          60                                                     70
     Gln Thr Ser Leu Cys Phe Ser Glu Ser Ile Pro Thr Pro Ser Asn Arg Glu Glu Thr Gln Gln Lys Ser Asn
 214 CAG ACC TCC CTC TGT TTC TCA GAA TCG ATT CCG ACA CCC TCC AAT CGT GAG GAA ACA CAA CAG AAA TCC AAC
                                                    ClaI                                        MroI 80                                                         90
     Leu Glu Leu Leu Arg Ile Ser Leu Leu Leu Ile Gln Ser Trp Leu Glu Pro Val Gln Phe Leu Arg Ser Val
 286 CTA GAG CTC CTC CGC ATA AGC TTG CTC CTC ATC CAG TCG TGG CTC GAG CCC GTG CAG TTC CTG AGG AGT GTC
              SacI                       HindIII                                              XhoI                                              MstII 100                                                          110                                                  120
     Phe Ala Asn Ser Leu Val Tyr Gly Ala Ser Asp Ser Asn Val Tyr Asp Leu Leu Lys Asp Leu Glu Glu Gly
 358 TTC GCC AAC AGC CTG GTC TAC GGC GCC TCT GAT TCG AAC GTG TAC GAC CTC CTG AAG GAC CTA GAG GAA GGG
                                                                    MroI           AsuII                                                                         BamHI 130                                                  140
     Ile Gln Thr Leu Met Gly Arg Leu Glu Asp Gly Ser Pro Arg Thr Gly Gln Ile Phe Lys Gln Thr Tyr Ser
 430 ATC CAA ACG CTG ATG GGG AGG CTG GAA GAT GGC AGC CCG CGG ACT GGG CAG ATC TTC AAG CAG ACC TAC AGC
                                                                                  SacII                  BglII 150                                                           160
     Lys Phe Asp Thr Asn Ser His Asn Asp Asp Ala Leu Leu Lys Asn Tyr Gly Leu Leu Tyr Cys Phe Arg Lys
 502 AAG TTC GAC ACA AAC TCA CAC AAC GAT GAC GCA CTA CTC AAG AAC TAC GGG CTG CTC TAC TGC TTC AGG AAG 170                                                       180                                                     190
     Asp Met Asp Lys Val Glu Thr Phe Leu Arg Ile Val Gln Cys Arg Ser Val Glu Gly Ser Cys Gly Phe Am*
 574 GAC ATG GAC AAG GTC GAG ACA TTC CTG CGC ATC GTG CAG TGC CGC TCT GTG GAG GGC AGC TGT GGC TTC TAG
                                                          MstI                                                                                  PvuII
```

```
                                    hinPI
                                    hhaI
                                    thaI                        ahaII
                                    fauDI                       acyI ddeI
                       alaIV bstUI[M.hhaI-]                     actII
           sau96I[M.haeIII-]                                                    alaIII
           haeIII                                                               bspBI  mnlI
           asuI
           ecoO109I
      mnlI         mboII
4741 CAAAATAAA CAATACGGG TCCCGCGAC ATTTCCCCGA AAAGTCCAC CTGACGTCTA AGAAACCATT ATTATCATGA CATTAACCTA TAAAATAGG
     GTTTTATTT GTTATGCCC AGGGCGCTG TAAAGGGGCT TTTCAGGTG GACTGCAGAT TCTTTGGTAA TAATAGTACT GTAATTGGAT ATTTTATCC

4841 CGTATCACCA GCCCTTTCC TCTTCAA
     GCATAGTGGT CGGGAAAGC AGAAGTT

>length: 4867 aatII(GACGTC):       4793
accI(GTMKAC):        477[M.taqI-] 761 2753
accIII(TCCGGA):      1701 2108 2568
acyI(GRCGYC):        767 4411 4793
ahaII(GRCGYC):       767[M.hhaI-] 4411[M.hpaII-] 4793
ahaIII(TTTAAA):      3739 3758 4450
aluI(AGCT):          72 203 271 522 678 692 1019 1032 1040 2036 2093 2166 2423 2623 2642 2923 3149
                     3239 3285 3542 4063 4163 4226
alwI(GGATC):         816 817 1704 2105 2106 2571 2572 3549 3623 3635 3720 3733 4197 4500 4518
alwNI(CAGNNNCTG):    728 3393
apaI(GGGCCC):        504
apaLI(GTGCAC):       2798 3296 4542
asuI(ATTAAT):        4046
asuII(GGNCC):        504 505 802 1182 1297 1476 1518 1797 1986 2328 3917 3996 4013 4235 4851
asuII(TTCGAA):       778
avaI(CYCGRG):        716[M.taqI-] 1462
avaII(GGWCC):        802 1476[dcm-] 1518 1797 4013 4235
avaIII(ATYCAT):      453
balI(TGGCCA):        1481[dcm-]
bamHI(GGATCC):       816 2105[M.mspI-] 2571[M.mspI-]
banI(GGYRCC):        767 1086 1129 1326 2374 3823
banII(GRGCYC):       504[M.haeIII-] 677[M.aluI-] 719 2408
bbvI(GCAGC):         204 207 697 849 940 1017 1033 1236 1443 1467 1596 1599 1722 2516 2621 2718 2887
                     2905 3324 3389 3392 3598 3926 4115 4292
bclI[dam-] (TGATCA): 138
```

FIG. 10J

```
bglI(GCCRRRNNGGC):    3989[M.haeIII-]
bglII(AGATCT):        867
bmsI(GAATGC):         182 455 1390
bsmAI(GTCTC):         295 977 2631 3942 4707
bsp1286(GDGCHC):      504[M.haeIII-] 677[M.aluI-] 719 1502 2408 2798 3296 4457 4542
bspBI(TCATGA):        3702 4710 4815
bspMI(ACCTGC):        792
bsphII(TCCGGA):       1701 2108 2568
bstEI(ACTGG):         706 860 1220 1547 1818 1842 2250 2729 2757 3385 3398 3515 3921 4039 4082 4346
                      4521
bstBI(TTCGAA):        778
bstNI(CCWGG):         541 757 1140 1479 3009 3130 3143
bstUI(CGCG):          211[M.hhaI-] 647 855 1271 1281 1426 1452 1574 1671 2043 2144 2520[M.hhaI-] 2540[M.hhaI-]
                      2564[M.hhaI-] 2582[M.hhaI-] 2584[M.hhaI-] 2687[M.hhaI-] 3028 3609[M.hhaI-] 3939
                      4432[M.hhaI-] 4764[M.hhaI-]
bsuXI(CCARRRNNNTGG):  750
bstYI(RGATCT):        816 867 1704 2105 2571 3623 3634 3720 3732 4500 4517
beu36I(CCTNAGG):      733
cauII(CCSGG):         1180 1295 1521 1849 2627 2662 3361 4057 4408
ctrI(YGGCCR):         290 1481 4263
claI(ATCGAT):         625
ddeI(CTNAG):          57 473 619 734 1618 1780 2792 3257 3666 3832 4372 4798
dpnI(GATC):           139 817 868 1498 1705 2106 2572 3549 3624 3635 3643 3721 3733 3838 4179 4197
                      4243 4501 4518 4554
draI(TTTAAA):         3739 3758 4450
draIII(CACNNNGTG):    2332
eaeI(YGGCCR):         290 1481 4263
eagI(CGGCCG):         290
earI(CTCTTC):         551 2860 4664
ecoBII(CCTNAGG):      733
ecoMI(CCTNNNNNAGG):   793
ecoO109I(RGGNCCY):    801 1475[dcm-] 1517 4850
ecoRI(GAATTC):        1
ecoRII(CCWGG):        541 757 1140 1479 3009 3130 3143
ecoRV(GATATC):        1195
fauHI(CCMGC):         204 207 697 849 940 1002 1017 1033 1236 1245 1324 1443 1446 1453 1467 1596 1599
                      1722 1803 2516 2538 2552 2621 2718 2771 2887 2905 2908 3026 3181 3324 3389 3392
                      3598 3926 4115 4265 4292 4387 4616
fnuDII(CGCG):         211 647 855 1271 1281 1426 1452 1574 1671 2043 2144 2520 2540 2564 2582 2584
                      2687 3028 3609 3939 4432 4764
fokI(GGATG):          238 703 1122 1143 1718 1807 1885 2046 2657 3855 4036 4323
fspI(TGCGCA):         987 1393 1491 4095
haeI(WGGCCW):         555 1481 2995 3006 3458
haeII(RGCGCY):        153 767 1242 1681 1764 2484 2492 2856 3226
haeIII(GGCC):         291 505 556 1183 1298 1482 1986 2186 2328 2996 3007 3025 3459 3917 3997 4264
                      4851
```

FIG.10K

```
hgaI(GACGC):          917 1277 1427 2041 2565 2688 3084 3662 4412
hgLAI(GWGCWC):        672[M.aluI-] 1502 2798 3296 4457 4542
hgiCI(GGTRCC):        767 1086 1129 1326 2374 3823
hgiJII(GRGCYC):       504 677 719 2408
hhaI(GCGC):           112 154 210 768 988 1111 1243 1394 1456 1492 1682 1765 2485 2493 2519 2541 2550
                      2563 2583 2686 2716 2857 2890 3160 3227 3501 3610 4003 4096 4433 4765
hinFI(GCGC):          112 154 210 768 988 1111 1243 1394 1456 1492 1682 1765 2485 2493 2519 2541 2550
                      2563 2583 2686 2716 2857 2890 3160 3227 3501 3610 4003 4096 4433 4765
hincII(GTYRAC):       477[M.taqI-] 4414
hindII(GTYRAC):       477 4414 hindIII(AAGCTT):      71 691
hinfI(GANTC):         623[M.taqI-] 628[M.taqI-] 776[M.taqI-] 1341[M.hphI-] 1562[M.hphI-] 2068 2264
                      2286 2882 2957 3353 3870
hpaII(CCGG):          1171 1180 1295 1321 1522 1702 1849 2109 2439 2569 2628 2662 3189 3336 3362 3552
                      3956 3990 4057 4167 4409
hphI(GGTGA):          380 1136 1344 1565 2346 2592 2601 3726 3953 4349 4575 4590
mboII(GAAGA):         409 514 551 744 842 870[dam-] 1638 2465 2861 3632[dam-] 3723[dam-] 4478 4556[dam-]
                      4665 4861
mboI[dam-](GATC):     139 817 868 1498 1705 2106 2572 3549 3624 3635 3643 3721 3733 3838 4179 4197
                      4243 4501 4518 4554
mnII(CCTC):           148 163 241 372 378 554 606 610 639 650 682 736 771 809 835 1013 1125 1185 1265
                      1303 1330 1516 1830 1888 1944 2372 2579 2609 2871 3097 3154 3421 3821 3902 4032
                      4238 4849
msiI(TTAA):           69 257 724 1044 1066 1757 1979 2011 2125 2136 2148 2159 2176 2274 2545 2763
                      3688 3740 3745 3759 3812 4047 4086 4451 4823
mspI(CCGG):           1171 1180 1295 1321 1522 1702 1849 2109[M.bamHI-] 2439 2569[M.bamHI-] 2628 2662
                      3189 3336 3362 3552 3956 3990 4057 4167 4409
msaI(TCCGGA):         987 1393 1491 4095
maII(CTYRAGG):        733
msaI(GCCGGC):         1320 2438
mszI(GGGGCC):         767
sciI(CCSGG):          1180 1295 1521 1849 2627 2662 3361 4057 4408
nsbI(GAATGC):         2804
ndeI(CATATG):         523[M.aluI-] 1239
nheI(GCTAGC):         40 964 1208 1495 1629 1854 1918 1983 2618 2723 2983 3703 4194 4204 4282 4318
nlaIII(CATG):         4711 4816
nlaIV(GGNNCC):        504 767 816 1086 1129 1291 1326 1361 1475 1518 1797 2105 2374 2395 2407 2571
                      3012 3051 3823 3917 3958 4169 4759
nraI(TCCGA):          646
nzII(ATGCAT):         453
aspCIs(RCATGY):       1853 2617 2982
pacJ)I(TTCAG):        716
pflMI(CCANNNNNTGC):   14 1352 1401
plaI(GACTC):          2264 2286 2882 3353 3870
ppuMI(RGGWCCY):       801 1475 1517
patI(CTGCAG):         590 4116[M.BI-]
```

FIG.10L

```
pvuI(CGATCG):      4242
pvuII(CAGCTG):     270 1018[M.H1-]
rsaI(GTAC):        139 342 787 1174 2789 4354
sacI(GAGCTC):      677
sacII(CCGCGG):     854
salI(GTCGAC):      477
sau3AI(GATC):      139 817 868 1498 1705 2106 2572 3549 3624 3635 3643 3721 3733 3838 4179 4197
                   4243 4501 4518 4554
sau96I(GGNCC):     504[M.haeIII-] 505[M.haeIII-] 802 1182[M.haeIII-] 1297[M.haeIII-] 1476[dcm-]
                   1518 1797 1986[M.haeIII-] 2328[M.haeIII-] 3917[M.haeIII-] 3996[M.haeIII-] 4013
                   4235 4851[M.haeIII-]
scaI(AGTACT):      4353
scrFI(CCSGG):      1180 1295 1521 1849 2627 2662 3361 4057 4408
scrFI[dcm-](CCWGG): 541 757 1140 1479 3009 3130 3143
sfaNI(GCATC):      175 237 416 990 1144 1214 1458 1710 1719 1806 1884 1947 2658 2774 2829 2850
                   3070 4122 4332 4562
snaBI(TACGTA):     217
speI(ACTAGT):      338
sspI(AATATT):      2127 4677
sstI(GAGCTC):      677
stuI(AGGCCT):      555
styI(CCWWGG):      567 1406
taqI(TCGA):        478 486 626[M.claI-] 717 779 894 975 1305 2370 3082 4526
thaI(CGCG):        211 647 855 1271 1281 1426 1452 1574 1671 2043 2144 2520 2540 2564 2582 2584
                   2687 3028 3609 3939 4432 4764
tth111I(GACNNNGTC): 968 2726
xbaI(TCTAGA):      368
xhoI(CTCGAG):      716
xhoII(RGATCY):     816 867 1704 2105 2571 3623 3634 3720 3732 4500 4517
xmaIII(CGGCCG):    290
xmnI(GAANNNNTTC):  623 2068 4470
not found:
afIII(CTTAAG), asp718(GGTACC), avrII(CCTAGG), bssHII(GCGCGC), bstEII(GGTNACC), espI(GCTNAGC), hpaI(GTTAAC),
kpnI(GGTACC), mluI(ACGCGT), ncoI(CCATGG), notI(GCGGCCGC), rsrII(CGGWCCG), sfiI(GGCCNNNNNGGCC), smaI(CCCGGG),
sphI(GCATGC), xmaI(CCCGGG)
```

```
alwI(GGATC):                    851 1095 1339 1340 1852 2253 2254 2719 2720 3697 3771 3783 3868 3881 4345 4648
                                4666
alwNI(CAGNNNCTG):               3541
apaLI(GTGCAC):                  2946 3444 4690
aseI(ATTAAT):                   4194
asuI(GGNCC):                    641 1024 1445 1624 1666 1945 2134 2476 4065 4144 4161 4383 4999
avaI(CYCGRG):                   1610
avaII(GGWCC):                   641 1024 1624[dcm-] 1666 1945 4161 4383
avaIII(ATGCAT):                 453
avrII(CCTAGG):                  637
balI(TGGCCA):                   1629[dcm-]

bamHI(GGATCC):                  1339 2253[M.mspI-] 2719[M.mspI-]
banI(GGYRCC):                   1674 2522 3971
banII(GRGCYC):                  2556
bbvI(GCAGC):                    204 207 479 1221 1384 1591 1615 1744 1747 1870 2664 2769 2866 3035 3053 3472
                                3537 3540 3746 4074 4263 4440 bclI[dam-](TGATCA):             138
bglI(GCCNNNNNGGC):              4137[M.haeIII-]
bglII(AGATCT):                  182 701 1289 1538
bsmI(GAATGC):                   295 587 2779 4090 4855
bsmAI(GTCTC):                   495 1139 1650 2556 2946 3446 4605 4690
bsp1286(GDGCHC):                3850 4858 4963
bspHI(TCATGA):                  1849 2256 2716
bspMII(TCCGGA):                 603 870 896 1049 1368 1695 1966 1990 2398 2877 2905 3533 3546 3663 4069 4187
bsrI(ACTGG):                    4230 4494 4669 bstNI(CCWGG):                   501 524 1627 3157 3278 3291
bstUI(CGCG):                    211[M.hhaI-] 1203 1419 1429 1574 1600 1722 1819 2191 2292 2668[M.hhaI-] 2698[M.hhaI-]
                                2712[M.hhaI-] 2730[M.hhaI-] 2835[M.hhaI-] 3176 3757[M.hhaI-] 4087
                                4580[M.hhaI-] 4912[M.hhaI-]

bstYI(RGATCY):                  850 1094 1339 1852 2253 2719 3771 3782 3868 3880 4648 4665
cauII(CCSGG):                   1443 1669 1997 2775 2810 3509 4205 4556
cfrI(YGGCCR):                   290 1199 1629 4411
ddeI(CTNAG):                    57 488 546 579 1158 1766 1928 2940 3405 3814 3980 4520 4946
dpnI(GATC):                     139 851 1095 1340 1646 1853 2254 2720 3697 3772 3783 3791 3869 3881 3986 4327
                                4345 4391 4649 4666 4702 draI(TTTAAA):                   3887 3906 4598
draIII(CACNNNGTG):              562 2480
eaeI(YGGCCR):                   290 1199 1629 4411
eagI(CGGCCG):                   290 1199
earI(CTCTTC):                   3008 4812
eco0109I(RGGNCCY):              640 1623[dcm-] 1665 4998
ecoRI(GAATTC):                  1
ecoRII(CCWGG):                  501 524 1627 3157 3278 3291
ecoRV(GATATC):                  911
```

FIG. 12K

```
fau4HI(GCNGC):    204 207 479 1198 1201 1221 1384 1393 1472 1591 1594 1601 1615 1744 1747 1870
                  1951 2664 2686 2700 2769 2866 2919 3035 3053 3056 3174 3329 3472 3537 3540 3746
                  4074 4263 4413 4440 4535 4764
fmuDII(CCGG):     211 1203 1419 1429 1574 1600 1722 1819 2191 2292 2668 2688 2712 2730 2732 2835
                  3176 3757 4087 4580 4912
fokI(GGATC):      238 811 959 963 1866 1955 2033 2194 2805 4003 4184 4471
fspI(TGCGCA):     1541 1639 4243
haeI(WGGCCW):     471 526 1629 3143 3154 3606
haeII(RGCGCY):    153 1390 1829 1912 2632 2640 3004 3374
haeIII(GGCC):     291 472 527 1200 1446 1630 2134 2334 2476 3144 3155 3173 3607 4065 4145 4412
                  4999
hgaI(GACGC):      1425 1575 2189 2713 2836 3232 3810 4560
hgiAI(GWGCWC):    495 1139 1650 2946 3444 4605 4690
hgiCI(GGTRCC):    1474 2522 3971
hgiJII(GRGCYC):   2556
hhaI(GCGC):       112 154 210 1391 1542 1604 1640 1830 1913 2633 2641 2667 2689 2698 2711 2731
                  2834 2864 3005 3038 3308 3375 3475 3649 3758 4151 4244 4581 4913
hinPI(GCGC):      112 154 210 1391 1542 1604 1640 1830 1913 2633 2641 2667 2689 2698 2711 2731
                  2834 2864 3005 3038 3308 3375 3475 3649 3758 4151 4244 4581 4913
hincII(GTYRAC):   1206 4562
hindII(GTYRAC):   1206 4562
hindIII(AAGCTT):  71
hinfI(GANTC):     505 685 901 1489[M.hphI-] 1710[M.hphI-] 2216 2412 2434 3030 3105 3501 4018
hpaI(GTTAAC):     1206
hpaII(CCGG):      1443 1469 1670 1850 1997 2257 2587 2717 2776 2810 3337 3484 3510 3700 4104 4138
                  4205 4315 4557
hphI(GGTGA):      380 561 575 1492 1713 2494 2740 2749 3874 4101 4497 4723 4738
mboII(GAAGA):     409 542 1181 1186 1786 2613 3009 3780[dam-] 3871[dam-] 4626 4704[dam-] 4813
                  5009
mboI[dam-](GATC): 139 851 1095 1340 1646 1853 2254 2720 3697 3772 3783 3791 3869 3881 3986 4327
                  4345 4391 4549 4666 4702
mnlI(CCTC):       148 163 241 372 378 470 614 759 865 1136 1157 1413 1451 1478 1664 1978 2036
                  2092 2520 2727 2757 3019 3245 3302 3569 3969 4050 4180 4386 4997
mseI(TTAA):       69 257 324 519 744 893 1207 1905 2127 2159 2273 2284 2296 2307 2324 2422 2693
                  2911 3836 3888 3893 3907 3960 4195 4234 4599 4971
mspI(CCGG):       1443 1469 1670 1850 1997 2257[M.bamHI-] 2587 2717[M.bamHI-] 2776 2810 3337 3484
                  3510 3700 4104 4138 4205 4315 4557
nciI(TCCGGA):     1541 1639 4243
neaI(GCCGGC):     1468 2586
ncII(CCSGG):      1443 1669 1997 2775 2810 3509 4205 4556
ndeI(CATATG):     2952
nheI(GCTAGC):     1387
```

FIG.12L

```
alaIII(CATG):           40 597 623 905 1176 1332 1436 1643 1777 2002 2066 2131 2766 2871 3131 3851 4342
                        4352 4430 4466 4859 4964
alaIV(GGNCC):           550 641 1024 1339 1439 1474 1509 1623 1666 1945 2253 2322 2543 2555 2719 3160
                        3199 3971 4065 4106 4317 4907
aoII(CCGCCGC):          1198
adI(ATCGAT):            453
bspCIx(RGATGT):         1175 2001 2765 3130
pflMI(CCANNNNNTGG):     14 1500 1549
pleI(GACTC):            505 685 2412 2434 3030 3501 4018
ppuMI(RGGWCCY):         640 1623 1663
psI(CTGCAG):            4264[M.BI-]
pvuI(CGATCG):           4390
pvuII(CAGCTG):          270 650 733
rsaI(GTAC):             159 342 627 804 1054 2937 4502
sau3AI(GATC):           139 851 1095 1340 1646 1853 2254 2720 3697 3772 3783 3791 3869 3881 3986 4327
                        4345 4391 4649 4666 4702
sau96I(GGNCC):          641 1024 1445[M.haeIII-] 1624[dcm-] 1666 1945 2134[M.haeIII-] 2476[M.haeIII-]
                        4065[M.haeIII-] 4144[M.haeIII-] 4161 4383 4999[M.haeIII-]
                        4501
scaI(AGTACT):           1443 1669 1997 2775 2810 3509 4205 4556
scrFI(CCSGG):           501 524 1627 3157 3278 3291
sexFI[dcm-](CCWGG):     175 237 416 1252 1362 1606 1858 1867 1954 2032 2095 2806 2922 2977 2998 3218
sfaNI(GCATC):           4270 4480 4710
                        4501
snaBI(TACGTA):          217
speI(ACTAGT):           338
sphI(AATATT):           2275 4825
stuI(AGGCCT):           526[dcm-]
styI(CCWWGG):           637 1554
taqI(TCGA):             1453 2518 3230 4674
tbaI(CGCG):             211 1203 1419 1429 1574 1600 1722 1819 2191 2292 2668 2688 2712 2730 2732 2835
                        3176 3757 4087 4580 4912
tch111I(CACNNNGTC):     2874
xbaI(TCTAGA):           368
xboII(RGATCY):          850 1094 1339 1852 2253 2719 3771 3782 3868 3880 4648 4665
xmaIII(CGGCCG):         290 1199
xmnI(GAANNNNTTC):       2216 4618
not found:

afIII(CTTAAG), apaI(GGGCCC), asp718(GGTACC), asuII(TTCGAA), bglII(AGATCT), bspMI(ACCTGC), bssHII(GCGCGC),
bstBI(TTCGAA), bstEII(GGTNACC), bstXI(CCANNNNNNTGG), bsu36I(CCTNAGG), claI(ATCGAT), ecoBII(CCTNAGG), ecoNI(CCTNNNNNAGG),
espI(GCTNAGC), kpnI(GGTACC), mluI(ACGCGT), mstII(CCTNAGG), narI(GGCGCC), ncoI(CCATGG), nruI(TCGCGA), pssR7I(CTCGAG),
rsrII(CGGWCCG), sacI(GAGCTC), sacII(CCGCGG), salI(GTCGAC), sfiI(GCCNNNNNGGCC), smaI(CCCGGG), sphI(GCATGC),
sstI(GAGCTC), xhoI(CTCGAG), xmaI(CCCGGG)
```

FIG. 12M

● pGH (11-33) minus hPRL (22-33)
▽ hPRL (12-19) minus hPL (12-25)
▲ hPRL (97-104)

FIG.—17 x Deletion (32-46)

FIG.—23

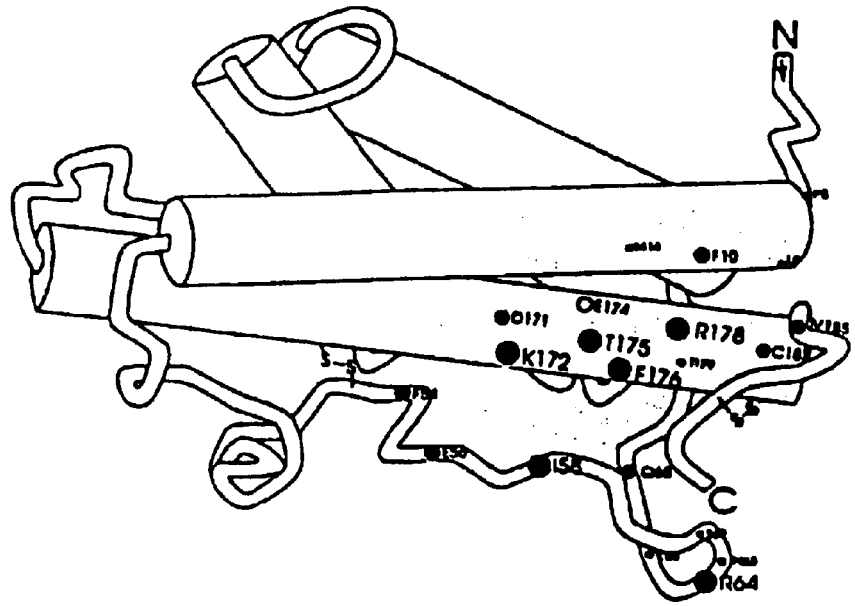
FIG.—25A
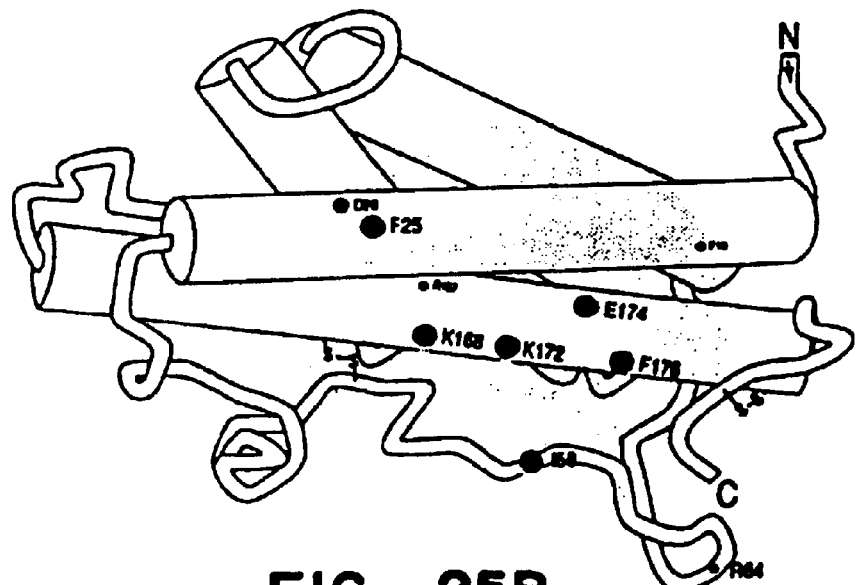
FIG.—25B

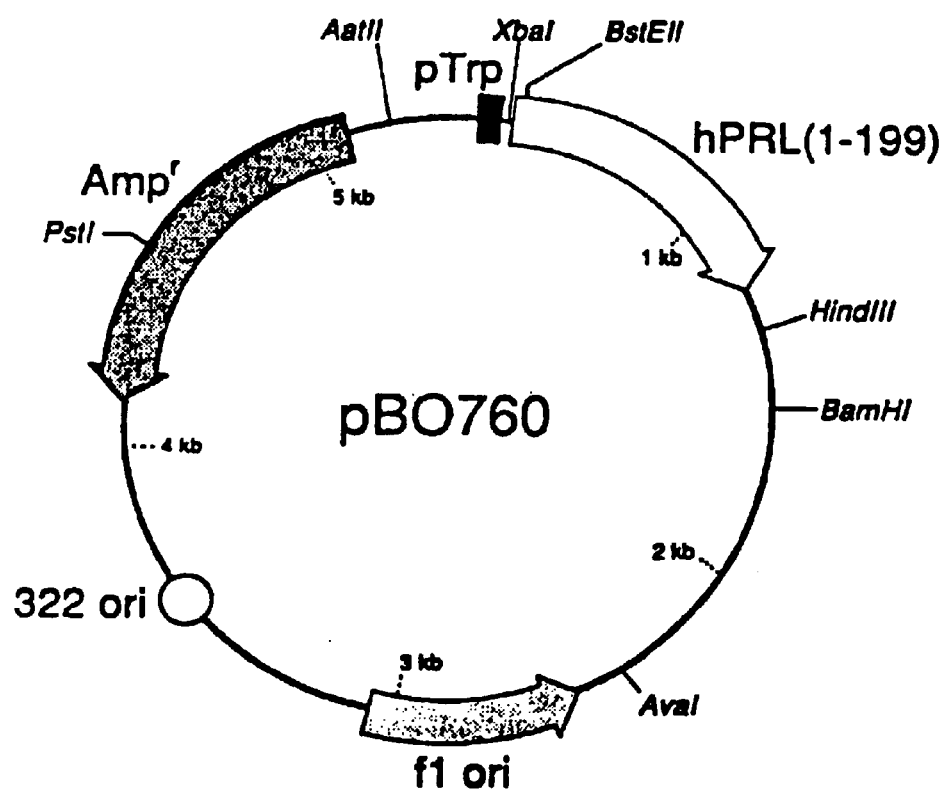
FIG.—26

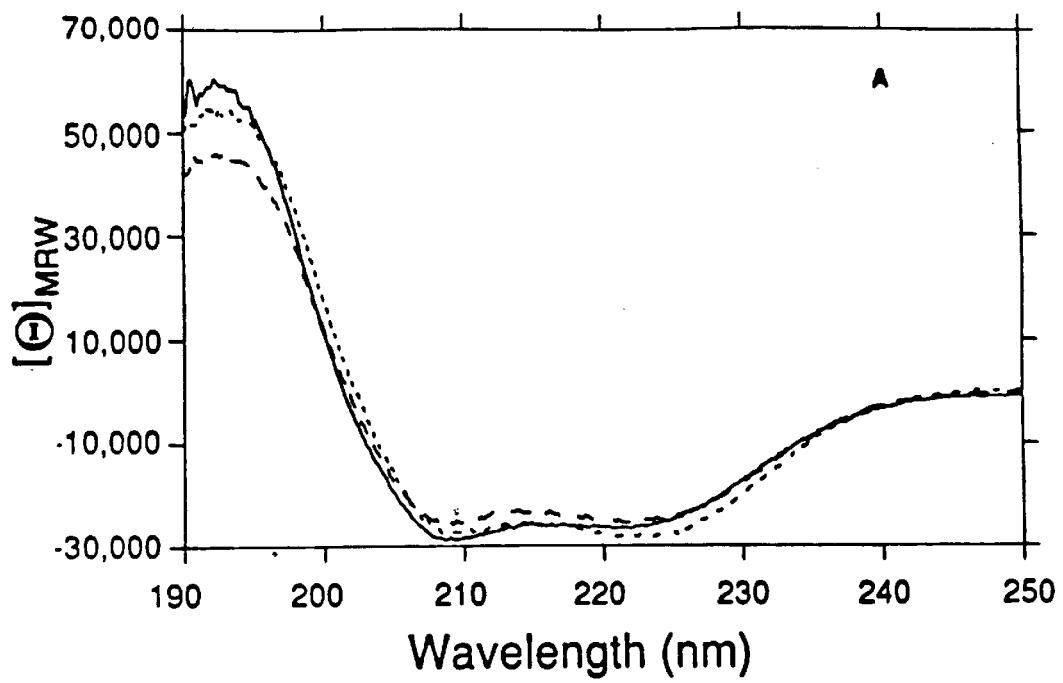
FIG.—28A
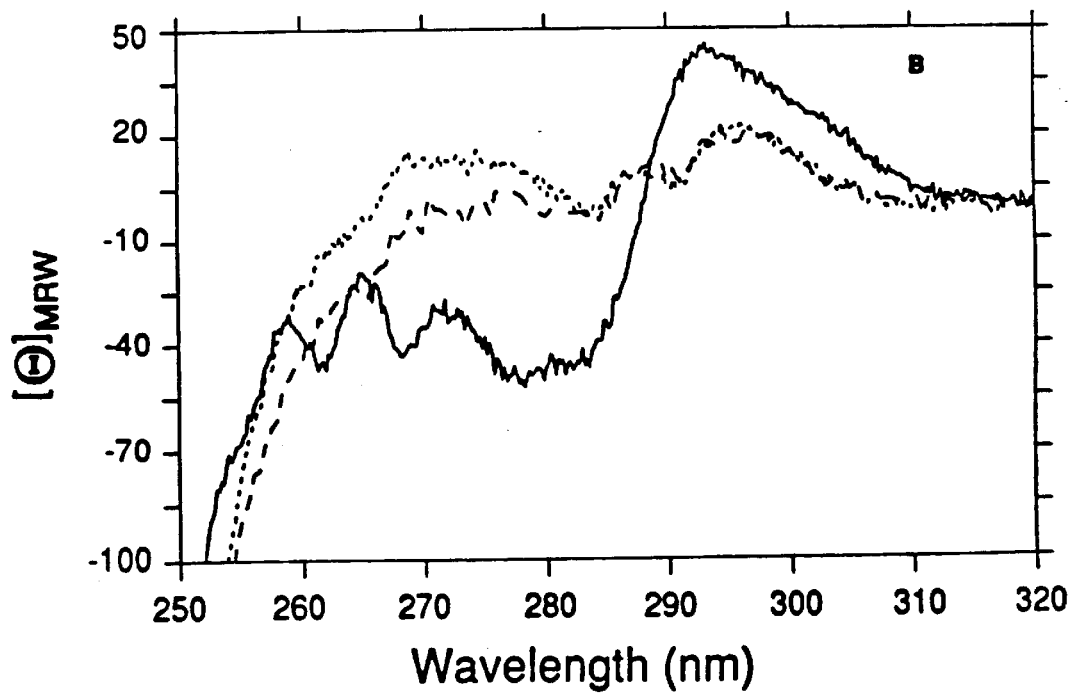
FIG.—28B

FIG.–29

GROWTH HORMONE VARIANTS

This application is a division of application Ser. No. 08/190,723, filed Feb. 2, 1994, which is a continuation of application Ser. No. 07/960,227, filed Oct. 13, 1992, now abandoned, which is a continuation of Ser. No. 07/875,204, filed Apr. 27, 1992, now abandoned, which is a continuation of Ser. No. 07/428,066, filed Oct. 26, 1989, now abandoned, which is a continuation-in-part of Ser. No. 07/264,611, filed Oct. 28, 1988, now abandoned.

FIELD OF THE INVENTION

The invention is directed to methods for identifying the active domains and amino acid residues in polypeptides. It is also directed to hormone variants.

BACKGROUND OF THE INVENTION

Polypeptides, i.e., peptides and proteins, comprise a wide variety of biological molecules each having a specific amino acid sequence, structure and function. Most polypeptides interact with specific substances to carry out the function of the polypeptide. Thus, enzymes, such as subtilisin, amylase, tissue plasminogen activator, etc., interact with and hydrolyze specific substrates at particular cleavage sites whereas proteinaceous hormones such as human growth hormone, insulin and the like interact with specific receptors to regulate growth and metabolism. In other cases, the interaction is between the polypeptide and a substance which is not the primary target of the polypeptide such as an immunogenic receptor. Many polypeptides are pluripotential in that they contain discrete regions which interact with different ligands or receptors each of which produces a discrete biological effect. For example, human growth hormone (hGH) is diabetogenic and lypogenic in adults and induces long bone growth in children.

Efforts have been made to modify the primary functional properties of naturally occurring polypeptides by modifying amino acid sequence. One approach has been to substitute one or more amino acids in the amino acid sequence of a polypeptide with a different amino acid. Thus, protein engineering by in vitro mutagenesis and expression of cloned genes reportedly has been applied to improve thermal or oxidative stability of various proteins. Villafranca, J. E., et al. (1983) *Science* 222, 782–788; Perry, L. J., et al. (1984) *Science* 226, 555–557; Estell, D. A., et al. (1985) *J. Biol. Chem.* 260, 6518–6521; Rosenberg, S., et al. (1984) *Nature (London)* 312, 77–80; Courtney, M., et al. (1985) *Nature (London)* 313, 149–157. In addition, such methods have reportedly been used to generate enzymes with altered substrate specificities. Estell, D. A., et al. (1986) *Science* 223, 655–663; Craik, C. S., et al. (1985) *Science* 228, 291–297; Fersht, A. R., et al. (1985) *Nature (London)* 314, 235–238; Winther, J. R., et al. (1985) *Carlsberg Res. Commun.* 50, 273–284; Wells, J. A., et al. (1987) *Proc. Natl. Acad. Sci.* 84, 1219–1223. The determination of which amino acid residue should be modified has been based primarily on the crystal structure of the polypeptide, the effect of chemical modifications on the function of the polypeptide and/or the interaction of the polypeptide with various substances to ascertain the mode of action of the polypeptide. In some cases, an amino acid substitution has been deduced based on the differences in specific amino acid residues of related polypeptides, e.g. difference in the amino acid sequence in substrate binding regions of subtilisins having different substrate specificities. Wells, J. A., et al. (1987) *Proc. Natl. Acad. Sci. USA* 84, 5767. In other cases, the amino acid sequence of a known active region of a molecule has reportedly been modified to change that sequence to that of a known active region of a second molecule. Wharton, R. P., et al. (1985) *Nature* 316, 601–605, and Wharton, R. P., et al. (1984) *Cell* 38, 361–369 (substitution of recognition helix of phage repressor with recognition helix of different repressor); Jones, P. T., et al. (1986) *Nature* 321, 522–525 (substitution of variable region of a mouse antibody for corresponding region of human myeloma protein). While this approach may provide some predictability with regard to the properties modified by such substitutions, it is not a methodical procedure which would confirm that all regions and residues determinative of a particular property are identified. At best, empirical estimates of the energetics for the strengths of the molecular contacts of substituted residues may be ascertained. In this manner, the strengths of hydrogen bonds (Fersht, A. R., et al. (1985) *Nature* 314, 235; Bryan, P., et al. (1986) *Proc. Natl. Acad. Sci. USA* 83, 3743; Wells, J. A., et al. (1986) *Philos. Trans. R. Soc. London A.* 317, 415), electrostatic interactions (Wells, J. A., et al. (1987) *Proc. Natl. Acad. Sci. USA* 84, 1219; Cronin, C. N., et al. (1987) *J. Am. Chem. Soc.* 109, 2222), and hydrophobic and steric effects (Estell, D. A., et al. (1986) *Science* 233, 659; Chen, J. T., et al. (1987) *Biochemistry* 26, 4093) have been estimated for specific modified residues. These and other reports (Laskowski, M., et al. (1987) *Cold Spring Harbor Symp. Quant. Biol.* 52, 545; Wells, J. A., et al. (1987) *Proc. Natl. Acad. Sci. USA* 84, 5167; Jones, P. T., et al. (1986) *Nature* 321, 522; Wharton, R. P., et al. (1985) *Nature* 316, 601) have concluded that mutagenesis of known contact residues causes large effects on binding whereas mutagenesis of non-contact residues has a relatively minor effect.

A second reported approach to understand the relationship between amino acid sequence and primary function employs in vivo homologous recombination between related genes to produce hybrid DNA sequences encoding hybrid polypeptides. Such hybrid polypeptides have reportedly been obtained by the homologous recombination of trp B and trp A from *E.coli* and *Salmonella typhimurium* (Schneider, W. P., et al. (1981) *Proc. Natl. Acad. Sci USA* 78, 2169–2173); alpha 1 and alpha 2 leukocyte interferons (Weber, H. and Weissmann, C. (1983) *Nuc. Acids Res.* 11, 5661); the outer membrane pore proteins ompC and phoE from *E.coli* K-12 (Thommassen, J., et al. (1985) *EMBO* 4, 1583–1587); and thermophilic alpha-amylases from *Bacillus stearothermophilus* and *Bacillus lichiniformis* (Gray, G. L., et al. (1986) *J. Bacteriol.* 166, 635–643). Although such methods may be capable of providing useful information relating to amino acid sequence and function as well as useful hybrid polypeptides, as reported in the case of the hybrid alpha amylases, it is difficult to utilize such methods to systematically study a given polypeptide to determine the precise regions and amino acid residues in the polypeptide that are active with one of the target substances for that particular molecule. This is because the site of crossover recombination, which defines the DNA and amino acid sequence of the hybrid, is determined primarily by the DNA sequence of the genes of interest and the recombination mechanism of the host cell. Such methods do not provide for the predetermined and methodical sequential replacement of relatively small segments of DNA encoding one polypeptide with a corresponding segment from a second gene except in those fortuitous circumstances when crossover occurs near the 5' or 3' end of the gene.

The interaction of proteinaceous hormones with their receptors has reportedly been studied by several techniques.

One technique uses hormone peptide fragments to map the location of the receptor binding sites on the hormone. The other technique uses competition between neutralizing monoclonal antibodies and peptide fragments to locate the receptor binding site by epitope mapping. Exemplary of these techniques is the work reported on human growth hormone (hGH).

Human growth hormone (hGH) participates in much of the regulation of normal human growth and development. This 22,000 dalton pituitary hormone exhibits a multitude of biological effects including linear growth (somatogenesis), lactation, activation of macrophages, insulin-like effects and diabetagenic effects among others. See Chawla, R. K. (1983) *Ann. Rev. Med.* 34, 519; Edwards, C. K., et al. (1988) *Science* 239, 769; Thorner, M. O., et al. (1988) *J. Clin. Invest.* 81, 745. Growth hormone deficiency in children leads to dwarfism which has been successfully treated for more than a decade by exogenous administration of hGH. There is also interest in the antigenicity of hGH in order to distinguish among genetic and post-translationally modified forms of hGH (Lewis, U. J. (1984) *Ann. Rev. Physiol.* 46, 33) to characterize any immunological response to hGH when it is administered clinically, and to quantify circulating levels of the hormone.

hGH is a member of a family of homologous hormones that include placental lactogens, prolactins, and other genetic and species variants of growth hormone. Nichol, C. S., et al. (1986) *Endocrine Reviews* 7, 169. hGH is unusual among these in-that it exhibits broad species specificity and binds monomerically to either the cloned somatogenic (Leung, D. W., et al. (1987) *Nature* 330, 537) or prolactin receptor (Boutin, J. M., et al. (1988) *Cell* 53, 69). The cloned gene for hGH has been expressed in a secreted form in *Eschericha coli* (Chang, C. N., et al. (1987) *Gene* 55, 189) and its DNA and amino acid sequence has been reported (Goeddel, et al. (1979) *Nature* 281, 544; Gray, et al. (1985) *Gene* 39, 247). The three-dimensional structure of hGH is not available. However, the three-dimensional folding pattern for porcine growth hormone (pGH) has been reported at moderate resolution and refinement (Abdel-Meguid, S. S., et al. (1987) *Proc. Natl. Acad. Sci. USA* 84, 6434).

Peptide fragments from hGH have been used in attempts to map the location of the receptor binding site in hGH. Li, C. H. (1982) *Mol. Cell. Biochem.* 46, 31; Mills, J. B., et al. (1980) *Endocrinology* 17, 391. In another report, a fragment consisting of residues 96–133 was isolated after proteolysis of bovine growth hormone. This fragment was reported to bind to a growth hormone receptor. Yamasakin, et al. (1970) *Biochemistry* 9, 1107. However, when a larger peptide containing residues 1–133 was produced by recombinant methodology, no detectable binding activity was observed. Krivi, G. G., et al., International Symposium on Growth Hormone; Basic and Clinical Aspects, Abstract I-18, Final Program, sponsored by Serono Symposia, USA, Jun. 14–18, 1987. These results are clearly irreconcilable and demonstrate the potential unreliability of using peptide fragments to map receptor binding sites on a proteinaceous hormone, especially for those where the binding site is composed of two or more discontinuous and/or conformationally dependent epitopes.

The use of neutralizing monoclonal antibodies to locate the receptor binding sites by epitope mapping has similar limitations. For example, a monoclonal antibody was reportedly used in a receptor binding assay to compete with the hGH receptor for a peptide consisting of residues 98–128 of hGH. Even though the peptide 98–128 of the hGH hormone only binds to the neutralizing monoclonal antibody, it was proposed that this region contains the receptor binding site based on these competitive studies. Retegin, L. A., et al. (1982) *Endocrinology* 111, 668.

Similar approaches have been used in attempts to identify antigenic sites on the hGH hormone. Epitope mapping of twenty-seven different monoclonal antibodies to hGH by competitive binding reportedly resolved only four different antigenic sites on the hormone. Surowy, T. K., et al. (1984) *Mol. Immunol.* 21, 345; Aston, R., et al. (1985) *Pharmac. Ther.* 27, 403. This strategy, however, did not locate the epitopes on the amino acid sequence of the hormone.

Another approach to defining antigenic sites has been to test the binding of antibodies to short linear peptides over the protein of interest. Geysen, H. M., et al. (1984) *Proc. Natl. Acad. Sci. USA* 81, 3998; Geysen, H. M. (1985) *Immunol. Today* 6, 364. However, this approach suffers from the same limitations of using linear peptide fragments to locate receptor binding sites. To be useful, the linear sequence must be capable of adopting the conformation found in the antigen for the antibody to recognize it. Furthermore, based upon the known size of antibody epitopes from X-ray crystallography (Sheriff, S., et al. (1987) *Proc. Natl. Acad. Sci USA* 84, 8075; Amit, A. G., et al. (1986) *Science* 23, 747) it has been estimated that virtually all antibody combining sites must be, in part, discontinuous (Barlow, D. J., et al. (1986) *Nature* 322, 747) and as a result linear fragments may not adequately mimic such structure.

Peptide fragments from hGH have also been studied by non-covalently combining such fragments. Thus, several investigators have reported the analysis of the combination of relatively large fragments of human growth hormone comprising either the natural amino acid sequence or chemically modified peptides thereof. Burstein, S., et al. (1979) *J. of Endo. Met.* 48, 964 (amino terminal fragment hGH-(1–134) combined with carboxyl-terminal fragment hGH-(141–191)); Li, C. H., et al. (1982) *Mol. Cell. Biochem.* 46 31; Mills, J. B., et al. (1980) *Endocrinology* 107, 391 (subtilisin-cleaved two-chain form of hGH).

Similarly, the chemically modified fragment hGH-(1–134) and a chemically modified carboxy-terminal fragment from human chorionic somatomammotropin (also called placental lactogen), (hCS-(141–191)), have been non-covalently combined, as have the chemically modified fragments hCS-(1–133) and hGH-(141–191). U.S. Pat. No. 4,189,426. These investigators reported incorrectly that the determinants for binding to the hepatic growth hormone receptor are in the first 134 amino-terminal residues of growth hormone (Burstein, et al. (1978) *Proc. Natl, Acad. Sci. USA* 75, 5391–5394). Clearly, such techniques are subject to erroneous results. Moreover, by utilizing two large fragments this technique is only potentially able to localize the function to one or the other of the two fragments used in such combinations without identification of the specific residues or regions actively involved in a particular interaction. A review of some of the above techniques and experiments on hGH has been published. Nichol, C. S., et al. (1986) *Endocrine Rev.* 7, 169–203.

An alternative approach has been reported wherein a 7 residue peptide fragment from the "deletion peptide" of hGH (hGH-32-46) was modified to contain amino acid residues from analogous segments of growth hormone from other mammalian species. The effect, if any, of such substitutions, however, was not reported. See U.S. Pat. No. 4,699,897. Nonetheless, the shortcomings of the use of short peptide fragments are apparent since the linear sequence of such fragments must be capable of adopting the conformation found in the intact growth hormone so that it may be recognized in an in vitro or in vivo assay.

A number of naturally occurring mutants of hGH have been identified. These include hGH-V (Seeberg, P. H. (1982) *DNA* 1, 239; U.S. Pat. Nos. 4,446,235, 4,670,393 and 4,665,180) and 20K hGH containing a deletion of residues 32–46 of hGH (Kostyo, J. L., et al. (1987) *Biochemica et Biophysica Acta* 925, 314; Lewis, U. J., et al. (1978) *J. Biol. Chem.* 253, 2679).

One investigator has reported the substitution of cysteine at position 165 in hGH with alanine to disrupt the disulfide bond which normally exists between Cys-53 and Cys-165. Tokunaga, T., et al. (1985) *Eur. J. Biochem.* 153, 445. This single substitution produced a mutant that apparently retained the tertiary structure of hGH and was recognized by receptors for hGH.

Another investigator has reported the in vitro synthesis of hGH on a solid resin support. The first report by this investigator disclosed an incorrect 188 amino acid sequence for hGH. Li, C. H., et al. (1966) *J. Am. Chem. Soc.* 88, 2050; and U.S. Pat. No. 3,853,832. A second report disclosed a 190 amino acid sequence. U.S. Pat. No. 3,853,833. This latter sequence is also incorrect. In particular, hGH has an additional glutamine after position 68, a glutamic acid rather than glutamine at position 73, an aspartic acid rather than asparagine at position 106 and an asparagine rather than aspartic acid at position 108.

In addition to the foregoizng, hybrid interferons have been reported which have altered binding to a particular monoclonal antibody. Camble, r. et. al. "Properties of Interferon-α2 Analogues Produced from Synthetic Genes in Peptides: Structure and Function," *Proceedings of the Ninth American Peptide Symposium* (1985) eds. Deber et. al., Pierce Chemical Co., Chicago, Ill., pp.375–384. As disclosed therein, amino acid residues 101–114 from α-1 interferon or residues 98–114 from γ-interferon were substituted into α-2 interferon. α-2 interferon binds NK-2 monoclonal antibody whereas α-1 interferon does not. This particular region in α-2 interferon apparently was chosen because 7 of the 27 amino acid differences between α-1 and α-2 interferon were located in this region. The hybrids so obtained reportedly had substantially reduced activity with NK-2 monoclonal antibody. When tested for antiviral activity, such hybrids demonstrated antiviral activity on par with the activity of wild type α-2 interferon. Substitutions of smaller sections within these regions were also reported. Sequential substitution of clusters of 3 to 7 alanine residues was also proposed. However, only one analogue [Ala-30, 32,33] IFN-α2 is disclosed.

Alanine substitutions within a small peptide fragment of hen egg-white lysozyme and the effect of such substitutions on the stimulation of 2A11 or 3A9 cells have also been reported. Allen, P. M., et. al. (1987) *Nature* 327,713–715.

Others have reported that binding properties can be engineered by replacement of entire units of secondary structure including antigen binding loops (Jones, P. T., et al. (1986) *Nature* 321, 522–525) or DNA recognition helices (Wharton, R. P., et al. (1985) *Nature* 316, 601–605).

The references discussed above are provided solely for their disclosure prior to the filing date of the present application, and nothing herein is to be construed as an admission that the inventors are not entitled to antedate such disclosure by virtue of prior invention or priority based on earlier filed applications.

Given the state of the art as exemplified by the above references, it is apparent that a need exists for a useful method for the systematic analysis of polypeptides so as to ascertain the relationship between structure and function. Accordingly, it is an object herein to provide such methods to identify the active domains within the polypeptide which contribute to the functional activity of the polypeptide.

It is a further object herein to provide methods for determining the active amino acid residues which determine functional activity.

A further object of the invention is to provide methods for systematically identifying the biologically active domains in a polypeptide.

Further, it is an object herein to provide hormone variants having desirable biological, biochemical and immunogenic properties which are different as compared to the same properties of the hormone from which such variants are derived.

Still further it is an object herein to provide hormone variants having diminished activity with one biological function and substantial or increased activity with a second target substance.

Still further it is an object herein to provide hGH variants having modified binding and/or biological activity with the somatogenic receptor for hGH and increased potency.

Still further it is an object herein to provide hGH variants which retain one or more desirable biological properties but which also have decreased diabetogenic activity.

Further, it is an object herein to provide hPRL and hPL variants having an increased binding activity with the somatogenic receptor of hGH.

Further, it is an object herein to provide DNA sequences, vectors and expression hosts containing such vectors for the cloning and expression of polypeptide variants including hGH variants.

SUMMARY OF THE INVENTION

In one aspect, the invention provides methods for the systematic analysis of the structure and function of polypeptides by identifying unknown active domains which influence the activity of the polypeptide with a first target substance. Such unknown active-domains in one aspect of the invention may comprise at least two discontinuous amino acid segments in the primary amino acid sequence of the polypeptide. Active domains are determined by substituting selected amino acid segments of the polypeptide (referred to as the parent polypeptide) with an analogous amino acid segment from an analog to the polypeptide. The analog has a different activity with the target substance as compared to the parent polypeptide. The segment-substituted polypeptides so formed are assayed to determine the activity of each of the segment-substituted polypeptides with the target substance. Such activities are compared to the same activity for the parent polypeptide. Since the structurally analogous amino acid segments are obtained from an analog that has a different interaction with the target substance, a comparison of such activities provides an indication of the location of the active domain in the parent polypeptide.

The method further comprises identifying the active amino acid residues within the active domain of the parent polypeptide. The method comprises substituting a scanning amino acid for one of the amino acid residues within the active domain of the parent polypeptide and assaying the residue-substituted polypeptide so formed with a target substance. The activity of each of the residue-substituted polypeptides is compared to the same activity of the parent polypeptide. These steps are repeated for different amino acids in the active domain until the active amino acid residues are identified.

In another aspect, the invention provides methods to identify different active domains and active amino acid residues for different target substances. Such methods comprise repeating the foregoing methods with a second target.

In accordance with the foregoing method, polypeptide variants are identified which have a different activity with one or more target substance as compared to a parent polypeptide. Such variants are produced based on the identification of the active domains or the identification of the active amino acid residues in the active domain which determine the activity of the parent polypeptide with a target substance.

The invention further comprises growth hormone, prolactin, and placental lactogen variants comprising at least three portions. The first portion corresponds to at least a part of the amino acid sequence of a parent hormone, the third portion corresponds to the amino acid sequence of at least part of the same parent hormone, and the second portion corresponds to an amino acid sequence of an analog to the parent hormone. The second portion is analogous to those amino acid residues of the parent hormone not contained between the first and third portions of the polypeptide variant.

The invention also includes specific human growth hormone, human prolactin and human placental lactogen variants comprising segment-substituted and residue-substituted variants of hGH.

BRIEF DESCRIPTION OF THE DRAWINGS

FIG. 5 depicts the analogous amino acids in the active domains A, C and F which interact with the somatogenic hGH receptor.

FIG. 6 depicts the relative binding positions of the somatogenic receptor and eight monoclonal antibodies to hGH. The top, middle, and bottom panels in FIG. 6A show the binding positions of monoclonal antibodies 1, 8, and 7, respectively. In FIG. 6B, the top and bottom panels show the binding positions of monoclonal antibodies 2 and 6, respectively, while the binding position of the somatogenic receptor is shown in the middle panel. The top, middle, and bottom panels in FIG. 6C show the binding positions of monoclonal antibodies 3, 4, and 5, respectively.

FIG. 7 is a bar graph showing the relative increase or decrease in binding to the soluble hGH somatogenic receptor for various alanine-substituted hGH variants. The stippled bar at T175 indicates that serine rather than alanine is substituted. The broken bar at R178 indicates that asparagine rather than alanine is substituted.

FIG. 8 depicts the DNA and amino acid sequence of the hGH gene used in the examples.

Figure 10A:
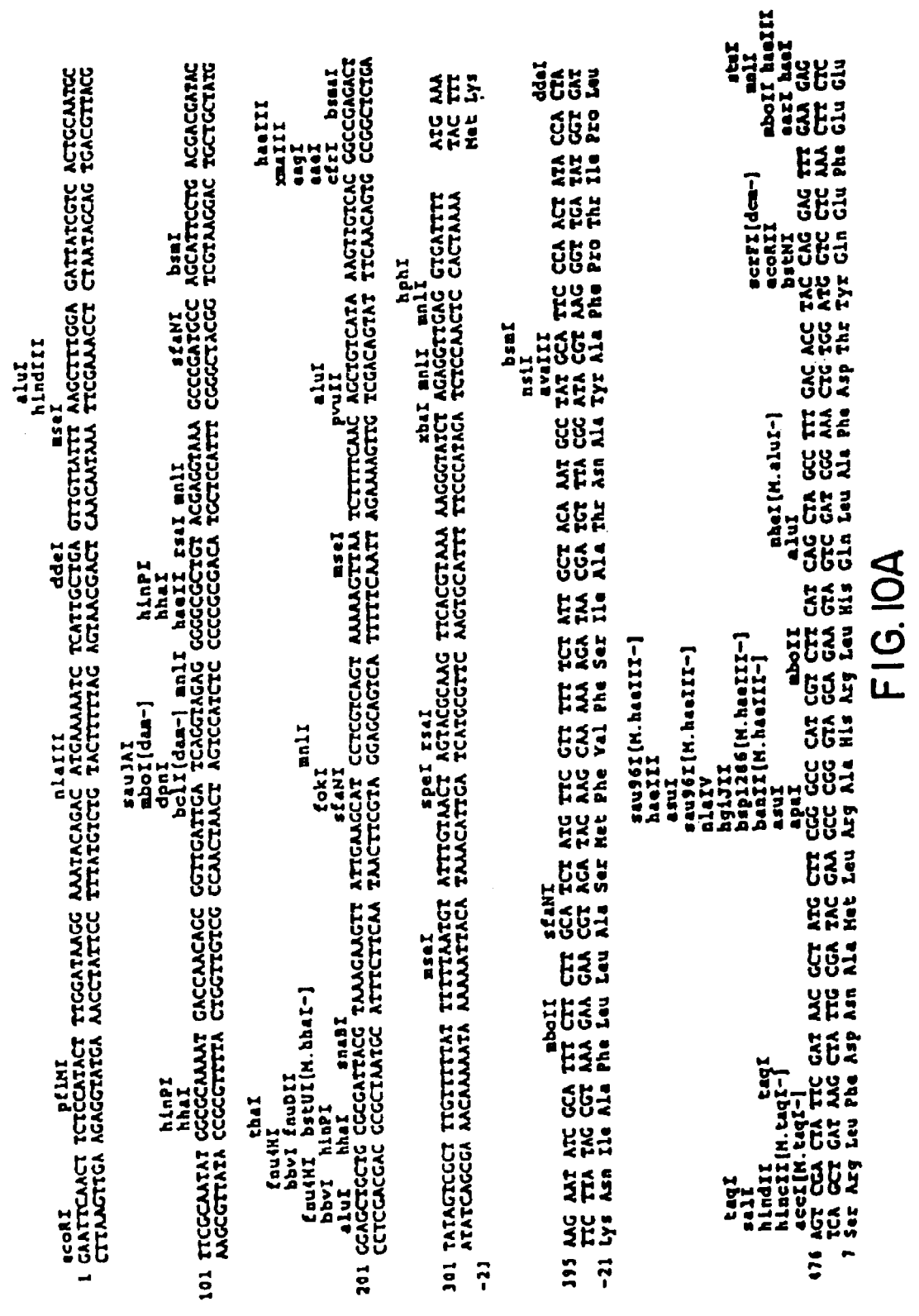
Figure 10B:
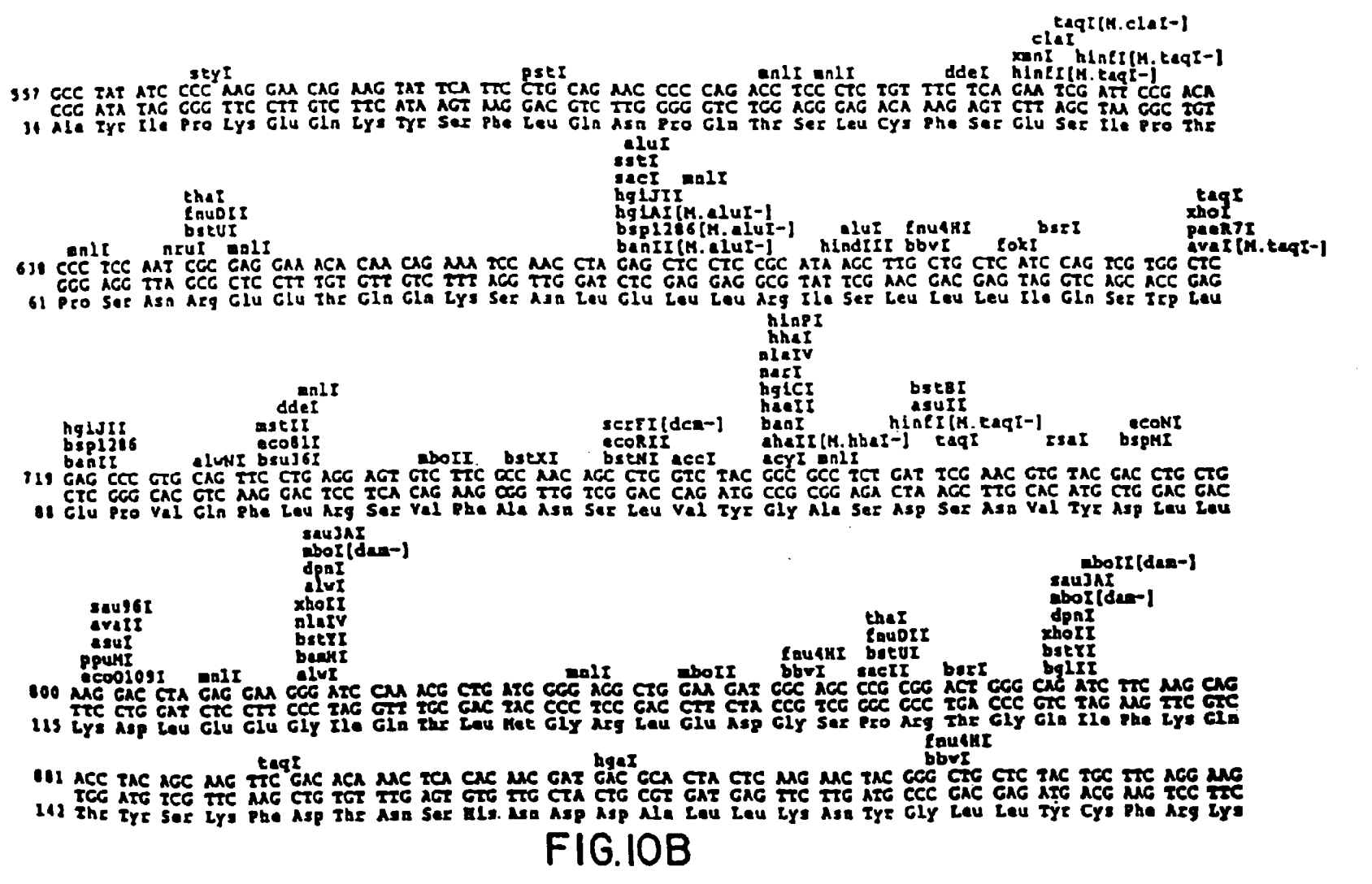
Figure 10C:
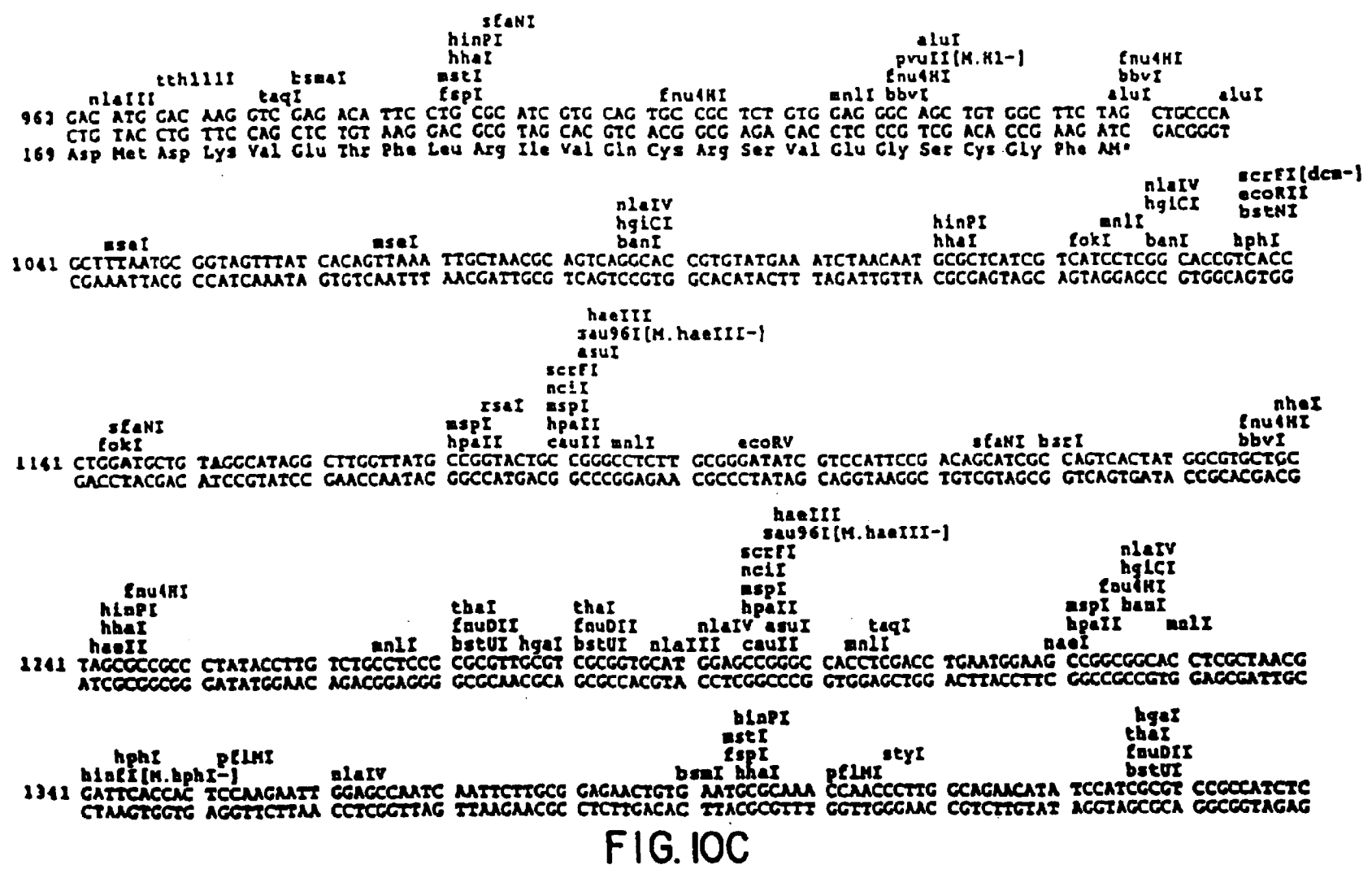
Figure 10D:
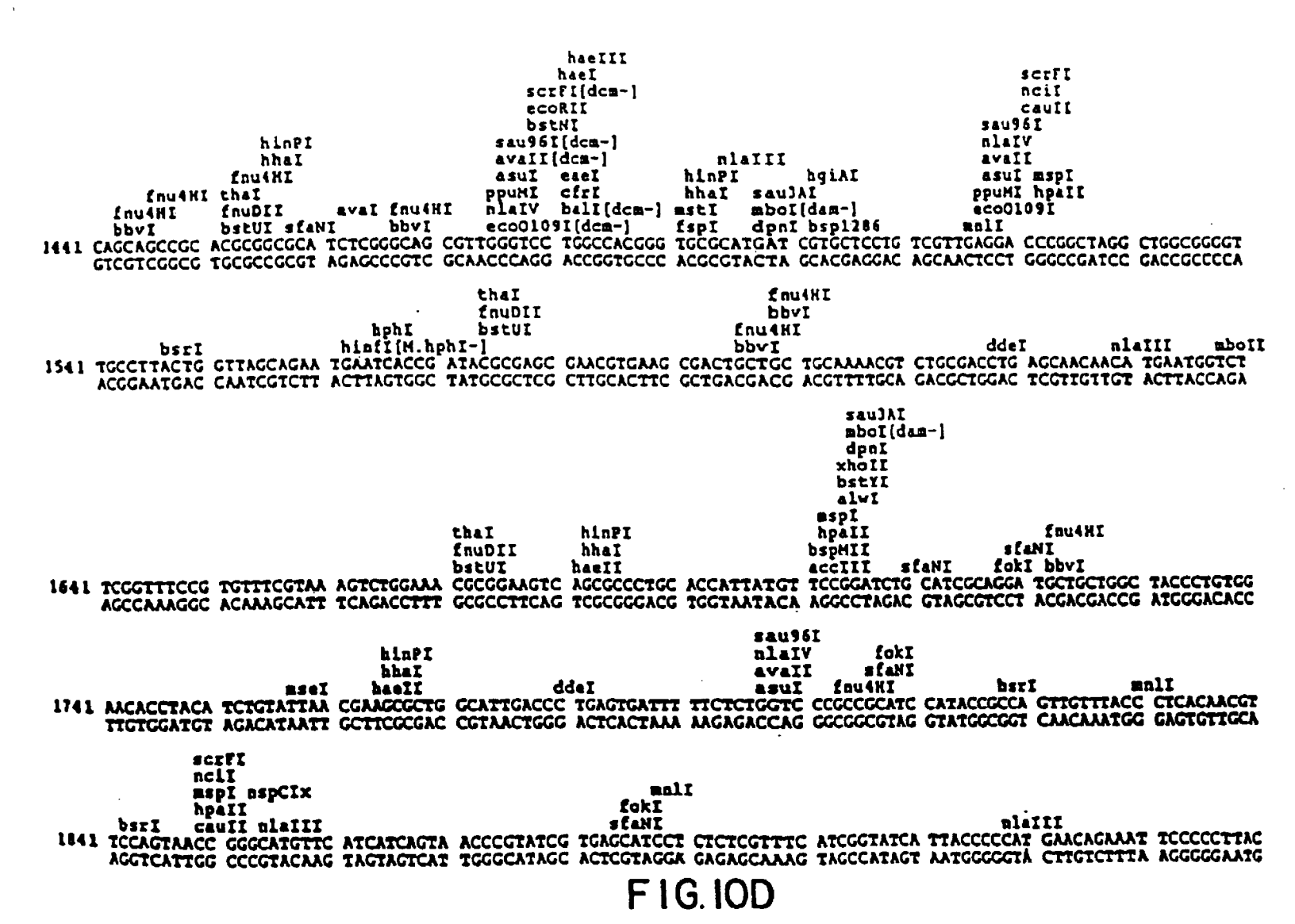
Figure 10E:
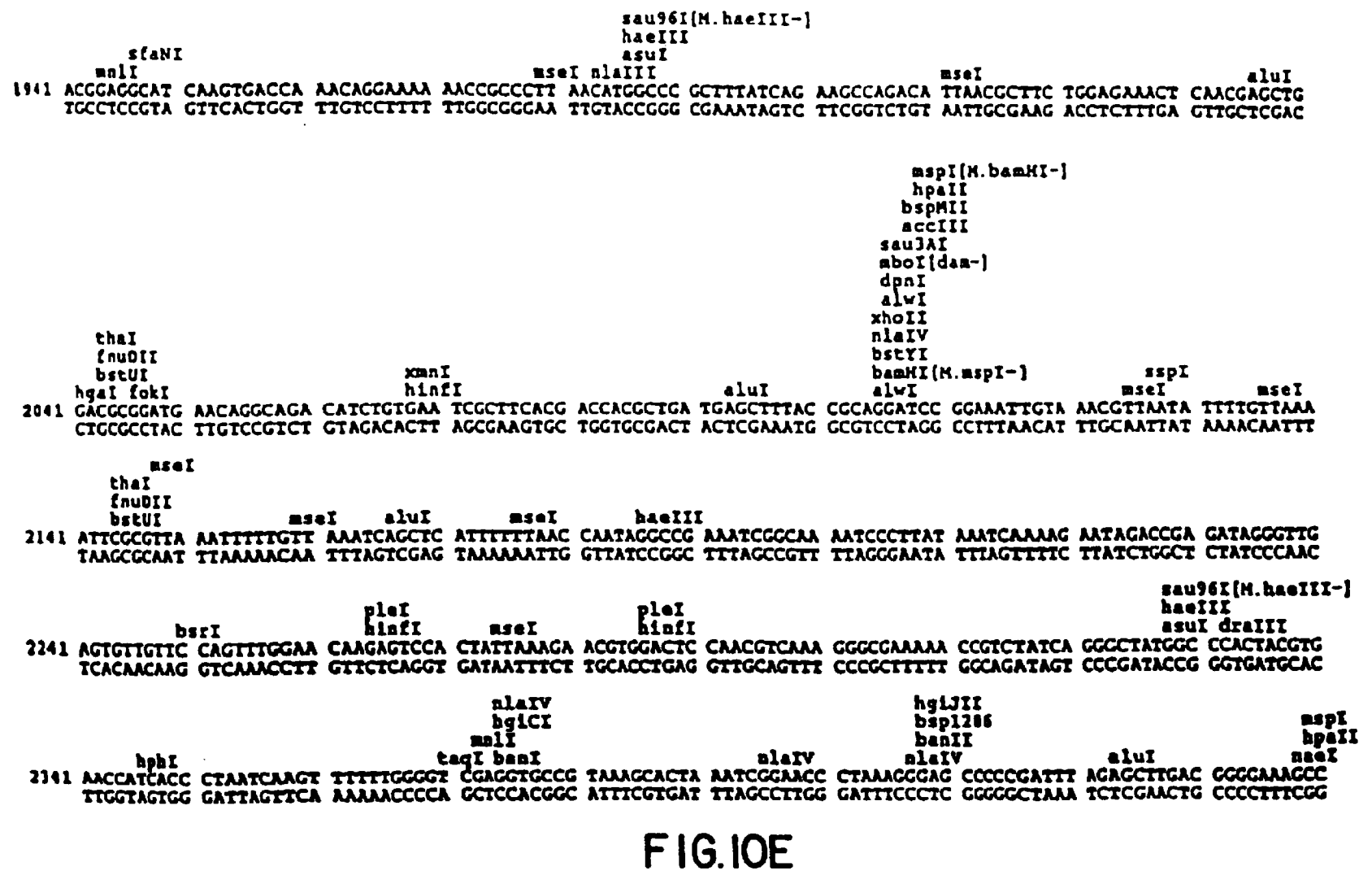
Figure 10F:
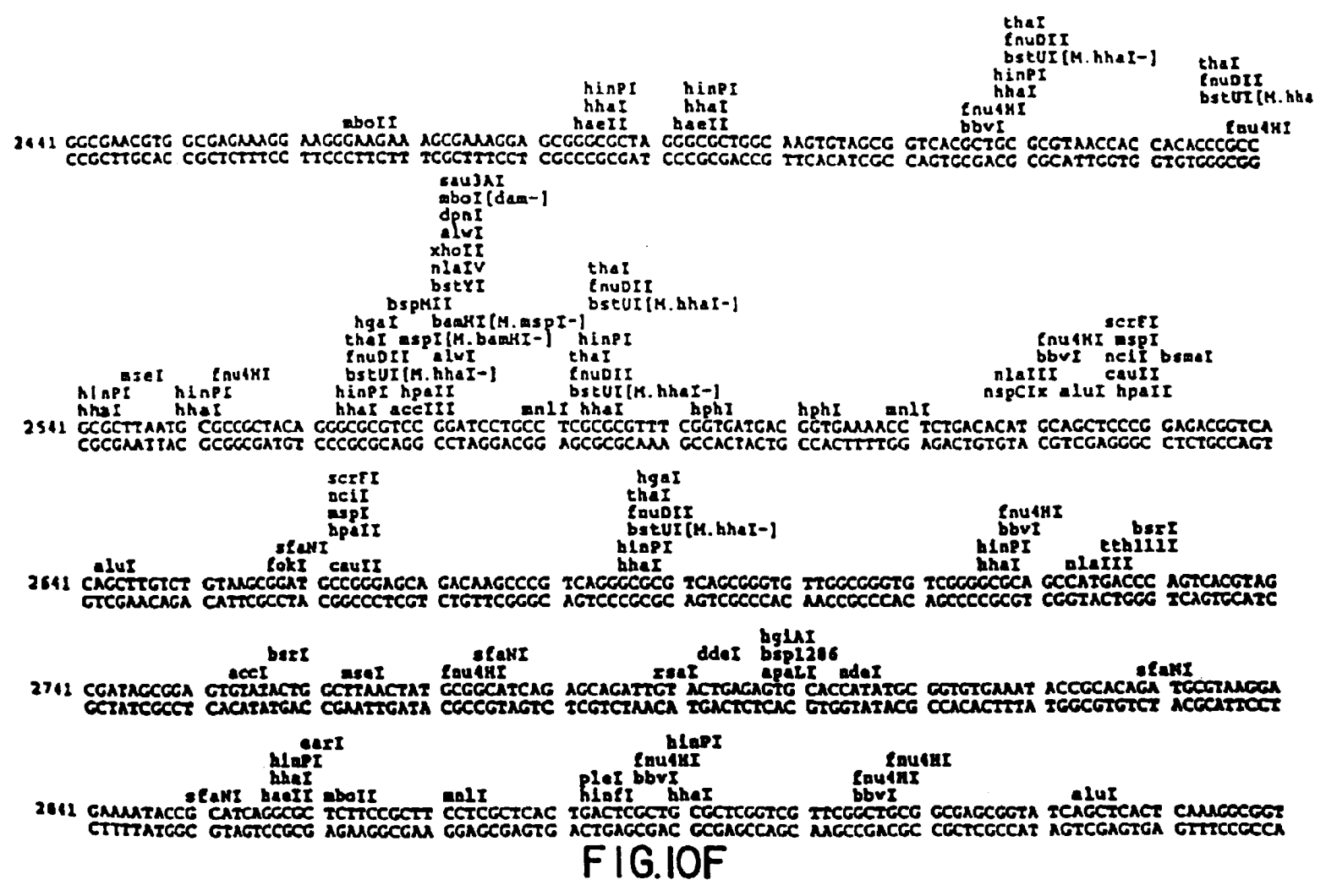
Figure 10G:
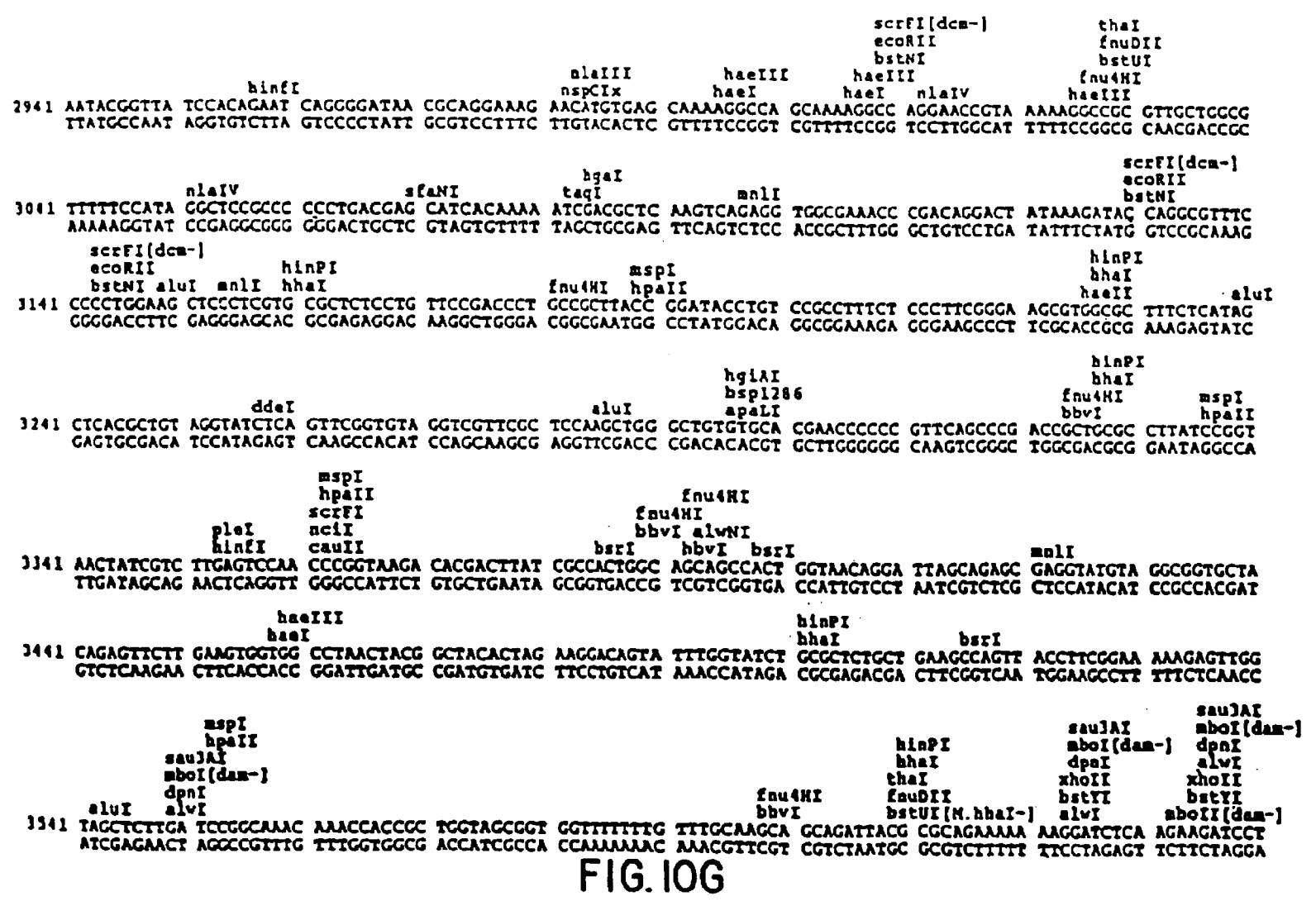
Figure 10H:
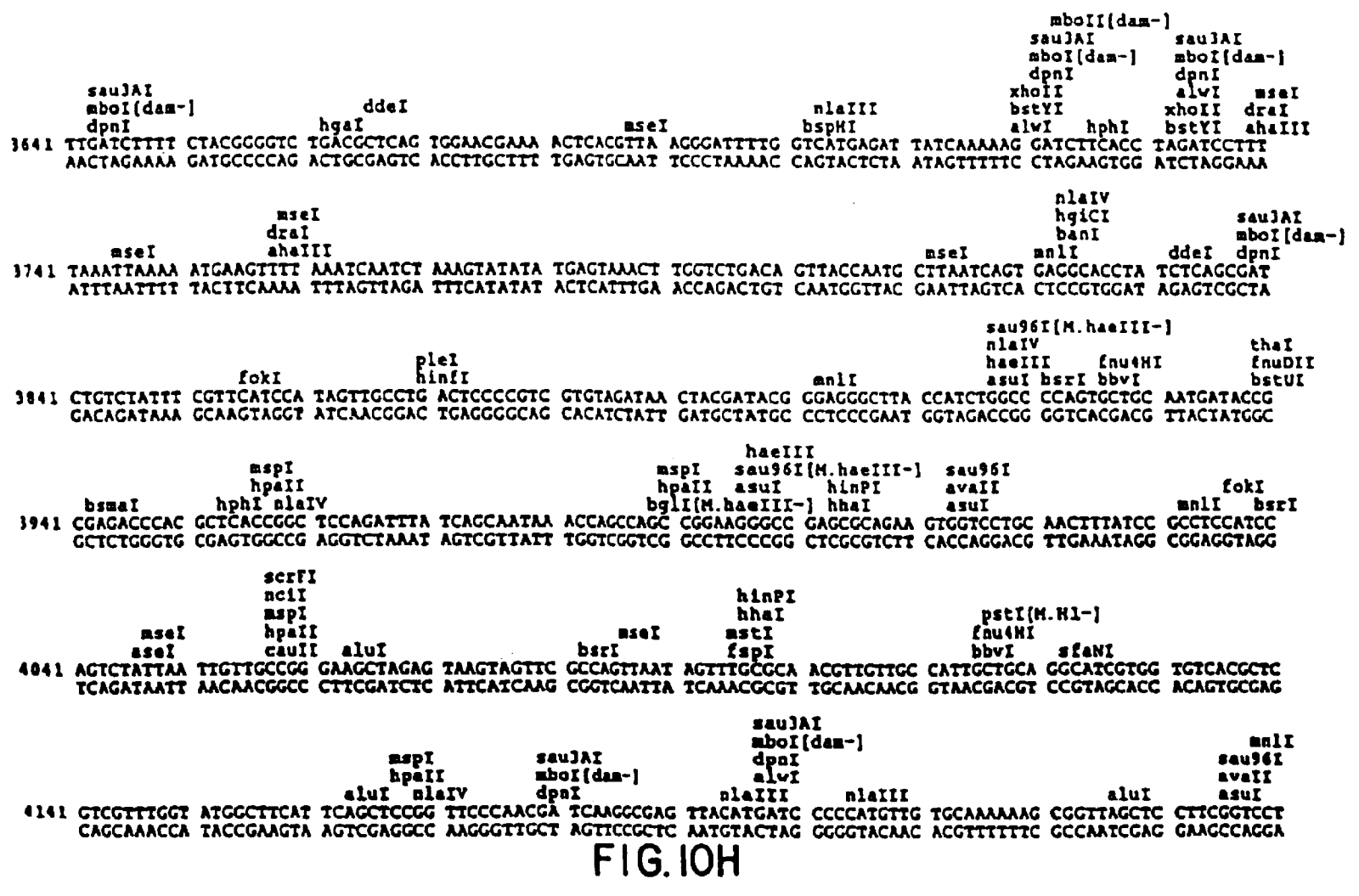
Figure 10I:
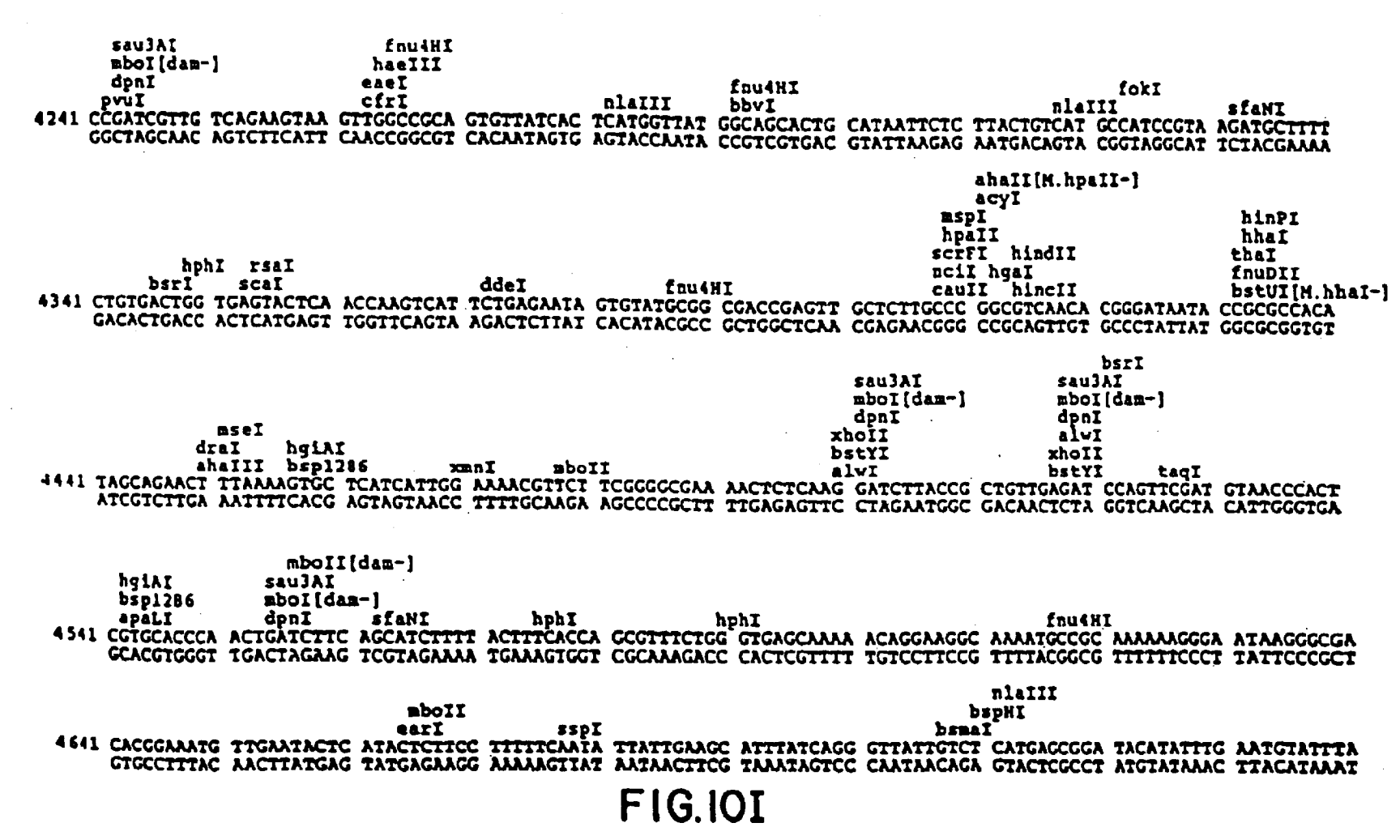

FIG. 10 is the DNA sequence of pB0475 showing the amino acid sequence for hGH.

FIG. 12 is the DNA sequence for pJ1446 showing the amino acid sequence for the soluble portion of the somatogenic receptor from liver.

FIG. 25. Structural model of hGH based on a folding diagram for pGH determined from a 2.8 Å resolution X-ray structure. Panel A shows a functional contour map of the hGH receptor epitope and Panel B shows that determined here for the hPRL receptor epitope. The size of the closed circles corresponds to the magnitude of the disruptive effect for alanine substitution at these residues. The small circles represent >2-fold disruption whereas the larger circles represent >10-fold disruption. The ▲ in the hGH receptor epitope (Panel A) represents the position of E174A that causes greater than a four-fold increase in binding affinity.

FIG. 26. Plasmid diagram of pBO760 used for intracellular expression of hPRL in E. coli.

FIG. 28. Circular dichroic spectra in the far UV (Panel A) or near UV (Panel B) of hGH (-), wild-type hPRL (- -) and hPRL variant D ( - - - ) (see Table XXIII).

FIG. 29. Sequence comparison of hGH and HPRL in regions defined by homolog and alanine scanning mutagenesis to be important for binding. Identical residues are shaded and the numbering is based on the hGH sequence. Residues are circled that when mutated cause more than a 4-fold change in binding affinity. Asterisks above residues indicate sites at which mutations cause a 2- to 4-fold reduction in binding affinity.

DETAILED DESCRIPTION OF THE INVENTION

Figure 1:
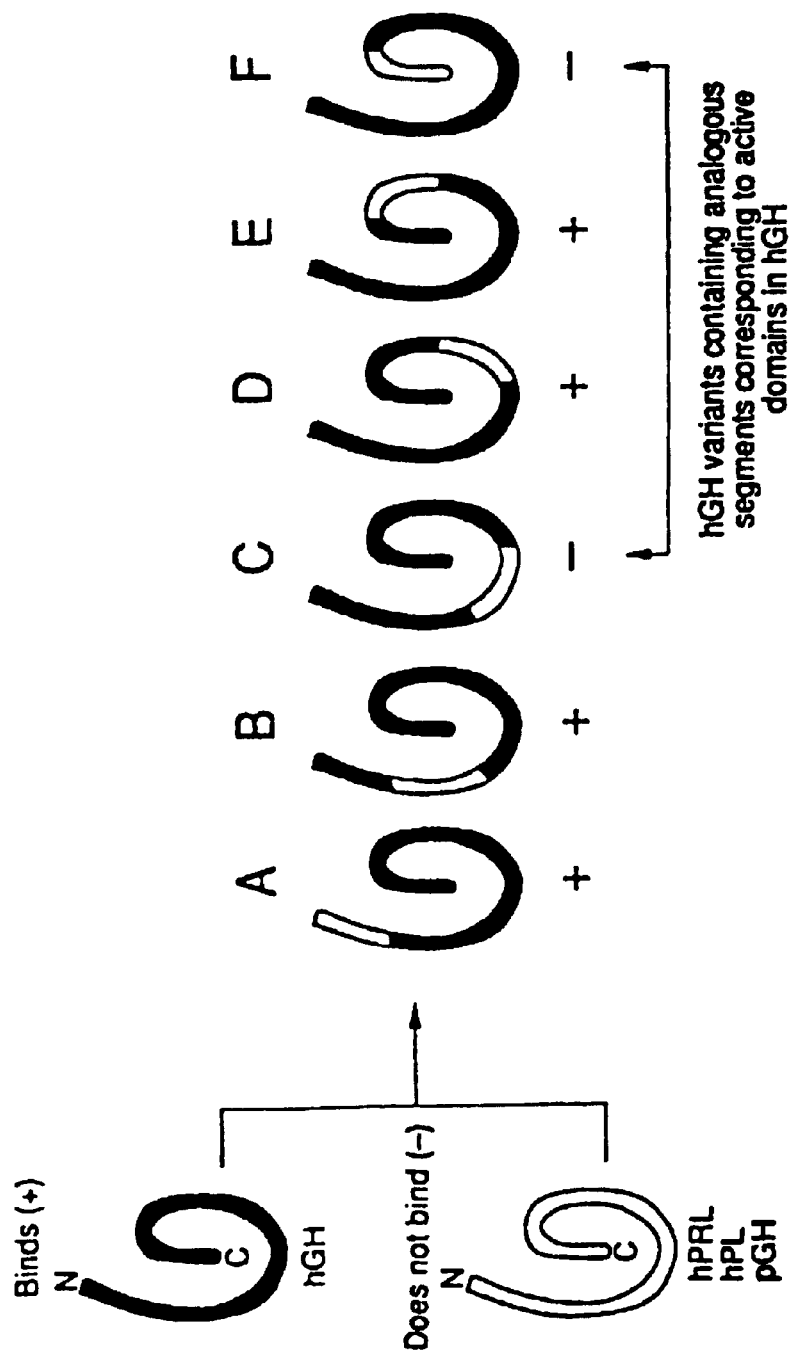
FIG. 1 depicts the strategy used to identify active domains.

In one embodiment, the method of the invention provides for the systematic analysis of a parent polypeptide, such as human growth hormone or human prolactin, to determine one or more active domains in the polypeptide that are involved in the interaction of the parent polypeptide with a target substance. To employ the method of the invention, one or more analogs to the polypeptide of interest must exist which exhibit a different activity with the target substance of interest.

Accordingly; as used herein, "parent polypeptide" refers to any polypeptide for which an "analog" exists that has a different activity with a target substance as compared to the same activity for the parent polypeptide. Examples of such polypeptides, analogs and target substances are shown in Table I.

TABLE I

| Parent Polypeptide | Analog | Target or Assay Containing Target |
|---|---|---|
| Human growth hormone | Human placental lactogen, human prolactin and porcine growth hormone | Receptors for somatogenic, lactogenic, diabetagenic, lipolytic, nitrogen retention, macrophage activation and insulin-like effects of hGH; rat tibia assay, rat weight gain assay, insulin resistance assay in OB/OB mice or dog, receptors on human liver, adipose, lymphocytes, thymocytes and ovary tissue |
| hPRL | pGH | Binding to human prolactin receptor |
| Rabbit GH receptor | Human GH receptor | Binding to rabbit GH |
| α-interferon | Related human interferons and animal interferons | Binding to $\alpha_1$ interferon receptor |
| human tissue growth factor ($TGF-\beta_1$) | human $TGF-\beta_2$ or inhibins | Human hemopoietic cell growth modulation |
| Epidermal growth factor (EGF) | TGF-α | Carotinocyte proliferation |
| Mouse Tumor Necrosis Factor (mTNF) | Human Tumor Necrosis Factor (hTNF) | Mouse TNF receptor activity |
| human granulocyte macrophage colony stimulating factor (hGMCSF) | mouse granulocyte macrophage colony stimulating factor (mGMCSF) | Growth and differentiation of human bone marrow stem cells |
| human CD-4 receptor | mouse CD-4 receptor | gp-120 from HIV virus |
| Subtilisin *Bacillus Amylilquifaciens* | Subtilisin *Bacillus licheniformis* | succinyl-ala-ala-pro-glu-P-Nitroanilyd |
| human γ-interferon | Related human interferons and animal interferons, e.g., from mouse | Activation of human interferon receptor |
| Insulin-like growth factor (IGF-1) | Insulin | IGF-1 receptor growth growth modulation receptor |
| Tissue Plasminogen Activator (tPA) | Trypsin, urokinase | Plasminogen (cleavage) fibrin (binding) |

The parent polypeptides, analogs and target substances in Table I, of course, are exemplary only.

Parent polypeptides also include proteinaceous material comprising one or more subunits, e.g. succinyl coenzyme A synthetase, mitochondrial ATPase, aminoacyl tRNA synthetase, glutamine synthetase, glyceraldehyde-3-phosphate dehydrogenase and aspartate transcarbamolase (see, Huang, et al. (1982), *Ann. Rev. Biochem,* 51, 935–971). In such multi-subunit parent polypeptides, active domains may span the two or more subunits of the parent polypeptide. Accordingly, the methods as described in more detail hereinafter can be used to probe each of the subunits of a particular polypeptide to ascertain the active domain and active amino acid residues for a particular target which may be partially contained on one subunit and partially on one or more other subunits.

The parental polypeptide and analog typically belong to a family of polypeptides which have related functions. Moreover, such parental polypeptides and analogs ordinarily will have some amino acid sequence identity, i.e., conserved residues. Such sequence homology may be as high as 90% but may range as low as about 15% to 20%.

In addition to primary sequence homology, an analog to a parent polypeptide may be defined by the three-dimensional framework of the polypeptide and analog. Thus, an analog may be divergent from a parent polypeptide in amino acid sequence but structurally homologous to the parent polypeptide based on a comparison of all, or part, of the tertiary structure of the molecules. Chothia, C., et al. (1986) *Embo. J.* 5, 823.

In general, tertiary analogs can be identified if the three-dimensional structure of a possible analog is known together with that of the parent polypeptide. By performing a root means squared differences (RMS) analysis of the α-carbon coordinates, (e.g., Sutcliffe, M. J., et al. (1987) *Protein Engineering* 1, 377–384), the superposition of regions having tertiary analog y, if any, are identified. If the α-carbon coordinates overlap or are within about 2 Å to about 3.5 Å RMS for preferably about 60% or more of the sequence of the test analog relative to the α-carbon coordinates for the parent polypeptide, the test analog is a tertiary analog to the parent polypeptide. This, of course, would exclude any insertions or deletions which may exist between the two sequences.

Although the above parent polypeptide and analogs disclose naturally occurring molecules, it is to be understood that parent polypeptides and analogs may comprise variants of such sequences including naturally occurring variants and variations in such sequences introduced by in vitro recombinant methods. Variants used as parent polypeptides or analogs thus may comprise variants containing the substitution, insertion and/or deletion of one or more amino acid residues in the parent polypeptide or analog. Such variants may be used in practicing the methods of the invention to identify active domains and/or amino acids or to prepare the polypeptide variants of the invention. Thus, the naturally occurring variants of hGH or the recombinantly produced variant containing the substitution of Cys-165 with Ala may be used as parent polypeptide or an analog so long as they have some activity with a target. Such naturally occurring and recombinantly produced variants may contain different amino acid residues which are equivalent to specific residues in another parent polypeptide. Such different amino acids are equivalent if such residues are structurally analogous by way of primary sequence or tertiary structure or if they are functionally equivalent.

Further, it should be apparent that many of the parent polypeptides and analogs can exchange roles. Thus, non-human growth hormones and their related family of analogs each can be used as a parent polypeptide and homolog to probe for active domains. Further, targets such as the CD-4 receptor for the HIV virus, may be used as a parent polypeptide with analog CD-4 receptors to identify active domains and amino acids responsible for binding HIV and to make CD-4 variants.

As used herein, a "target" is a substance which interacts with a parent polypeptide. Targets include receptors for proteinaceous hormones, substrates for enzymes, hormones for proteinaceous receptors, generally any ligand for a proteinaceous binding protein and immune systems which may be exposed to the polypeptides. Examples of hormone receptors include the somatogenic and lactogenic receptors for hGH and the receptor for hPRL. Other targets include antibodies, inhibitors of proteases, hormones that bind to proteinaceous receptors and fibrin which binds to tissue plasminogen activators (t-PA).

Generally, targets interact with parent polypeptides by contacting an "active domain" on the parent polypeptide. Such active domains are typically on the surface of the polypeptide or are brought to the surface of the polypeptide by way of conformational change in tertiary structure. The surface of a polypeptide is defined in terms of the native folded form of the polypeptide which exists under relevant physiological conditions, i.e. in vivo or under similar conditions when expressed in vitro. The amino acid segments and amino acid residues may be ascertained in several ways. If the three dimensional crystal structure is known to sufficient resolution, the amino acid residues comprising the surface of the polypeptide are those which are "surface accessible". Such surface accessible residues include those which contact a theoretical water molecule "rolled" over the surface of the three dimensional structure.

The active domain on the surface of the polypeptide may comprise a single discrete segment of the primary amino acid sequence of the polypeptide. In many instances, however, the active domain of a native folded form of a polypeptide comprises two or more discontinuous amino acid segments in the primary amino acid sequence of the parent polypeptide. For example, the active domain for human growth hormone with the somatogenic receptor is shown in FIG. 5. As indicated, domain A, C and F of the active domain are each located on discontinuous amino acid segments of the hGH molecule. These amino acid segments are identified in FIG. 4 by the letters A, C and F. Discontinuous amino acid segments which form an active domain are separated by a number of amino acid residues which are not significantly involved in the interaction between the active domain and the target. Typically, the separation between discontinuous amino acid segments is usually at least about five amino acids.

The methods of the invention are directed to the detection of unknown active domains in the amino acid sequence of a parent polypeptide. Except for those few cases where a three dimensional crystal structure of a polypeptide with its target are available, e.g. the crystal structure of enzymes with inhibitors or transition state analogs, most active domains for a vast array of polypeptides remain unknown.

As used herein an "analogous polypeptide segment" or "analogous segment" refers to an amino acid sequence in an analog which is substituted for the corresponding sequence in a parent polypeptide to form a "segment-substituted polypeptide". Analogous segments typically have a sequence which results in the substitution, insertion or deletion of one or more different amino acid residues in the parent polypeptide while maintaining the relative amino acid sequence of the other residues in the selected segment substituted in the parent. In general, analogous segments are identified by aligning the overall amino acid sequence of the parent polypeptide and analog to maximize sequence identity between them. Analogous segments based on this sequence alignment are chosen for substitution into the corresponding sequence of the parent polypeptide. Similarly, analogous segments from analogs showing tertiary homology can be deduced from those regions showing structural homology. Such analogous segments are substituted for the corresponding sequences in the parent. In addition, other regions in such tertiary homologs, e.g., regions flanking the structurally analogous region, may be used as analogous segments.

The analogous segment should be selected, if possible, to avoid the introduction of destabilizing amino acid residues into the segment-substituted polypeptide. Such substitutions include those which introduce bulkier side chains, and hydrophilic side chains in hydrophobic core regions.

Typically, the amino acid sequences of the parent polypeptide and analog are known and in some cases three-dimensional crystal structures may be available. An alignment of the amino acid sequence of the parent polypeptide with that of one or more analogs readily reveals conserved amino acid residues in the sequences which should not be altered, at least in the preliminary analysis. Sequence alignment will also reveal regions of sequence variation which may include the substitution, insertion or deletion of one or more amino acid residues. Those regions containing such variations determine which segments in the parent may be substituted with an analogous segment. The substitution of an analogous segment from an analog may therefore result not only in the substitution of amino acid residues but also in the insertion and/or deletion of amino acid residues.

If three-dimensional structural information is available, it is possible to identity regions in the parent polypeptide which should not be subjected to substitution with an analogous segment. Thus, for example, the identification of a tightly packed region in a hydrophobic face of an amphiphilic helix in the parent polypeptide should not be substituted with an analogous segment. Residues identified as such should be retained in the polypeptide variant and only surface residues substituted with analogous residues.

Generally, analogous segments are 3 to 30 amino acid residues in length, preferably about 3 to 15 and most preferably about 10 to 15 amino acid residues in length. In some instances, the preferred length of the analogous segment may be attenuated because of the insertion and/or deletion of one or more amino acid residues in the analogous segment as compared to the homolog or parent polypeptide. If a three-dimensional structure is unavailable for the parent polypeptide, it is generally necessary to form segment-substituted polypeptides with analogous segments covering most, if not all, of the parent polypeptide. Segment-substitution of the entire amino acid sequence, however, is not always necessary. For example, fortuitous segment-substitutions covering only a portion of the total amino acid sequence may provide sufficient information to identify the active domain for a particular target. Thus, for example, the segment-substitution of about 15% of the amino acid sequence of the parent polypeptide may provide sufficient indication of the active domain. In most instances, however, substantially more than about 15% of the amino acid sequence will need to be segment-substituted to ascertain the active domain. Generally, about 50%, preferably about 60%, more preferably about 75% and most preferably 100% of the amino acid sequence will be segment-substituted if no structural information is available.

As used herein, "analogous amino acid residue" or "analogous residue" refers to an amino acid residue in an analogous segment which is different from the corresponding amino acid residue in the corresponding segment of a parent polypeptide. Thus, if the substitution of an analogous segment results in the substitution of one amino acid, that amino acid residue is an analogous residue.

Once the parent polypeptide and one or more analogs are identified, the analogous segments from one or more of the analogs are substituted for selected segments in the parent polypeptide to produce a plurality of segment-substituted polypeptides. Such substitution is conveniently performed using recombinant DNA technology. In general, the DNA sequence encoding the parent polypeptide is cloned and manipulated so that it may be expressed in a convenient host. DNA encoding parent polypeptides can be obtained from a genomic library, from cDNA derived from mRNA from cells expressing the parent polypeptide or by synthetically constructing the DNA sequence (Maniatis, T., et al. (1982) in *Molecular Cloning,* Cold Springs Harbor Laboratory, N.Y.).

The parent DNA is then inserted into an appropriate plasmid or vector which is used to transform a host cell. Prokaryotes are preferred for cloning and expressing DNA sequences to produce parent polypeptides, segment substituted polypeptides, residue-substituted polypeptides and polypeptide variants. For example, *E. coli* K12 strain 294 (ATCC No. 31446) may be used as well as *E. coli* B, *E. coli* X1776 (ATCC No. 31537), and *E. coli* c600 and c600hfl, *E. coli* W3110 (F-, γ-, prototrophic, ATCC No. 27325), bacilli such as *Bacillus subtilis,* and other enterobacteriaceae such as *Salmonella typhimurium* or *Serratia marcesans,* and various pseudomonas species. The preferred prokaryote is *E. coli* W3110 (ATCC 27325). When expressed in prokaryotes the polypeptides typically contain an N-terminal methionine or a formyl methionine, and are not glycosylated. These examples are, of course, intended to be illustrative rather than limiting.

In addition to prokaryotes, eukaryotic organisms, such as yeast cultures, or cells derived from multicellular organisms may be used. In principle, any such cell culture is workable. However, interest has been greatest in vertebrate cells, and propagation of vertebrate cells in culture (tissue culture) has become a repeatable procedure (*Tissue Culture,* Academic Press, Kruse and Patterson, editors (1973)). Examples of such useful host cell lines are VERO and HeLa cells, Chinese Hamster Ovary (CHO) cell lines, W138, BHK, COS-7 and MDCK cell lines.

In general, plasmid vectors containing replication and control sequences which are derived from species compatible with the host cell are used in connection with these hosts. The vector ordinarily carries a replication site, as well as sequences which encode proteins that are capable of providing phenotypic selection in transformed cells. For example, *E. coli* may be transformed using pBR322, a plasmid derived from an *E. coli* species (Mandel, M. et al. (1970) *J. Mol. Biol.* 53, 154). Plasmid pBR322 contains genes for ampicillin and tetracycline resistance and thus provides easy means for selection. A preferred vector is pB0475. See Example 1. This vector contains origins of replication for phage and *E. coli* which allow it to be shuttled between such hosts thereby facilitating mutagenesis and expression.

"Expression vector" refers to a DNA construct containing a DNA sequence which is operably linked to a suitable control sequence capable of effecting the expression of said DNA in a suitable host. Such control sequences include a promoter to effect transcription, an optional operator sequence to control such transcription, a sequence encoding suitable mRNA ribosome binding sites, and sequences which control termination of transcription and translation. The vector may be a plasmid, a phage particle, or simply a potential genomic insert. Once transformed into a suitable host, the vector may replicate and function independently of the host genome, or may, in some instances integrate into the genome itself. In the present specification, "plasmid" and "vector" are sometimes used interchangeably as the plasmid is the most commonly used form of vector at present. However, the invention is intended to include such other forms of expression vectors which serve equivalent functions and which are, or become, known in the art.

"Operably linked" when describing the relationship between two DNA or polypeptide regions simply means that they are functionally related to each other. For example, a presequence is operably linked to a peptide if it functions as a signal sequence, participating in the secretion of the mature form of the protein most probably involving cleavage of the signal sequence. A promoter is operably linked to a coding sequence if it controls the transcription of the sequence; a ribosome binding site is operably linked to a coding sequence if it is positioned so as to permit translation.

Once the parent polypeptide is cloned, site specific mutagenesis (Carter, P., et al. (1986) *Nucl. Acids Res.* 13, 4331; Zoller, M. J., et al. (1982) *Nucl. Acids Res.* 10, 6487), cassette mutagenesis (Wells, J. A., et al. (1985) *Gene* 34, 315), restriction selection mutagenesis (Wells, J. A., et al. (1986) *Philos. Trans. R. Soc. London SerA* 317, 415) or other known techniques may be performed on the cloned parent DNA to produce "segment-substituted DNA sequences" which encode the changes in amino acid sequence defined by the analogous segment being substituted. When operably linked to an appropriate expression vector, segment-substituted polypeptides are obtained. In some cases, recovery of the parent polypeptide or segment-modified polypeptide may be facilitated by expressing and secreting such molecules from the expression host by use of an appropriate signal sequence operably linked to the DNA sequence encoding the parent polypeptide or segment-modified polypeptide. Such methods are well-known to those skilled in the art. Of course, other methods may be employed to produce such polypeptides and segment-substituted polypeptides such as the in vitro chemical synthesis of the desired polypeptide (Barany, G., et al. (1979) in *The Peptides* (eds. E. Gross and J. Meienhofer) Acad. Press, N.Y., Vol. 2, pp. 3–254).

Once the different segment-substituted polypeptides are produced, they are contacted with a target for the parent polypeptide and the interaction, if any, of the target and each of the segment-substituted polypeptides is determined. These activities are compared to the activity of the parent polypeptide with the same target. If the analog has a substantially altered activity with the target as compared to the parent polypeptide, those segment-substituted polypeptides which have altered activity with the target presumptively contain analogous segments which define the active domain in the parent polypeptide.

If the analog has an activity with the target which is greater than that of the parent polypeptide, one or more of the segment-substituted polypeptides may demonstrate an increased activity with that target substance. Such a result would, in effect, identify an active domain in the analog and an appropriate region in the parent polypeptide which can be modified to enhance its activity with that target substance. Such an event is most likely when the region in the analog responsible for the target interaction is contained primarily within one continuous amino acid segment. If the "active domains" of the analog comprise discontinuous regions in the amino acid sequence of the analog, enhanced activity in the segment-substituted polypeptide is less likely since the demonstration of such enhanced activity may require the simultaneous introduction of all active domains from the analog into the segment-substituted polypeptide.

Accordingly, it is preferred that the analog have an activity with the target which is less than that for the parent-polypeptide. In this manner, a loss in activity is observed in the segment-substituted polypeptide. However, once the active domains in a parent polypeptide are determined, that polypeptide may be used as an analog to sequentially or simultaneously substitute such active domains into a second parent polypeptide which lacks activity with the target for the first parent polypeptide.

Active domains in polypeptides are identified by comparing the activity of the segment-substituted polypeptide with a target with the activity of the parent polypeptide. Any number of analytical measurements may be used but a convenient one for non-catalytic binding of target is the dissociation constant Kd of the complex formed between the segment-substituted polypeptide and target as compared to the Kd for the parent. An increase or decrease in Kd of about 1.5 and preferably about 2.0 per analogous residue substituted by the segment-substitution indicates that the segment substituted is an active domain in the interaction of the parent polypeptide with the target.

In the case of catalytic interaction with a target, a suitable parameter to measure activity relative to the parent enzyme is to compare the ratios of kcat/Km. An increase or decrease in kcat/Km relative to the parent enzyme of about 1.5 and preferably 2.0 per analogous residue-substituted indicates that an active domain has been substituted.

As used herein, a "scanning amino acid" is an amino acid used to identify active amino acids within a parent polypeptide. A "residue-substituted polypeptide" is a polypeptide variant containing at least a single substitution of an amino acid in the parent polypeptide with a scanning amino acid. A "residue-substituted DNA sequence" encodes a residue substituted polypeptide. Such DNA and polypeptide sequences may be prepared as described for the preparation of segment-substituted DNA and polypeptides.

The "active amino acid residue" identified by the amino acid scan is typically one that contacts the target directly. However, active amino acids may also indirectly contact the target through salt bridges formed with other residues or small molecules such as $H_2O$ or ionic species such as $Na^+$, $Ca^{+2}$, $Mg^{+2}$ or $Zn^{+2}$.

In some cases, the scanning amino acid is substituted for an amino acid identified in an active domain of the parent polypeptide. Typically, a plurality of residue-substituted polypeptides are prepared, each containing the single substitution of the scanning amino acid at a different amino acid residue within the active domain. The activities of such residue-substituted polypeptides with a particular target substance are compared to the activity of the parent polypeptide to determine which of the amino acid residues in the active domain are involved in the interaction with the target substance. The scanning amino acid used in such an analysis may be any different amino acid from that substituted, i.e., any of the 19 other naturally occurring amino acids.

TABLE II

| Polypeptide Amino Acid | Isosteric scanning Amino Acid |
|---|---|
| Ala | Ser, Gly |
| Glu | Gln, Asp |
| Gln | Asn, Glu |
| Asp | Asn, Glu |
| Asn | Aln, Asp |

TABLE II-continued

| Polypeptide Amino Acid | Isosteric scanning Amino Acid |
|---|---|
| Leu | Met, Ile |
| Gly | Pro, Ala |
| Lys | Met, Arg |
| Ser | Thr, Ala |
| Val | Ile, Thr |
| Arg | Lys, Met, Asn |
| Thr | Ser, Val |
| Pro | Gly |
| Ile | Met, Leu, Val |
| Met | Ile, Leu |
| Phe | Tyr |
| Tyr | Phe |
| Cys | Ser, Ala |
| Trp | Phe |
| His | Asn, Gln |

This table uses the following symbols for each amino acid:

| Amino Acid or residue thereof | 3-letter symbol | 1-letter symbol |
|---|---|---|
| Alanine | Ala | A |
| Glutamate | Glu | E |
| Glutamine | Gln | Q |
| Aspartate | Asp | D |
| Asparagine | Asn | N |
| Leucine | Leu | L |
| Glycine | Gly | G |
| Lysine | Lys | K |
| Serine | Ser | S |
| Valine | Val | V |
| Arginine | Arg | R |
| Threonine | Thr | T |
| Proline | Pro | P |
| Isoleucine | Ile | I |
| Methionine | Met | M |
| Phenylalanine | Phe | F |
| Tyrosine | Tyr | Y |
| Cysteine | Cys | C |
| Tryptophan | Trp | W |
| Histidine | His | H |

Most preferably, the scanning amino acid is the same for each residue substituted polypeptide so that the effect, if any, on the activity of the residue-substituted polypeptides can be systematically attributed to the change from the naturally occurring amino acid residue to a uniform scanning amino acid residue.

In some cases, the substitution of a scanning amino acid at one or more residues results in a residue-substituted polypeptide which is not expressed at levels which allow for the isolation of quantities sufficient to carry out analysis of its activity with a target. In such cases, a different scanning amino acid, preferably an isosteric amino acid, can be used.

The most preferred scanning amino acids are relatively small, neutral amino acids. Such amino acids include alanine, glycine, serine and cysteine. Alanine is the preferred scanning amino acid among this group because it eliminates the side-chain beyond the beta-carbon and is less likely to alter the main-chain conformation of the residue-substituted polypeptide. Alanine is also preferred because it is the most common amino acid. Further, it is frequently found in both buried and exposed positions (Creighton, T. E., in *The Proteins* (eds. W.H. Freeman & Co., N.Y.); Chothia, C.

(1976) *J. Mol. Biol.* 150, 1). If alanine substitution does not yield adequate amounts of residue-substituted polypeptide, an isosteric amino acid can be used. Alternatively, the following amino acids in decreasing order of preference may be used: Ser, Asn and Leu.

The use of scanning amino acids is not limited to the identification of active amino acids in an active domain ascertained by the analysis of segment-substituted polypeptides. If, for example, one or more amino acids in a parent polypeptide are known or suspected to be involved in the interaction with a target, scanning amino acid analysis may be used to probe that residue and the amino acid residues surrounding it. Moreover, if the parent polypeptide is a small peptide, e.g., about 3 to 50 amino acid residues, scanning amino acid analysis may be carried out over the entire molecule.

Once the active amino acid residues are identified, isosteric amino acids may be substituted. Such isosteric substitutions need not occur in all instances and may be performed before any active amino acid is identified. Such isosteric amino acid substitution is performed to minimize the potential disruptive effects on conformation that some substitutions can cause. Isosteric amino acids are shown in Table II.

Active amino acid residues can be identified by determining the activity of the residue-substituted polypeptide with a target as compared to the parent. In general, a two-fold increase or decrease in Kd indicates that the residue substituted is active in the interaction with the target. Similarly, in the case of catalytic interaction with a target, a two-fold increase or decrease in kcat/Km relative to the parent enzyme indicates that an active residue has been substituted.

When a suspected or known active amino acid residue is subjected to scanning amino acid analysis the amino acid residues immediately adjacent thereto should be scanned. Three residue-substituted polypeptides are made. One contains a scanning amino acid, preferably alanine, at position N which is the suspected or known active amino acid. The two others contain the scanning amino acid at position N+1 and N−1. If each substituted polypeptide causes a greater than about two-fold effect on Kd or kcat/Km for a target, the scanning amino acid is substituted at position N+2 and N−2. This is repeated until at least one and preferably four residues are identified in each direction which have less than about a two-fold effect on Kd or kcat/Km or either of the ends of the parent polypeptide are reached. In this manner, one or more amino acids along a continuous amino acid sequence which are involved in the interaction with a particular target can be identified.

The methods of the invention may be used to detect the active domain for more than one target of a particular parent polypeptide. Further, active amino acid residues within the different active domains may be also identified by the methods herein. Once two or more active domains and active amino acid residues are identified for the different targets of a particular polypeptide, various modifications to the parent polypeptide may be made to modify the interaction between the parent polypeptide and one or more of the targets. For example, two active domains on the surface of hGH have been identified for the somatogenic and prolactin receptor. In this particular case, the active domains overlap. Accordingly, there are a number of common active amino acid residues which interact with the somatogenic and prolactin receptors. Various modifications to hGH may be made based on this information as described in more detail hereinafter.

In some instances, the active domain for different targets will not overlap. In such situations, the active amino acids in the parent polypeptide for one receptor can be substituted with different amino acids to reduce or enhance the interaction of that active domain with its target, thus shifting the physiological effect of such a variant.

As used herein, the term "modified interaction" refers to a polypeptide variant wherein one or more active domains have been modified to change the interaction of the variant with a target as compared to the parent polypeptide. A modified interaction is defined as at least a two-fold increase or decrease in the interaction of the polypeptide variant as compared to the interaction between the parent polypeptide and a particular target.

The interaction between a target and a parent polypeptide, polypeptide variant, segment-substituted polypeptide and/or residue-substituted polypeptide can be measured by any convenient in vitro or in vivo assay. Thus, in vitro assays may be used to determine any detectable interaction between a target and polypeptide, e.g. between enzyme and substrate, between hormone and hormone receptor, between antibody and antigen, etc. Such detection may include the measurement of colorimetric changes, changes in radioactivity, changes in solubility, changes in molecular weight as measured by gel electrophoresis and/or gel exclusion methods, etc. In vivo assays include, but are not limited to, assays to detect physiological effects, & weight gain, change in electrolyte balance, change in blood clotting time, changes in clot dissolution and the induction of antigenic response. Generally, any in vivo assay may be used so long as a variable parameter exists so as to detect a change in the interaction between the target and the polypeptide of interest.

Exemplary of the present invention is a preferred embodiment wherein the active domains and active amino acids of human growth hormone which determine its activity with its somatogenic receptor are identified. In carrying out this embodiment of the invention, human growth hormone variants, including segment-substituted and residue-substituted hGH variants, have been made or identified which have different binding interactions with the somatogenic receptor for growth hormone as compared to naturally occurring human growth hormone. At least one of these human growth hormone variants has a higher affinity for the somatogenic receptor and enhanced potency for somatogenesis in rats. Others have a decreased activity with the somatogenic receptor. Such hGH variants are useful as hGH agonists or antagonists and may have a higher potency for stimulating other receptors for human growth hormone since such variants will be freed from substantial interaction with the somatogenic receptor. Further, such variants are useful in immunoassays for hGH as an hGH standard or tracer. In one instance, a variant has been identified which has a significant decrease in reactivity with human and mouse serum containing anti-hGH polyclonal antibodies. Another has the same binding affinity for the somatogenic receptor as hGH but increased potency to stimulate growth.

The method for determining the active domains for human growth hormone which interact with its somatogenic receptor from liver is shown schematically in FIG. 1. In this approach, segments of hGH were systematically replaced with analogous sequences from analogs of hGH that are known to have greatly reduced affinities for the cloned hGH liver receptor and for monoclonal antibodies raised against hGH. Such analogs for hGH include human placental lactogen (hPL), porcine growth hormone (pGH) and human prolactin (hPRL). These analogs have binding affinities for the cloned hGH receptor that are reduced by about 100 to 10,000-fold for the somatogenic hGH, receptor (hGHr)

Figure 2:
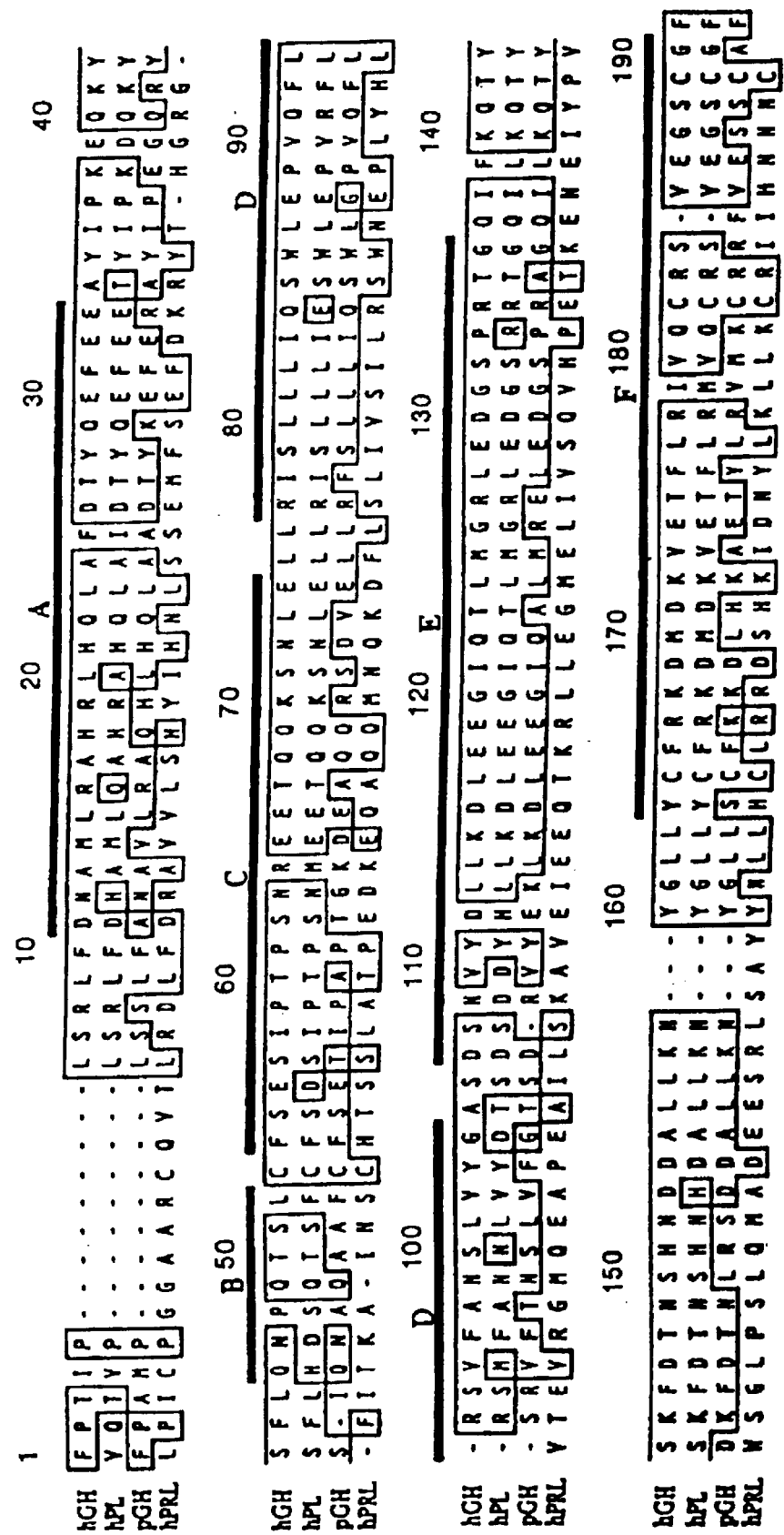
FIG. 2 shows the conserved and variable amino acid residues amongst the amino acid sequences of hGH, hPL, pGH and hPRL.

(Harrington, A. C., et al. (1986) *J. Clin. Invest.* 77, 1817; Baumann, G., et al. (1986) *J. Clin. Endocrinol. Metab.* 62, 137). Such analogs are used because homologous proteins are known to have similar three-dimensional structures even though they may have a large sequence divergence (Chothia, C., et al. (1986) *EMBO J.* 5, 823). In so doing, the likelihood is increased that analogous sequence substitutions will be readily accommodated without grossly disrupting the native folding of the molecule. The amino acid sequences for human growth hormone and the analogs hPL, pGH and hPRL are shown in FIG. 2. These latter three analogs share a sequence identity with hGH at the level of 85%, 68% and 23%, respectively.

Referring to FIG. 1, the overall strategy is shown for identifying one or more active domains in human growth hormone which interact with the somatogenic receptor for human growth hormone (a "target" for hGH). As indicated, hGH has a positive binding activity with the target receptor, in this case, the somatogenic receptor. The hPRL, hPL and pGH analogs, however, have a greatly reduced activity with that target as indicated by the minus sign. Six segment-substituted growth hormones, identified by letters A through F, are formed by substituting a selected amino acid segment of hGH with an analogous amino acid segment from the hPRL analog. Each of these selected segments are different and are chosen to probe either the entire amino acid sequence of the hGH molecule or those regions which are expected to contain the active domains. After the segment-substituted human growth hormones are prepared each is assayed against the hGH somatogenic receptor to determine its activity. The results of such an assay as compared to hGH are indicated by + or − under the segment-modified human growth hormones in FIG. 1. As can be seen in FIG. 1, segment-substituted human growth hormones C and F in this schematic do not bind the somatogenic, receptor. Based on these results, those regions in human growth hormone corresponding to the analogous segments from the analog in the growth hormone variants C and F are identified as active domains involved in the binding of hGH to its somatogenic receptor.

Figure 3:
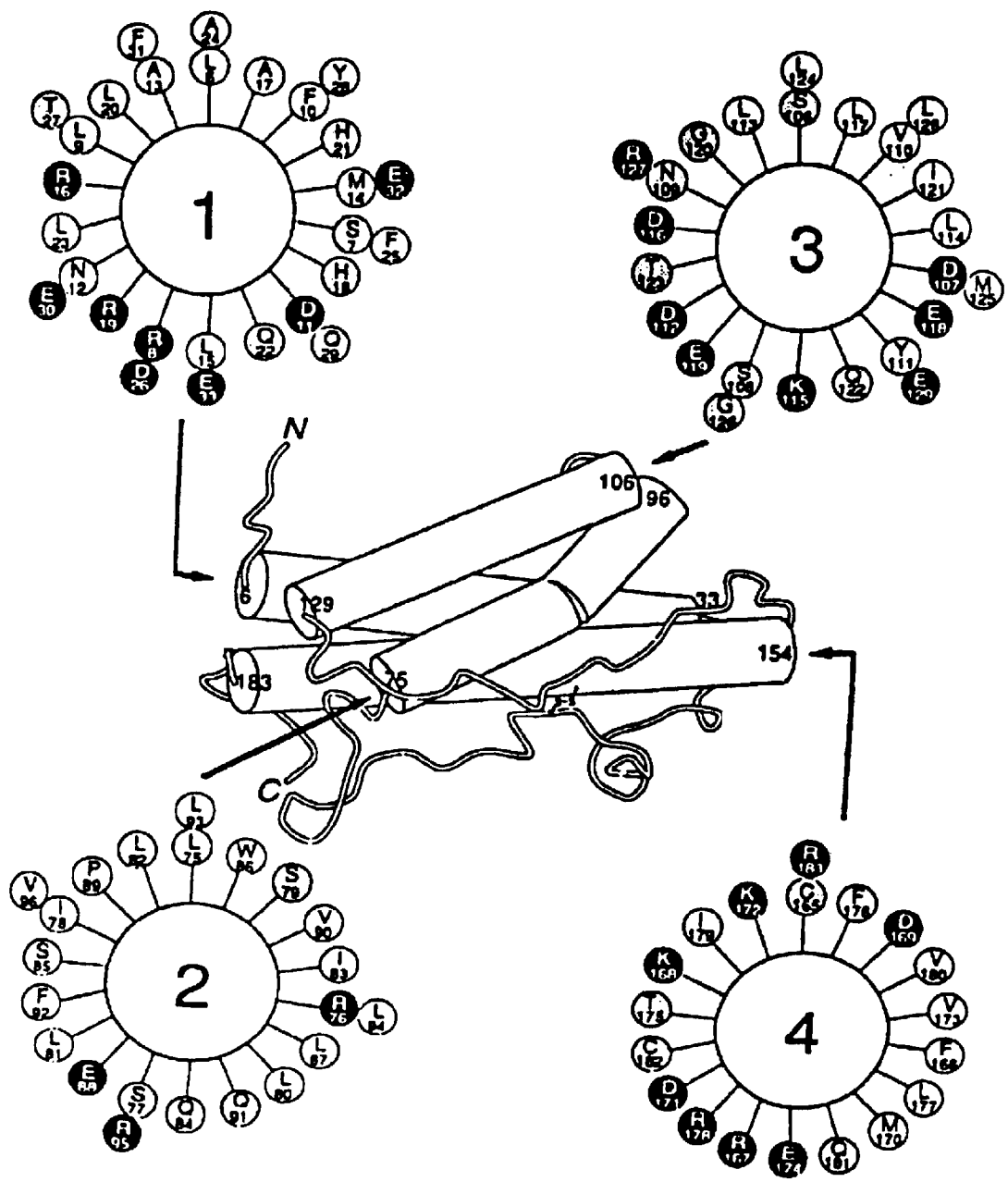
FIG. 3 shows the putative low resolution structure of hGH and helical wheel projections viewed from the N-terminal start residue for each helix. Hydrophobic, neutral and charged residues are indicated by ○, ■ and ● symbols, respectively.

As indicated, it is not necessary to probe the entire amino acid sequence of human growth hormone or other parental polypeptides if structural information or other data are available. Thus, low-resolution or high-resolution structural information from crystallographic studies can provide important information so as to avoid destabilizing substitutions of selected amino acid segments from a homolog. For example, the X-ray coordinates for human growth hormone are not available. However, helix wheel projections from the pGH folding model, based on the low resolution X-ray crystal structure of pGH, reveal that three of the four helices (helix 1, 3 and 4) are amphipathic with strong hydrophobic moments. See FIG. 3. Eisenberg, D., et al. (1984) *J. Mol. Biol.* 179, 125. Since the hydrophobic core in polypeptides is very tightly packed (Ponder, J. W., et al. (1987) *J. Mol. Biol.* 193, 775), changes in such buried amino acid residues are generally destabilizing (Alber, T., et al. (1987) *Biol. Chem.* 26, 3754; Reidhaar-Olson, J. F. (1988) *Science* 241, 53).

In addition, regions of high amino acid sequence conservation amongst members of the polypeptide family, for example the human growth hormone family, in general, need not be probed, at least initially. This is because the disruption of such conserved sequences is likely to disrupt the folding of the molecule. Further, other data may suggest that certain regions of the parent polypeptide are not involved in the interaction with a particular target substance. For example, deletion of the N-terminal 13 amino acids of hGH by mutagenesis (Ashkenazi, A., et al. (1987) *Endocrinology* 121, 414) and a natural variant of hGH which deletes residues 32 to 46 (the 20 Kd variant; Lewis, U. J., et al. (1980) *Biochem. Biophys. Res. Commun.* 92, 5111) have been reported not to affect dramatically the binding properties to the somatogenic receptor. In addition, the production of a two-chain derivative of hGH by limited proteolysis, which deletes some or all of the residues between 134 and 149, does not markedly affect binding to the somatogenic receptor. Li, C. H. (1982) *Mol. Cell. Biochem.* 46, 31; Mills, J. B., et al. (1980) *Endocrinology* 107, 391.

Based on this information, six segments of the amino acid sequence of hGH were selected for substitution with the corresponding analogous amino acid segments from a number of analogs to hGH. These selected segments are identified as A through F in FIG. 2. These segments are separated either by disulfide bonds, by borders of secondary structure (see FIG. 4), by areas of high sequence conservation in the growth hormone family or by regions previously identified as not being involved in binding to the somatogenic receptor. Seventeen segment-substituted hGH variants were prepared which collectively substituted 85 out of the 191 residues in hGH. The regions identified as A through F in FIG. 2 and the segment-substituted hGH variants prepared within each region are summarized in Table III.

TABLE III

| Region probed | Segment-Substituted hGH Variant | Actual Substitution Introduced | Mutagenesis method | $K_d$ (nM) | $K_d$ (variant)/$K_d$ (wt) |
|---|---|---|---|---|---|
| | hGH | None | | 0.34 | 1.0 |
| A 11–33 | hPL (12–25) | N12H, F25L | r.s.[1] | 1.4 | 4.1 |
| | pGH (11–33) | D11A, M14V, M18Q R19H, F25A, Q29K, E33R | cassette[2] | 1.2 | 3.4 |
| | hPRL (12–33) | N12R, M14V, L15V, R16L, R19Y, F25S, D26E, Q29S, E30Q, E33K | cassette | 3.6 | 11 |
| | hPRL (12–19) | N12R, M14V, L15V, R16L, R19Y | r.s. | 5.8 | 17 |
| | hPRL (22–33) | Q22N, F25S, D26E, Q29S, E30Q, E33K | r.s. | 0.29 | 0.85 |
| B 46–52 | hPL (46–52) | Q46H, N47D, P48S, Q49E, L52F | r.s. | 2.5 | 7.2 |

TABLE III-continued

| Region probed | Segment-Substituted hGH Variant | Actual Substitution Introduced | Mutagenesis method | $K_d$ (nM) | $\frac{K_d \text{ (variant)}}{K_d \text{ (wt)}}$ |
|---|---|---|---|---|---|
| | pGH (48–52) | P48A, T50A, S51A, L52F | r.s. | 0.94 | 2.8 |
| C 54–74 | hPL (56–64) | E56D, R64M | cassette | 10 | 30 |
| | pGH (57–73) | S57T, T60A, S62T, N63G, R64K, E65D, T67A, K70R, N72D, L73V | cassette | 5.8 | 17 |
| | hPRL (54–74) | F54H, S55T, E56S, I58L, P59A, S62E, N63D, R64K, E66Q, T67A, K70M, S71N, N72Q, L73K, E74D | cassette | 23 | 69 |
| D 88–104 | hPRL (88–95) | E88G, Q91Y, F92H, R94T, S95E | r.s. | 0.47 | 1.4 |
| | hPRL (97–104) | F97R, A98G, N99M, S100Q, L101D, V102A, Y103P, G104E | r.s. | 0.53 | 1.6 |
| E 108–136 | hPL (109–112) | N109D, V110D, D112H | cassette | 0.61 | 1.8 |
| | hPRL (111–129) | Y111V, L113I, K115E, D116Q, E118K, E119R, G120L, Q122E, T123G, G126L, R127I, E129S | cassette | 0.52 | 1.5 |
| | hPRL (126–136) | R127D, L128V, E129H, D130P, G131E, S132T, P133K, R134E, T135N | cassette | 0.58 | 1.7 |
| F 164–190 | pGH (164–190) | Y164S, R167K, M170L, D171H, V173A, F176Y, I179V, V180M, Q181K, S184R, I184F, G187S, G190A | hybrid[3] | >34 | >100 |
| | pGH (167–181) | R167K, D171H, I179V, Q181K | r.s. | 9.2 | 27 |

[1]Restriction selection - Wells, J. A., et al. (1986) Philos. Trans. R. Soc. London SerA 317, 415.
[2]Cassette mutagenesis - Wells, J. A., et al. (1985) Gene 34, 315.
[3]Recombination mutagenesis - Gray, G. L., et al. (1986) J. Bacteriol. 166, 635.

The segment-substituted hGH variants are generally identified by the analogous segments substituted into the human growth hormone sequence. However, in some instances, not all of the analogous residues in the substituted analogous segment were maintained in a particular construction. Thus, in Table III hPL (12–25) identifies a segment-substituted hGH variant wherein amino acids 12 through 25 of human placental lactogen (hPL) are substituted for amino acid residues 12 through 25 in the parent hGH. The effect of substituting this analogous segment can be determined by comparing the amino acid sequence of hGH and hPL in this region in FIG. 2. Four amino acid substitutions are generated in an hPL (12–25) variant where no other changes are made. These residues are 12, 16, 20 and 25 for hPL (12–25).

The actual amino acid substitutions in the hPL (12–25) variant and the other segment-substituted variants are shown in Table III. Each substitution is represented by a letter followed by a number which is followed by a letter. The first letter and number correspond to the amino acid at that residue number in the unmodified hGH. The last letter corresponds to the amino acid which is substituted at that position. Thus, N12H indicates that the asparagine at position 12 in hGH is substituted by histidine in the hPL (12–25) variant.

As can be seen, some of the actual substitutions introduced do not correspond to the totality of substitutions indicated by the corresponding segments in FIG. 2. Thus, hPL (12–25) would contain the four substitutions N12H, R16Q, L20A and F25L if the entire hPL (12–25) segment were substituted. The actual variant made, however, maintained R16 and L20 and therefore incorporated only two of the four substitutions, i.e., N12H and F25L, as shown in Table III. Other segment-substituted variants which maintained one or more resudues of the parent hGH include those covering regions A and E and the segment-substituted variants hPL (46–52) and pGH (167–181).

Each of the segment-substituted human growth hormone variants were assayed in an in vitro system comprising displacement of [$^{125}$I]hGH from the extracellular portion of the cloned soluble hGH receptor to quantify the relative affinities of the segment-substituted variants to the extracellular domain of the somatogenic receptor. Leung, D. W., et al. (1987) Nature 330, 537. This truncated form of the somatogenic receptor exhibits the same selectivity for hGH as the membrane form of the receptor (Spencer, S. A., et al. (1988) J. Biol. Chem. 263, 7862) albeit with about a slight reduction in binding affinity ($K_d$=0.3 nM).

As will be described in more detail in the examples, selected segments A, C and F, comprising residues 11–19, 54–74 and 164–191, respectively, are active domains in the hGH molecule interactive with the somatogenic receptor. This is based on the observed decrease in Kd of ten-fold or greater for most of the segment-substituted hGH variants containing analogous segments for hGH analogs over these regions. See FIG. 4. Of course, this does not mean that each of the amino acid residues within these active domains comprises the binding residues for the somatogenic receptor. Rather, such domains define the amino acid sequence within which such active residues can be found.

The active domains A, C and F were further localized. For example, the variant hPRL (12–33) was dissected into the amino and carboxy terminal variants, hPRL (12–19) and hPRL (22–33). The results from this experiment further localized this active domain of hGH to residues 12 through 19. Similarly, the amino terminal portion of region F (pGH (167–181)) exhibits a large reduction in binding affinity. One of the most dramatic effects was the 30-fold reduction in binding caused by hPL (56–64) which introduced only two mutations, E56D and R64M. Although regions A, C and F are widely separated in the primary sequence of hGH, the tertiary folding of the hormone brings them within close proximity. See FIG. 5. These active domains form a patch that contains the amino terminus of helix 1 (active domain A), the loop from Cys-53 to the start of helix 2 (active domain C) and the central portion of helix 4 (active domain F).

In addition, eight Mabs against hGH were assayed against segment-substituted hGH variants to map the epitopes of hGH. Further, the Mab's were used in a competitive assay with hGH and hGH variants to evaluate the ability of each of the Mabs to block the binding of the hGH receptor to hGH.

The collective results obtained from these experiments provide several lines of evidence that the substitution of analogous segments into hGH do not grossly disrupt the native folding of the molecule and that the observed activity is due to a direct effect on the interaction between the somatogenic receptor and the segment-substituted hGH variants. Firstly, the segment-substituted variants are highly selective in disrupting binding to the somatogenic receptor or the Mabs. Secondly, the somatogenic receptor and Mabs recognize conformation as well as sequence. The receptor and at least four of the Mabs recognize discontinuous epitopes that are sensitive to the protein tertiary structure. Thirdly, circular dichroic spectra of all of the purified variants are virtually identical to wild-type hGH. Fourthly, all of the variants, with the exception of pGH (164–190), were expressed in essentially wild-type amounts. Resistance to proteolysis in vivo has been used as a screen for conformational integrity. Hecht, M. H., et al. (1984) *Proc. Natl. Acad. Sci. USA* 81, 5685; Shortle, D., et al. (1985) *Genetics* 110, 539.

The alteration in binding activity for segment-substituted hGH variants does not necessarily indicate that the substituted residues in such variants make direct contact with the somatogenic receptor. A disruptive mutation may not only remove a favorable interaction but may introduce an unfavorable one. For example, the N12R mutation in the hPRL (12–19) segment-substituted hGH variant not only changes the hydrogen bonding amide function of Asn12, the Arg substitution also introduces a bulkier side chain that is positively charged. Furthermore, a number of the binding contacts may be conserved between the analogs so that not all contacts, or even regions, may be probed by generating segment-substituted hGH variants. Further, the substitution of analogous segments generates the substitution of multiple amino acid residues in the hGH molecule.

In order to identify the specific active amino acids within the active domains A, C and F in FIG. 2, a fine structure analysis of these active domains was performed. In this analysis, residues in these three active domains were replaced sequentially with alanine. A total of 63 single Alanine mutants were made and each of their binding constants were determined for the soluble hGH receptor (shGHr) by Scatchard analysis. Leung, D. W., et al. (1988) *J. Biol. Chem.* 263, 7862.

Based on this analysis, the amino acid residues listed in Table IV comprise residues within the hGH molecule which are actively involved in the interaction with the somatogenic receptor. This is based on the more than four-fold effect on the relative dissociation constant caused by the substitution of alanine for these residues as compared to wt hGH. See FIG. 7. Preferred amino acid substitutions for these residues to form hGH variants are shown.

TABLE IV

| hGH Residue | Preferred amino acid substitution |
|---|---|
| F10 | GEMARQSYWLIV |
| F54 | GEMARQSYWLIV |
| E56 | GMFARQSDNKLH |
| I58 | GEMFARQSVT |
| R64 | GEMFAQSH,KDN |
| Q68 | GEMFARSHKDN |
| D171 | GEMFARQSHKN |
| K172 | GEMFARQSHDN |
| E174 | GMFARQSHDNKL |
| T175 | GEMFARQSVI |
| F176 | GEMARQSYWLIV |
| R178 | GEMFAQSHKDN |
| C182 | GEMFARQS |
| V185 | GENFARQSITLYW |

Other amino acid residues which are less active with the somatogenic receptor are listed in Table V. These residues demonstrate generally less than two-fold increase in relative Kd when substituted with alanine.

TABLE V

| I4 | N12 | S55 | E66 | Q181 |
| P5 | M14 | S57 | K70 | R183 |
| L6 | L15 | P59 | S71 | G187 |
| S7 | R16 | S62 | K168 | |
| R8 | R19 | N63 | I179 | |

Amino acid residues in hGH showing a relative decrease in Kd when substituted with alanine (and consequently greater affinity for the somatogenic receptor) are listed in Table VI.

TABLE VI

| P2 | E65 | S184 |
| T3 | Q69 | E186 |
| L9 | L73 | S188 |
| H18 | R167 | F191 |
| R64 | E174 | |

One residue-substituted hGH variant, E174A, surprisingly resulted in a significant decrease (almost five-fold) in the dissociation constant with the somatogenic receptor. This variant, in addition to showing an increased binding affinity for the somatogenic receptor, also exhibited an increased somatogenic potency relative to hGH in a rat weight gain assay. This and other specific residue substitutes that enhance somatogenic binding by >1.4 fold are presented in Table VII.

TABLE VII hGH variants having enhanced somatogenic binding

| hGH residues | Substituted amino acid |
|---|---|
| H18 | A |
| R64 | K |
| E65 | A |
| L73 | A |
| E174 | A,N,Q,S,G |
| E186 | A |
| S188 | A |
| F191 | A |

Other variants containing alanine substitutions not shown in FIG. 7 are listed in Table VIII.

TABLE VIII

| Variant | $K_d$ (mM) | $K_d$ (var)/$K_d$ (wt) |
|---|---|---|
| H21A | NE | — |
| K172A/F176A | 201 | 543 |
| N47A | 0.84 | 2.3 |
| P48A | NE | — |
| Q49A | 0.36 | 1.0 |
| T50A | 0.38 | 1.0 |
| S51A | | |
| Q46A | NE | — |
| V173A | NE | — |

Note:
NE - not expressed in shake flasks at levels which could be easily isolated (i.e., < – 5% of wild-type expression levels).

Once identified, the active amino acid residues for the somatogenic receptor in hGH are analyzed by substituting different amino acids for such residues other than the scanning amino acid used for the preliminary analysis. The residue-substituted variants in Table IX have been made.

TABLE IX

| Variant | $K_d$ (nM) | $K_d$ (var)/$K_d$ (wt) |
|---|---|---|
| R77V | 0.44 | 1.3 |
| L80D | 0.78 | 2.3 |
| F176Y | 3.2 | 8.6 |
| E174G | 0.15 | 0.43 |
| E174D | NE | — |
| E174H | 0.43 | 1.2 |
| E174K | 1.14 | 3.1 |
| E174L | 2.36 | 6.4 |
| E174N | 0.26 | 0.7 |
| E174Q | 0.21 | 0.6 |
| E174S | 0.11 | 0.3 |
| E174V | 0.28 | 0.8 |
| E174R | NE | — |
| R64K | 0.21 | 0.6 |
| E65K | NE | — |
| E65H | NE | — |
| K172R | NE | — |
| I58L | NE | — |
| F25S | NE | — |
| D26E | NE | — |
| Q29S | NE | — |
| E30Q | NE | — |
| R178K | NE | — |
| R178T | NE | — |
| R178Q | NE | — |

TABLE IX-continued

| Variant | $K_d$ (nM) | $K_d$ (var)/$K_d$ (wt) |
|---|---|---|
| I179M | NE | — |
| D169N | 3.6 | 10.5 |

Note:
NE - not expressed in shake flasks at levels which could be easily isolated (i.e., <~ 5% of wild-type expression levels).

In addition to the hGH variants that have been made, Table X identifies specific amino acid residues in hGH and replacement amino acids which are expected to produce variants having altered biological functions.

TABLE X

| wT hGH amino acid residue | Replacement amino acid |
|---|---|
| S43 | GEMFARQHDKN |
| F44 | GEMARQSYWLIV |
| H18 | GEMFARQSKDNY |
| E65 | GMFARQSHDNKL |
| L73 | GEMFARQSIVY |
| E186 | GMFARQSHDNKL |
| S188 | GEMFARQHDNKY |
| F191 | GEMARQSYWLIV |
| F97 | GEMARQSYWLIV |
| A98 | GEMFRQSDNHK |
| N99 | GEMFARQSDKY |
| S100 | GEMFARQHDNKY |
| L101 | GEMFARQSIVY |
| V102 | GEMFARQSITLYW |
| Y103 | GEMFARQSWLIV |
| G104 | EMFARQSP |
| R19 | GEMFAQSHKND |
| Q22 | GEMFARSKKDN |
| D26 | GEMFARQSHKN |
| Q29 | GEMFARSKKDN |
| E30 | GMFARQSHDNKL |
| E33 | GMFARQSHDNKL |

In another embodiment, the binding epitope of hGH for the prolactin receptor was determined. hGH can bind to either the growth hormone or prolactin (pRL) receptor. As will be shown herein, these receptors compete with one another for binding to hGH suggesting that their binding sites overlap. Scanning mutagenesis data show that the epitope of hGH for the hPRL receptor consists of determinants in the middle of helix 1 (comprising residues Phe25 and Asp26), a loop region (including Ile58 and Arg64) and the center portion of helix 4 (containing residues K168, K172, E174, and F176). These residues form a patch when mapped upon a structural model of hGH. This binding patch overlaps but is not identical to that C determined for the hGH receptor as disclosed herein and by B. C. Cunningham and J. A. Wells (1989) *Science* 244, 1081–1085. By mutating the non-overlap regions of these receptor binding sites on hGH, the preference of hGH was shifted toward the hGH receptor by >2000-fold or toward the hPRL receptor by >20-fold without loss in binding affinity for the preferred receptor. Similarly, by mutating the overlap regions it is possible to reduce binding to both receptors simultaneously by >500-fold. Such receptor selective variants of hGH should be useful molecular probes to link specific receptor binding events to the various biological activities of hGH such as linear growth or lactation.

In a further embodiment, the receptor-binding determinants from human growth hormone (hGH) were placed into the normally nonbinding homolog, human prolactin (hPRL). The alanine scanning mutagenesis disclosed herein and Cunningham, B. C. & Wells, J. A. (1989) Science 244, 1081–1085 identified important residues in hGH for modulating binding to the hGH receptor cloned from human liver. Additional mutations derived from hPRL were introduced into hGH to determine which hPRL substitutions within the hGH receptor binding site were most disruptive to binding. Thereafter, the cDNA for hPRL was cloned and expressed in *Escherichia coli*. It was then mutated to sequentially introduce those substitutions from hGH that were predicted to be most critical for receptor binding. After seven iterative rounds of site-specific mutagenesis, a variant of hPRL containing eight mutations whose association constant was strengthened over 10,000-fold for the hGH receptor was identified. This hPRL variant binds only six-fold weaker than wild-type hGH while sharing only 26% overall sequence identity with hGH. These results show the structural similarity between hGH and hPRL, and confirm the identity of the hGH receptor epitope. More generally, these studies demonstrate the feasibility to borrow receptor binding properties from distantly related and functionally divergent hormones that may prove useful for the design of hybrid hormones with new properties as agonist or antagonist.

The following is presented by way of example and is not to be construed as a limitation to the scope of the invention.

EXAMPLE 1 hGH Mutagenesis and Expression Vector

To facilitate efficient mutagenesis, a synthetic hGH gene was made that had 18 unique restriction sites evenly distributed without altering the hGH coding sequence. The synthetic hGH DNA sequence was assembled by ligation of seven synthetic DNA cassettes each roughly 60 base pairs (bp) long and sharing a 10 bp overlap with neighboring cassettes to produce the 405 bp DNA fragment shown from NsiI to BglII. The ligated fragment was purified and excised from a polyacrylamide gel and cloned into a similarly cut recipient vector, pB0475, which contains the alkaline phosphatase promoter and StII signal sequence (Chang, C. N., et al. (1987) *Gene* 55, 189), the origin of replication for the phage f1 and pBR322 from bp 1205 through 4361 containing the plasmid origin of replication and the β lactamase gene. The sequence was confirmed by dideoxy sequence analysis (Sanger, F., et al. (1977) *Proc. Natl. Acad. Sci. USA* 74, 5463).

pB0475 was constructed as shown in FIG. 9. fI origin DNA from filamentous phage contained on a DraI, RsaI fragment 475 bp in length was cloned into the unique PvuII site of pBR322 to make plasmid p652. Most of the tetracycline resistance gene was then deleted by restricting p652 with NheI and NarI, filling the cohesive ends in with DNA polymerase and dNTPs and ligating the large 3850 bp fragment back upon itself to create the plasmid pΔ652. pΔ652 was restricted with EcoRI, EcoRV and the 3690 bp fragment was ligated to a 1300 bp EcoRI, EcoRV fragment from phGH4R (Chang, C. N., et al. (1987) *Gene* 55, 189) containing the alkaline phosphatase promoter, STII signal sequence and natural hGH gene. This construction is designated as pB0473. Synthetically derived DNA was cloned into pB0473 in a three-way construction. The vector pB0473 was restricted with NsiI, BglII and ligated to a 240pb NsiI, HindIII fragment and a 1170 bp HindII, BglII fragment both derived from synthetic DNA. The resulting construction pB0475 contains DNA coding for the natural polypeptide sequence of hGH but possesses many new unique restriction sites to facilitate mutagenesis and further manipulation of the hGH gene. The entire DNA sequence of pB0475 together with the hGH amino acid sequence is shown in FIG. 10. The unique restriction sites in the hGH sequence in pB0475 allowed insertion of mutagenic cassettes (Wells, J. A., et al. (1985) *Gene* 34, 315) containing DNA sequences encoding analogous segments from the analogs pGH, hPL and hPRL. Alternatively, the hGH sequence was modified by site specific mutagenesis in the single-stranded pB0475 vector followed by restriction-selection against one of the unique restriction sites (Wells, J. A., et al. (1986) *Philos. Trans. R. Soc. London SerA* 317, 415).

The 17 segment-substituted hGH variants in Table III were prepared. Each was secreted into the periplasmic space of *E. coli* at levels comparable to wild-type hGH and at levels that far exceeded the hGH-pGH hybrid described infra. The hGH and hGH variants were expressed in *E. coli* W3110, tonA (ATCC 27325) grown in low phosphate minimal media (Chang, C. N., et al. (1987) *Gene* 55, 189).

The hGH and hGH variants were purified as follows. To 200 g of cell paste four volumes (800 ml) of 10 mM TRIS HCl Tris(hydroxymethyl)aminomethane hydrochloride; pH 8.0 was added. The mixture was placed on an orbital shaker at room temperature until the pellets were thawed. The mixture was homogenized and stirred for an hour in a cold room. The mixture was centrifuged at 7000 g for 15 min. The supernatant was decanted and ammonium sulfate was added to 45% saturation (277 g/l) and stirred at room temperature for one hour. After centrifugation for 30 minutes at 11,000 g, the pellet was resuspended in 40 ml 10 mM TRIS HCl Tris(hydroxymethyl)aminomethane hydrochloride; pH 8.0. This was dialyzed against 2 liters of 10 mM TRIS HCl Tris(hydroxymethyl)aminomethane hydrochloride; pH 8.0 overnight. The sample was centrifuged or filtered over a 0.45 micron membrane. The sample was then loaded on a column containing 100 ml of DEAE cellulose (Fast Flow, Pharmacia, Inc.). A gradient of from zero to 300 mM NaCl in 10 mM TRIS HCl Tris(hydroxymethyl) aminomethane hydrochloride pH; 8.0 in 8 to 10 column volumes was passed through the column. Fractions containing hGH were identified by PAGE, pooled, dialyzed against 10 mM TRIS HCl Tris(hydroxymethyl)aminomethane hydrochloride. pH 8.0 overnight. Samples were concentrated to approximately 1 mg/ml by Centri-Prep10 ultrafiltration.

EXAMPLE 2

Homologous Recombinants of hGH and pGH

A random hybrid library containing various N-terminal lengths of hGH linked to the remaining C-terminal portion of porcine growth hormone (pGH) was constructed by the method of random recombination of tandomly linked genes. Gray, G. L., et al. (1986) *J. Bacteriol.* 166, 635.

The EcoRI site of pB0475 was removed by restricting the plasmid with EcoRI, filling in the cohesive ends by addition of DNA polymerase and dNTPs, and ligating the plasmid back together. A new EcoRI site was then introduced just following the 3' end of the hGH gene. This was accomplished by subcloning the 345 bp BglII, EcoRV fragment of hGH-4R, which contains such an EcoRI site, into similarly restricted vector from the EcoRI= pB0475 construction. The pGH gene (Seeburg, P. H., et al. (1983) *DNA* 2, 37) was then introduced just downstream and adjacent to the 3' end of the hGH gene in this construction. This was accomplished by doping an EcoRI, HindIII (filled in) fragment containing pGH cDNA into the large fragment of a EcoRI, EcoRV digest of the construction described above. The resulting plasmid, pB0509, contains an intact hGH gene with a unique EcoRI site at its 3' end followed by an intact pGH gene reading in the same direction. Due to the homology between the hGH and pGH genes, a percentage of the pB0509 plasmid underwent in vivo recombination, to make hybrid hGH/pGH genes when transformed into *E. coli* rec+ MM294 (ATCC 31446). These recombinants were enriched by restricting pool DNA with EcoRI to linearize plasmids which had not undergone recombination, resulting in the loss of that EcoRI site. After two rounds of restriction selection and transformation into *E. coli* rec+ MM294 nearly all the clones represented hybrid hGH/pGH recombinants. Sequence analysis of 22 clones demonstrate that the hGH/pGH hybrids contained amino terminal hGH sequence followed by pGH sequence starting at amino acid residues +19, +29, +48, +94, +105, +123 and +164.

Seven hGH-pGH hybrids having cross-over points evenly distributed over the hGH gene were obtained. However, only the extreme carboxy terminal hybrid (hGH (1–163)-pGH (164–191)) was secreted from *E. coli* at levels high enough to be purified and analyzed. This hGH-pGH hybrid introduces three substitutions (M170L, V173A and V180M) that are located on the hydrophobic face of helix 4. Accordingly, most of the sequence modifications in the helical regions A, D, E and F in FIG. 2 were designed to avoid mutations of residues on the hydrophobic face of the helices. For example, the above hybrid hGH-pGH variant was modified to retain M170, V173, F176 and V180 because these residues are inside or bordering the hydrophobic face of helix 4.

EXAMPLE 3

Expression and Purification of Soluble *Human Growth Hormone Receptor* from *E. coli*

Figure 11:
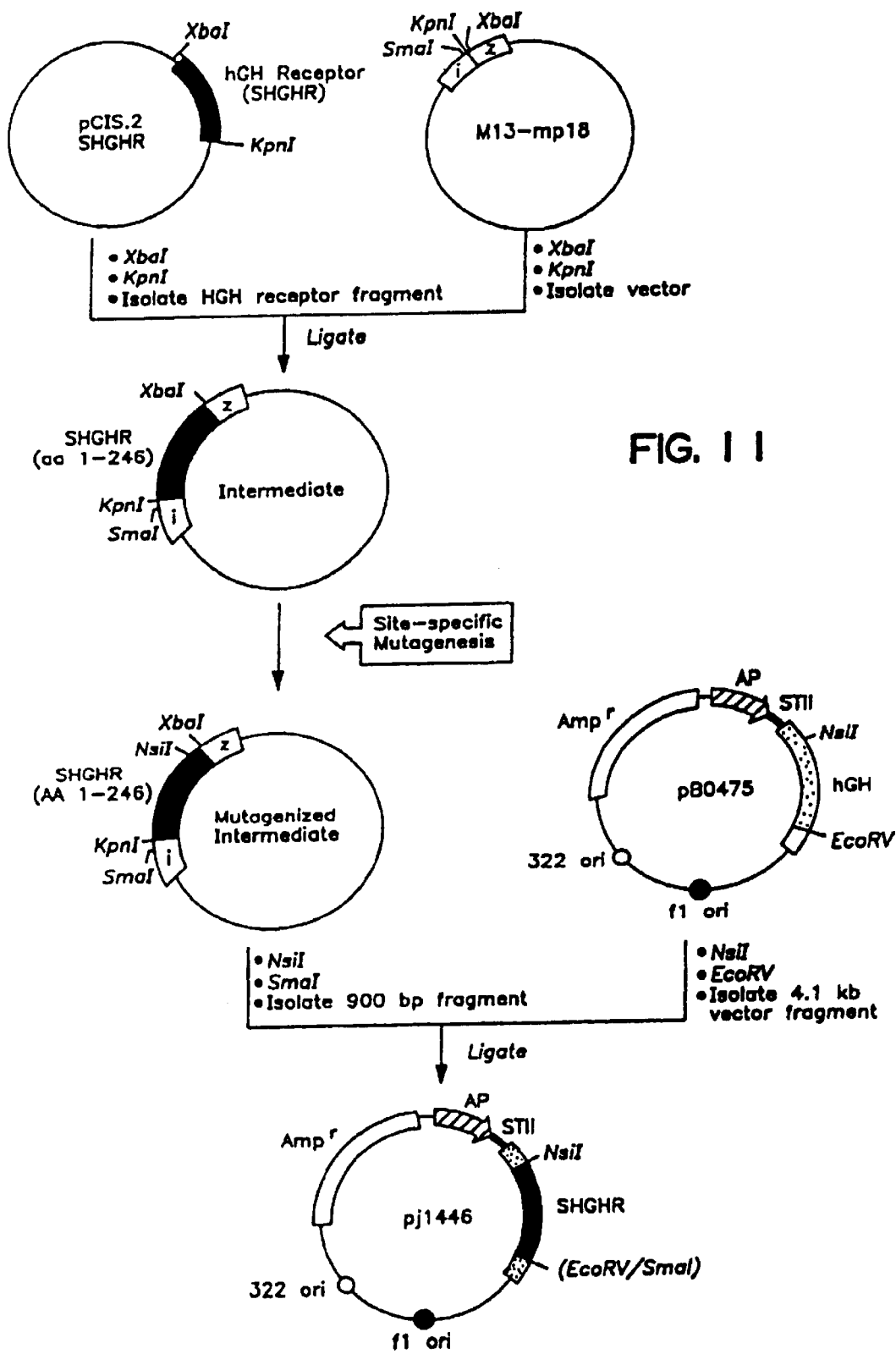
FIG. 11 depicts the construction of vector pJ1446.
Figure 12A:
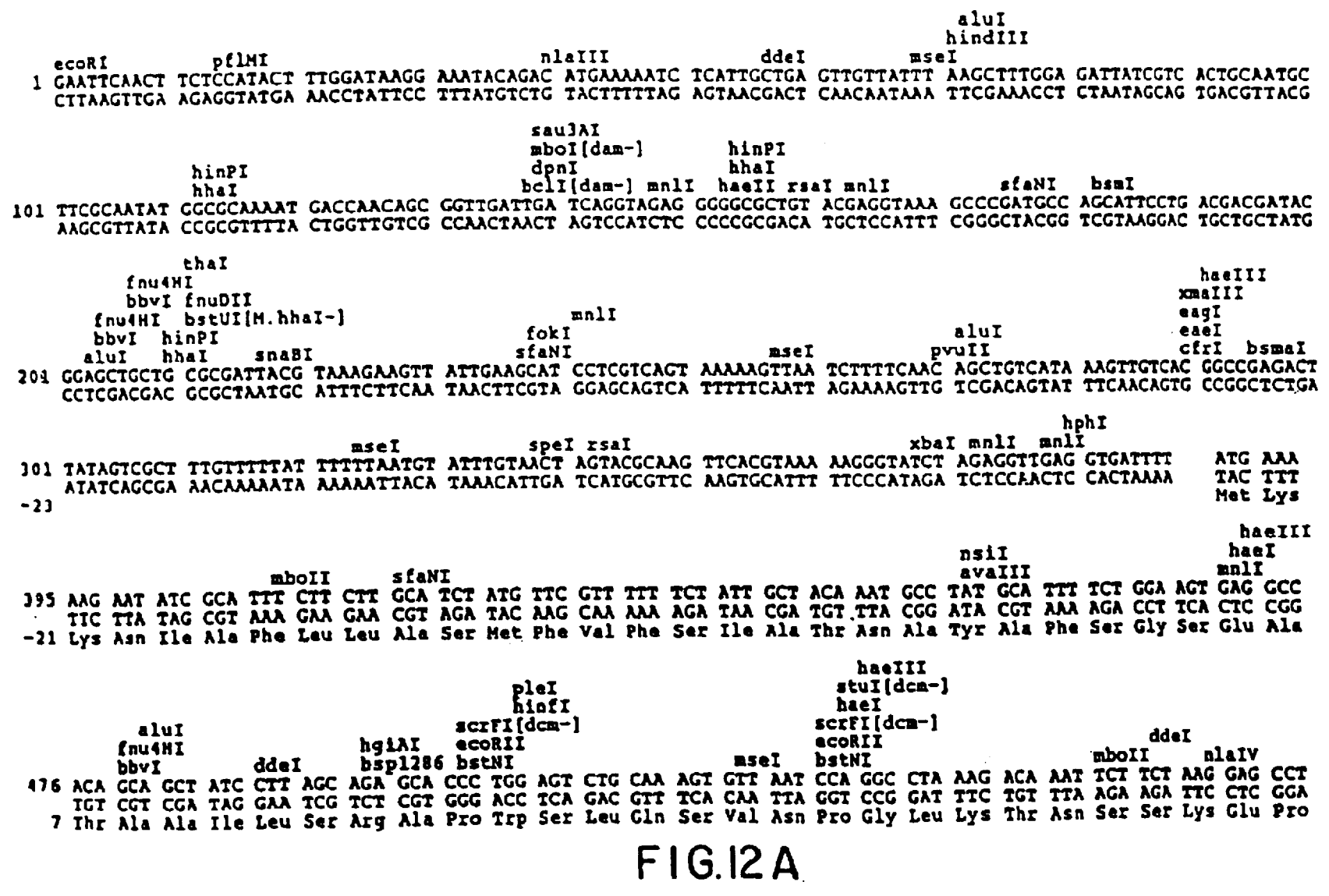
Figure 12B:
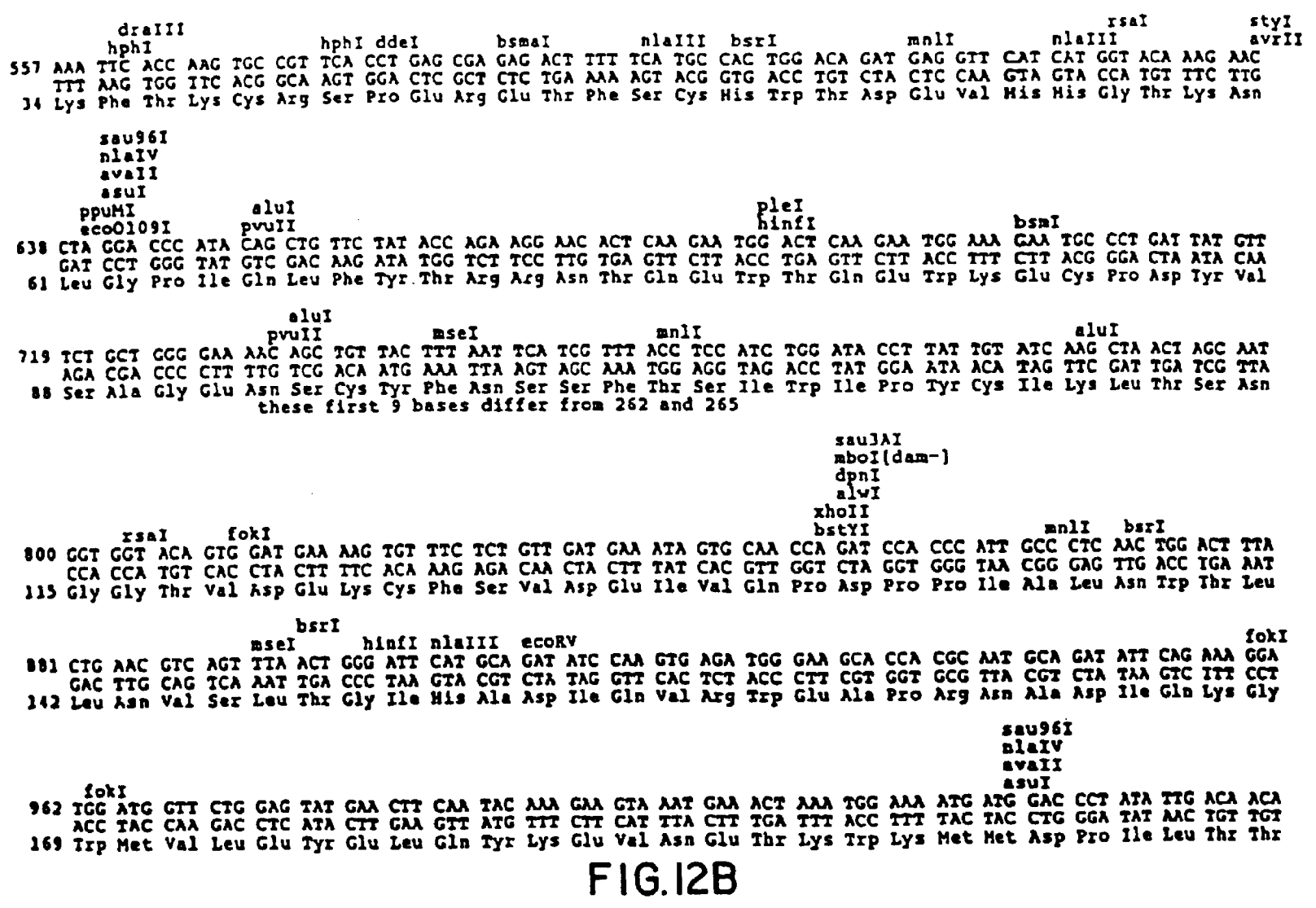
Figure 12C:
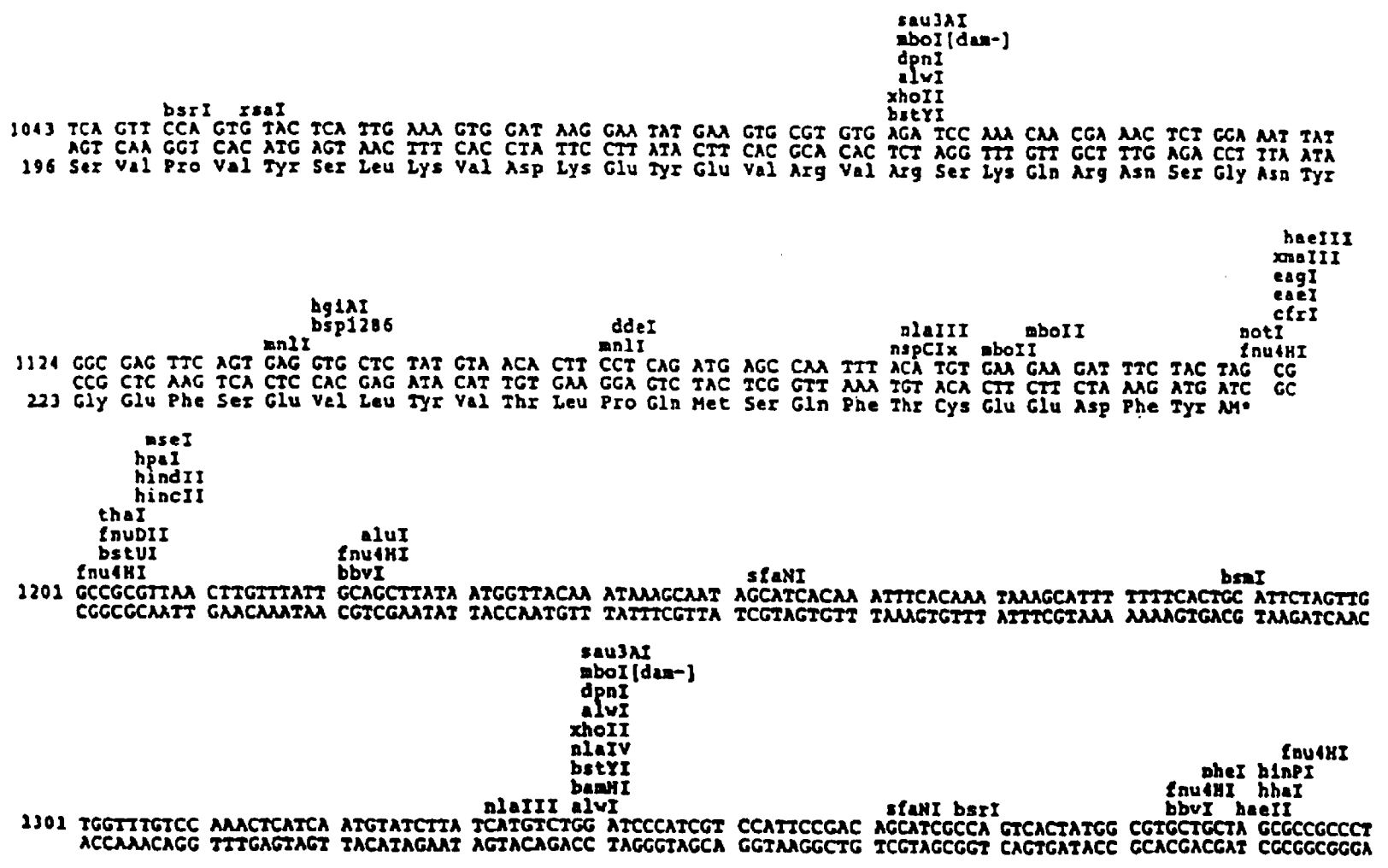
Figure 12D:
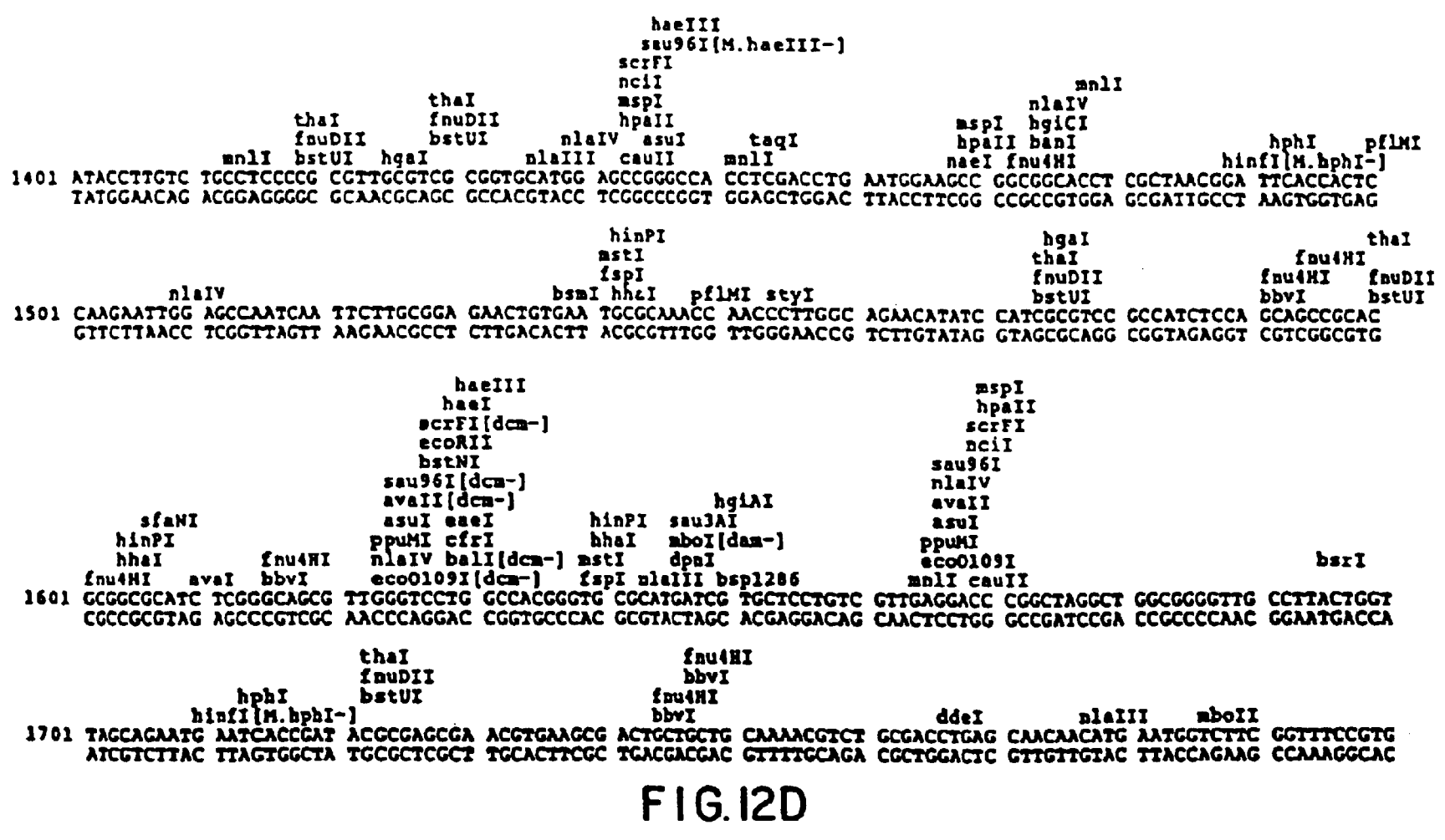
Figure 12E:
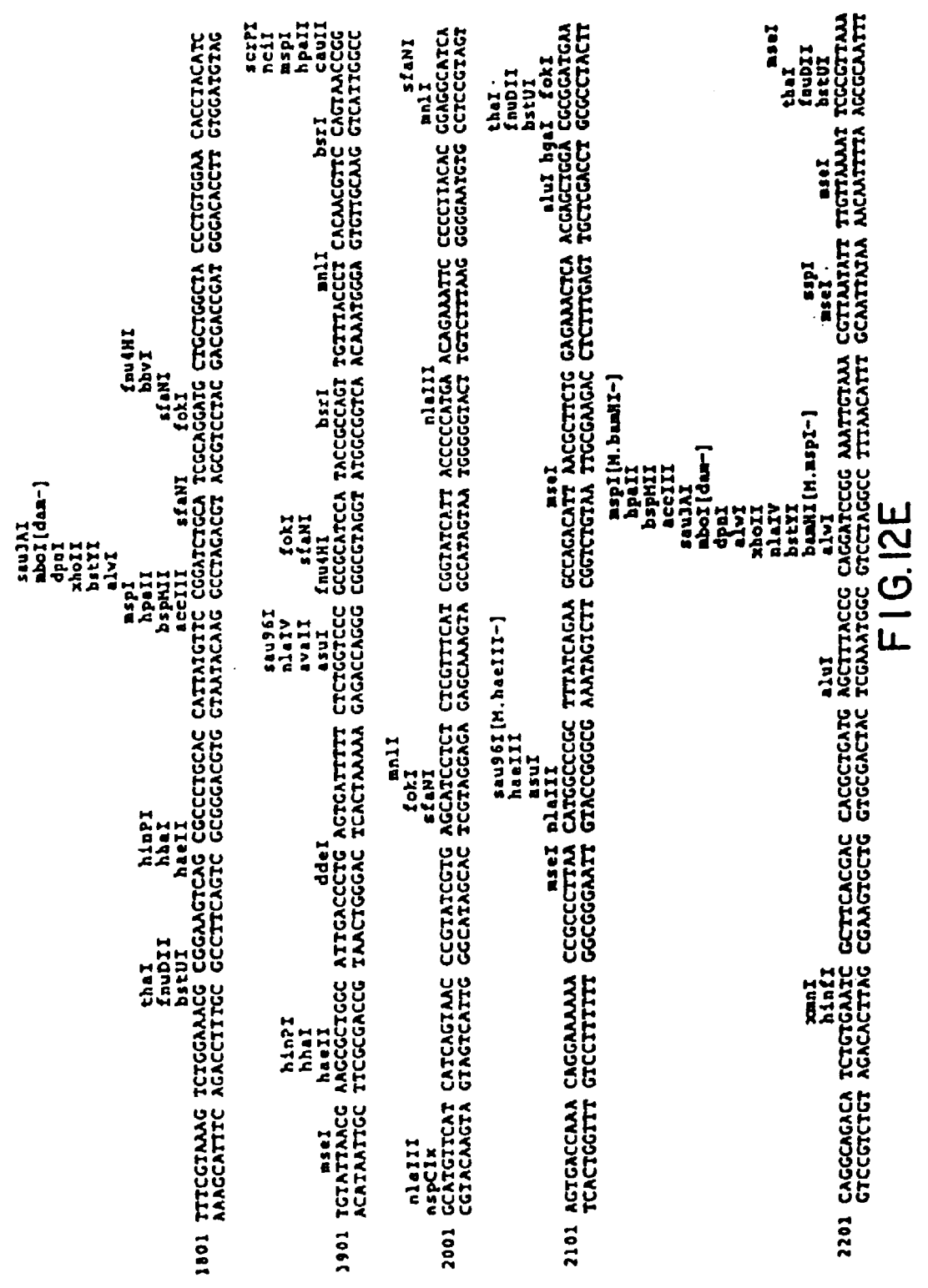
Figure 12F:
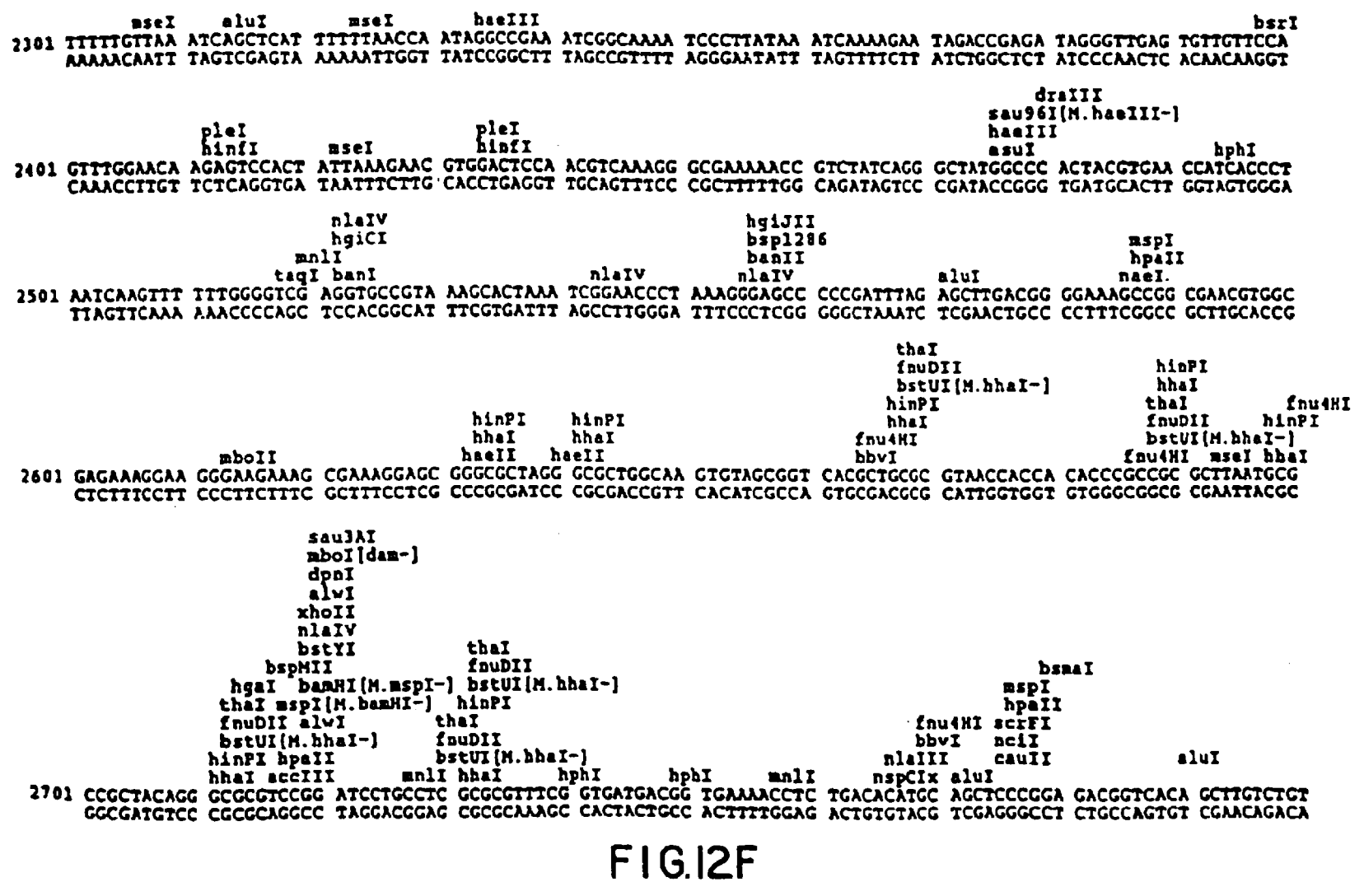
Figure 12G:
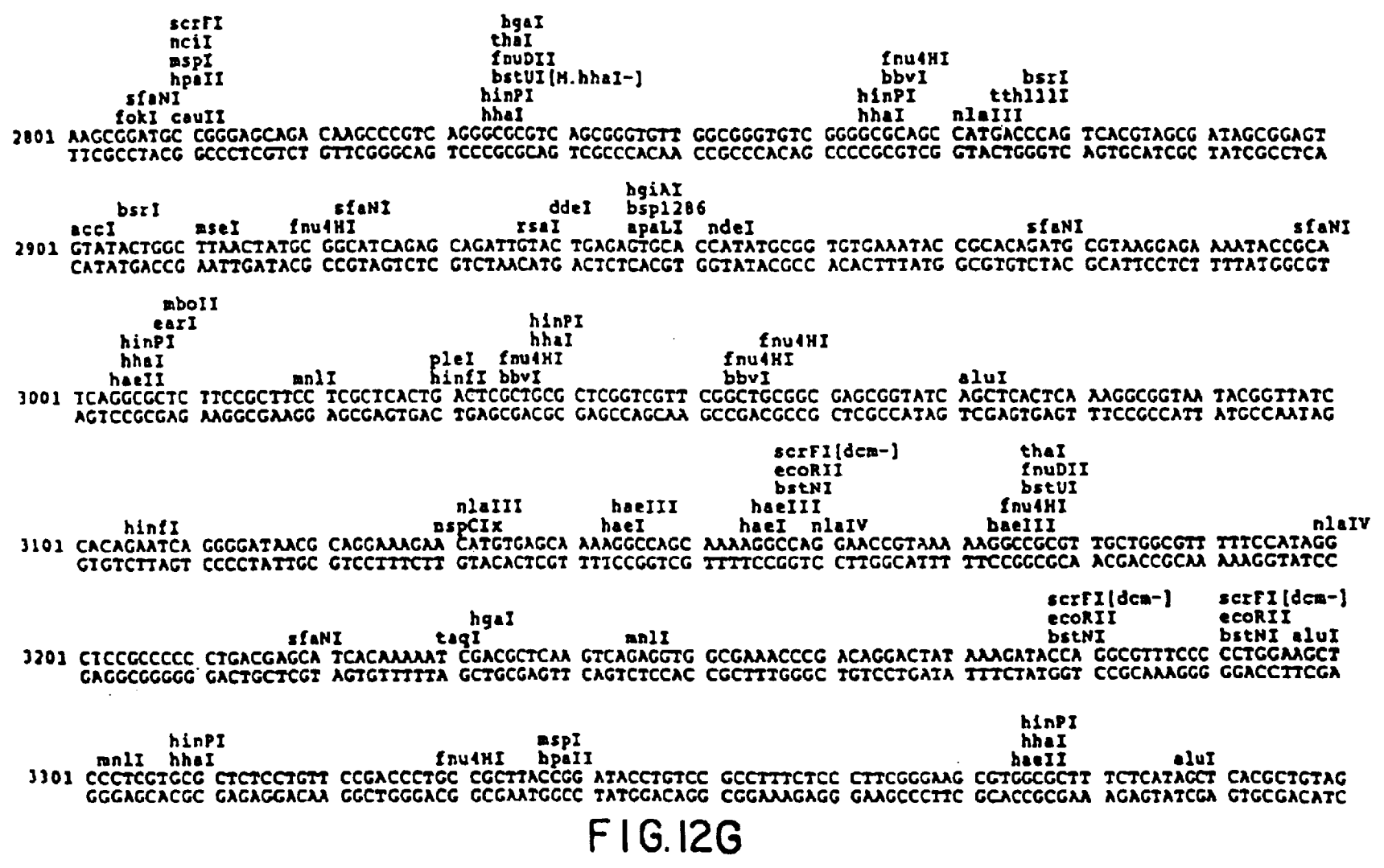
Figure 12H:
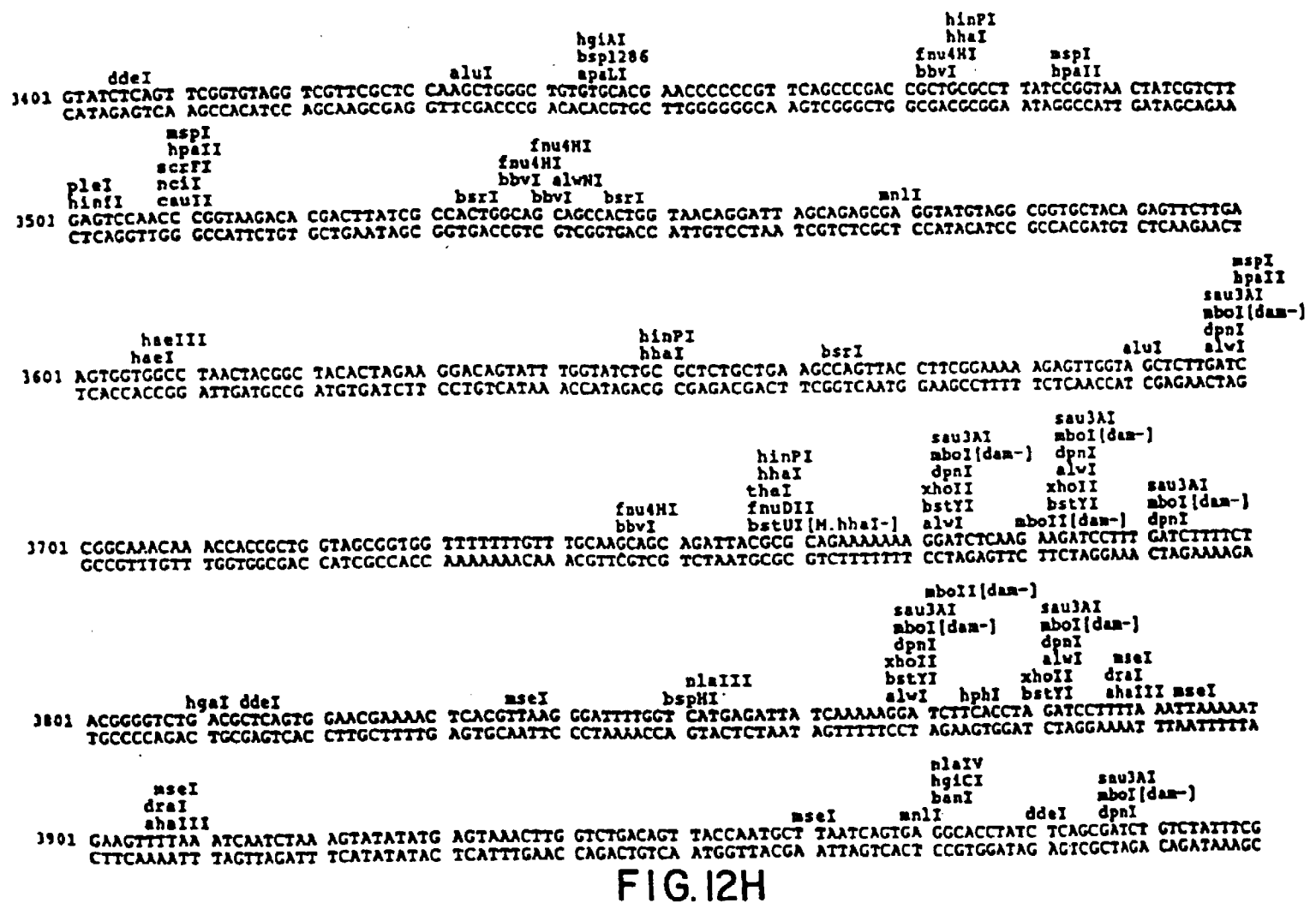
Figure 12I:
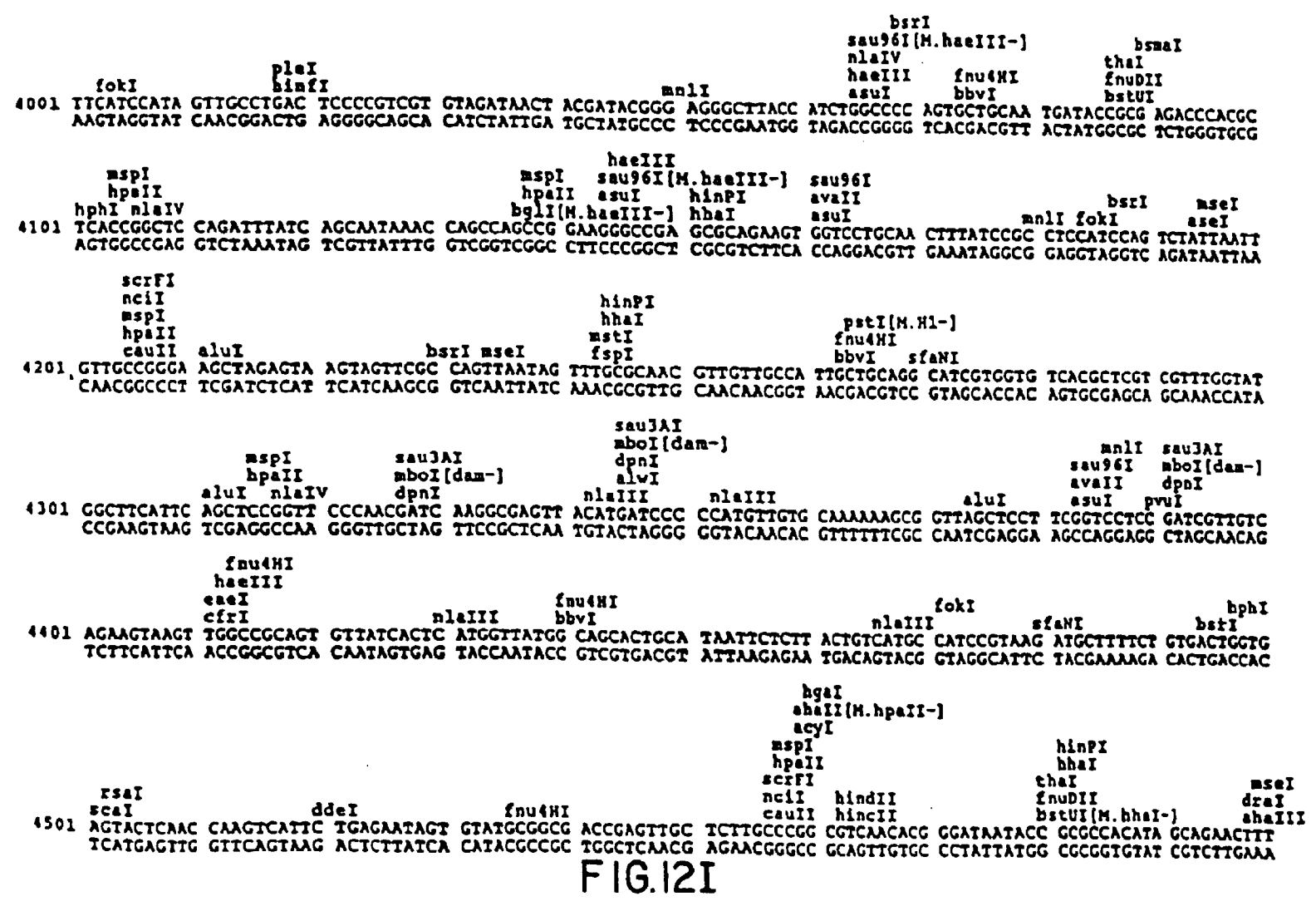
Figure 12J:
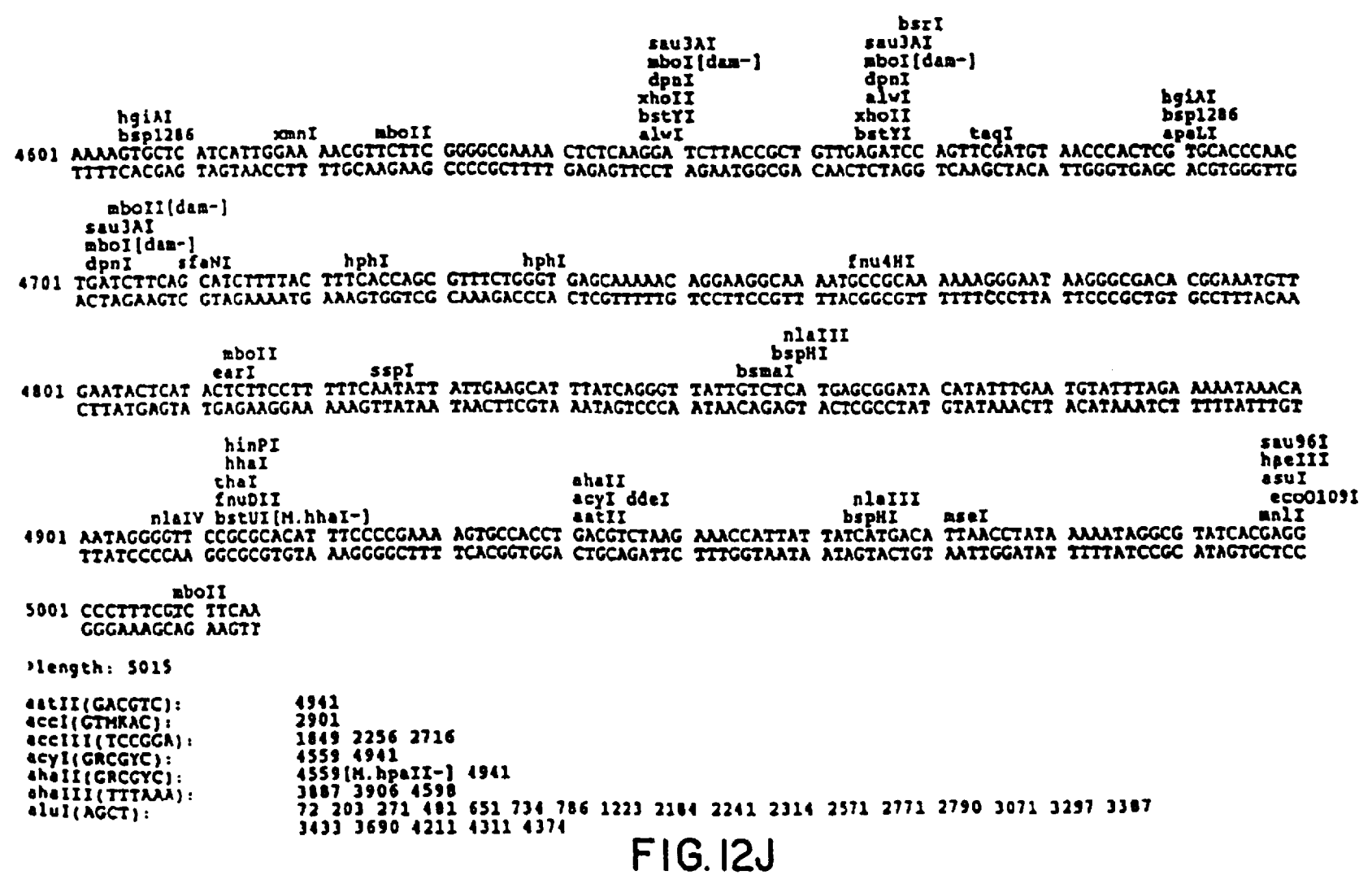

Cloned DNA sequences encoding the soluble human growth hormone receptor shGHr (Leung, D. W., et al. (1987) *Nature* 330, 537) were subcloned into pB0475 to form pJ1446 (see FIGS. 11 and 12).

The vector pC1S.2 SHGHR (Leung, D. W., et al. (1987) *Nature* 33, 537) was digested with XbaI and KpnI and the 1.0 kb fragment containing the secretion signal plus the 246 codon extracellular portion of the hGH receptor was purified (Maniatis, T. et al. (1982) in *Molecular Cloning*, Cold Springs Harbor Laboratory, N.Y.). This fragment was ligated into similarly cut M13-mp18 and single-stranded DNA for the recombinant gene was purified (Messing, J. (1983) *Methods in Enzymology*, Vol. 101, p. 20). Site-specific mutagenesis (Carter, P., et al. (1986) *Nucleic Acids Res.* 13, 4331) was carried out to introduce an NsiI site at codon +1 using the 18-mer oligonucleotide, 5'-A-AGT-GAT-GCA-TTT-TCT-GG-3'. The mutant sequence was verified by dideoxy sequence analysis (Sanger, F., et al. (1977) *Proc.* *Natl. Acad. Sci. USA* 74, 5463). Double-stranded DNA for the mutant was purified and cut with NsiI and SmaI. The 900 bp fragment was isolated containing the 246 codon extracellular portion of the hGH receptor. pB0475 was cut with NsiI and EcoRV and the 4.1 kb fragment (missing the synthetic hGH gene) was purified. The 900 bp fragment for the receptor and the 4.1 kb vector fragment were ligated and the recombinant clone (pJ1446) was verified by restriction mapping. This was transformed into the *E. coli* KS303 (Strauch, K., et al. (1988) *Proc. Natl. Acad. Sci. USA* 85, 1576) and grown in low-phosphate media (Chang, C. N. (1987) *Gene* 55, 189) at 30° C. The receptor fragment protein was purified by hGH affinity chromatography (Spencer, S. A., et al. (1988) *J. Biol. Chem.* 263, 7862; Leung, D. W., et al. (1987) *Nature* 330, 537). The sequence for pJ1446 is shown in FIG. 12 together with the amino acid sequence of the cloned receptor.

*E. coli* W3110, degp (Strauch, K. L., et al. (1988) *PNAS USA* 85, 1576) was transformed with pJ1446 and grown in low-phosphate media (Chang, C. N. (1987) *Gene* 55, 189) in a fermentor at 30° C. The 246 amino acid hGHr was used to generate preliminary data. A slightly shorter hGHr containing amino acids 1 through 238 was used in the examples herein. The results obtained with that receptor were indistinguishable from those obtained with the 246 amino acid hGHr.

The plasmid phGHr(1–238) (Table X(A)) was constructed to generate a stop codon after Gln238 to avoid the problem of carboxyl terminal heterogeneity. The binding protein from KS330 cultures containing phGHr(1–238) was produced in slightly higher yields and with much less heterogeneity (data not shown) than frog cultures containing phGHr(1–246). Routinely, 20 to 40 mg of highly purified binding protein could be isolated in 70 to 80 percent yield starting from 0.2 kg of wet cell paste (~2 liters high cell density fermentation broth). Both N-terminal sequencing and peptide mapping coupled to mass spectral analysis of the C-terminal peptide confirmed that the product extended from residues 1 to 238.

Site-directed mutagenesis of the phGHr (1–246) template was performed (Carter, et al. (1986) *Nucleic Acids Res.* 13, 4431–4443) to produce phGHr (1–240, C241R) using the oligonucleotide

5'-ATG-AGC-CAA-TTT-<u>ACG-CGT</u>-TAG-GAA-GAT-TTC-3';

the asterisks are mismatches from the phGHr (1–246) template, underlined is a new unique MluI site) and CGT-TAG directs the C241R mutation followed by a stop codon (Table X(A)).

TABLE X(A)

Sequences of amino- and carboxyl-termini of hGH binding protein constructions

| Plasmid | Termini | Protein/DNA sequence/Restriction sites |
|---|---|---|
| phGHr(1–246) | Amino | -3 -2 -1 +1 +2 +3<br>ALA-TYR-ALA-PHE-SER-GLY<br>GCC-T<u>AT-GCA-T</u>TT-TCT-GGA<br>NsiI |
| phGHr(1–246) | Carboxyl | 238 239 240 241 242 243 244 245 246<br>GLN-PHE-THR-CYS-GLU-GLU-ASP-PHE-TYR-AM |

TABLE X(A)-continued

Sequences of amino- and carboxyl-termini of hGH
binding protein constructions

| Plasmid | Termini | Protein/DNA sequence/Restriction sites |
|---|---|---|
| | | CAA-TTT-ACA-TGT-GAA-GAA-GAT-TTC-TAC-TA<u>G-CGGCCGC</u> |
| | | <div align="right">NotI</div> |
| phGHr (1-240,C241R) | Carboxyl | Gln-Phe-Thr-Arg-AM<br>   \* \*\*  \* \*<br>CAA-TTT-<u>ACG-CGT</u>-TAG-GAA-GAT-TTC-TAC-TA<u>G-CGGCCGC</u><br>       MluI                                      NotI |
| phGHr(1-238) | Carboxyl | Gln-AM<br>   \*\*     \*\*  \* \*<br>CAA-<u>TAG</u>-ACA-CGT-TAG-GAA-GAT-TTC-TAC-TA<u>G-CGGCCGC</u><br>                                                    NotI |

*Indicates mismatches frow the wild-type template

The plasmid, phGHr (1–238), was produced by site-directed mutagenesis on the phGHr (1–240, C241R) template using restriction-selection (Wells, et al., (1986) *Phil. Trans. R. Soc. Lond. A*, 317, 415–423) against the MluI site (Table X(A)). Briefly, an oligonucleotide,

5'-AG-ATG-AGC-CAA-TAG-<u>ACA-CGT</u>-TAG-GAA-3' introduced a translation stop codon after Gln238 (CAA triplet) and altered the MluI restriction-site (underlined). After growing up the pool of duplex DNA from the initial transfection with heteroduplex, the DNA was restricted with MluI and retransformed to enrich for the desired phGHr (1–238) plasmid prior to DNA sequencing.

It was subsequently determined by DNA sequencing that the cloned hGH binding proteins in phGHr(1–238) contained a T51A mutation which arose either as a cDNA variant or as a cloning artifact. The A51T revertant was therefore to be identical to the published sequence (Leung, et al., (1987) *Nature (London)* 330, 537–543). The purification and binding properties of the proteins containing either Thr or Ala at position 51 were indistinguishable (results not shown). The Ala51 binding protein variant was selected for all subsequent analysis because it had been characterized more thoroughly.

Figure 24:
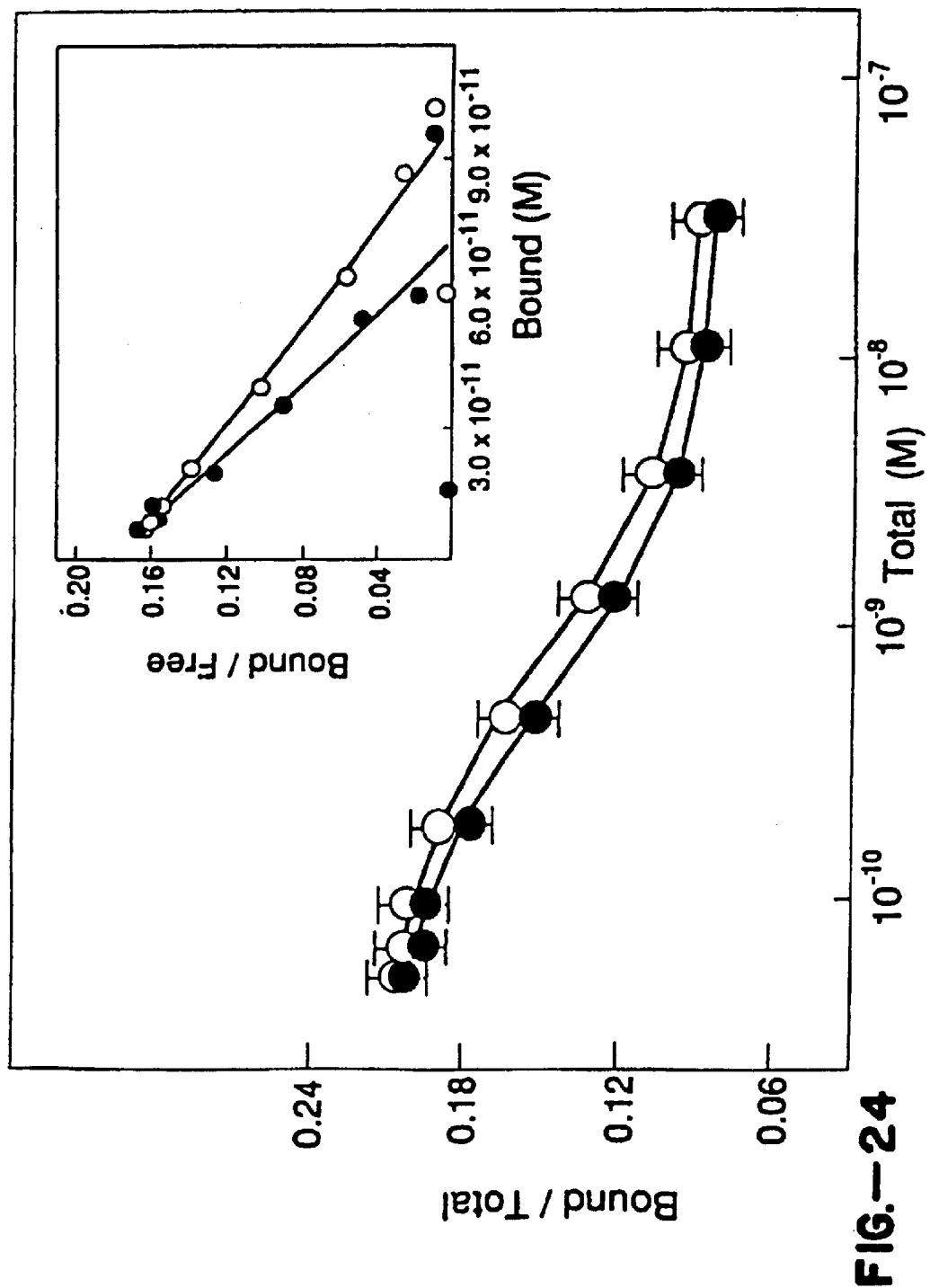
FIG. 24. Competitive binding curves of [$^{125}$I]hGH and cold hGH to the hGH binding protein isolated from either human serum (○) or from E. coli KS330 cultures expressing the plasmid phGHr(1–238) (●). Bars represent standard deviations from the mean. Inset shows Scatchard plots that were derived from the competitive binding curves. The concentrations of the binding protein from human serum and E. coli were 0.1 and 0.08 nM, respectively.

To compare the specificity of the recombinant hGH binding protein from *E. coli* with the natural product isolated from human serum, the affinities were determined for wild-type and various hGH mutants:

Both proteins formed a specific stoichiometric complex with hGH (FIG. 24). As can be seen, the affinities for wild-type and mutants of hGH are nearly identical between the two binding proteins (right side column, supra). The recombinant hGH binding protein has a marginally higher affinity compared to the natural protein from human serum. This may reflect the greater purity and homogeneity of the recombinant protein. Both proteins had identical specificities as shown by the changes in binding affinities for four alanine mutants of hGH that disrupt binding to the hGH binding protein ($K_d$(mut)/$K_d$(wt) supra) The affinity of hGH for the binding protein extending to Tyr246 ($K_d$=0.36±0.08 nM) was virtually identical to that terminating after Gln238 (0.40±0.03 nM) indicating the last 8 residues (including the seventh cysteine in the molecule) are not essential for binding hGH.

EXAMPLE 4

Receptor and Monoclonal Antibody Binding Assay

Purified hGH or hGH variants (over 95% pure) were assayed for binding to the soluble hGH receptor of Example 3. Laser densitometric scanning of Coomassie stained gels after SDS-PAGE was used to quantitate the concentration of the purified hormones. These values were in close agreement with concentrations determined from the absorbance at 280 nm ($\epsilon 2_{80}{}^{0.1\%}$=0.93). The dissociation constants ($K_d$) were calculated from Scatchard analysis for competitive displacement of [$^{125}$I] hGH binding to the soluble gGH receptor at 25° C. The $^{125}$I hGH was made according to the method of Spencer, S. A., et al. (1988) *J. Biochem.* 263, 7862.

TABLE X(B)

| | $K_d$ (nM) + S.D.[a] for hGH binding protein from: | | | | |
|---|---|---|---|---|---|
| hGH mutant | Human serum | $\frac{K_d (mut)}{K_d (wt)}$[b] | *E. coli* | $\frac{K_d (mut)}{K_d (wt)}$[b] | $\frac{K_d (human\ serum)}{K_d (E.\ coli)}$[b] |
| wt | 0.55 ± 0.07 | — | 0.40 ± 0.03 | — | 1.4 |
| I58A | 21 ± 2 | 38 ± 6 | 14 ± 1 | 36 ± 5 | 1.5 |
| R64A | 12 ± 1 | 22 ± 4 | 11 ± 1 | 28 ± 5 | 1.1 |
| E174A | 0.27 ± 0.04 | 0.49 ± 0.11 | 0.16 ± 0.01 | 0.4 ± 0.1 | 1.7 |
| F176A | 71 ± 7 | 130 ± 20 | 48 ± 5 | 120 ± 20 | 1.5 |

[a]Values of $K_d$ and corresponding standard deviations (SD) were determined by competitive binding analysis (FIG. 24) with wild-type hGH (wt) and a number of mutants of hGH.
[b]Reduction in binding affinity calculated from the ratio of dissociation constants for the hGH mutant (mut) and wild-type hGH for each hGH binding protein.
[c]Ratio of dissociation constants for the two hGH binding proteins with a given hGH type.

An enzyme-linked immunosorbent assay (ELISA) was used to assess the binding of eight different monoclonal antibodies to various segment-substituted and residue-substituted hGH variants. The following are the Mabs used:

| Mab | Identity | Source/Method |
|---|---|---|
| 1 | MabA | (*) |
| 2 | 33.2 | Hybritech, Inc. |
| 3 | Cat# H-299-01 | Medix Biotech, Inc. |
| 4 | 72.3 | Hybritech, Inc. |
| 5 | Cat# H-299-02 | Medix Biotech, Inc. |
| 6 | Mab 653 | Chemicon |
| 7 | Mab D | (*) |
| 8 | Mab B | (*) |

(*) Carbone, F. R., et al. (1985) J. Immunol. 135, 2609

Rabbit polyclonal antibodies to hGH were affinity purified and coated onto microtiter plates (Nunc plates, InterMed, Denmark) at 2 μg/mL (final) in 0.005 M sodium carbonate pH (10) at 24° C. for 16–20 h. Plates were reacted with 0.1 μg/mL of each hGH variant in buffer B (50 mM TRIS HCl Tris(hydroxymethyl)aminomethane hydrochloride [pH 7.5], 0.15 M NaCl, 2 mM EDTA, 5 mg/mL BSA, 0.05% TWEEN 20™ brand polyoxyethylene sorbitanmonolaurate 0.02% sodium azide) for two hours at 25° C. Plates were washed and then incubated with the indicated Mab which was serially diluted from 150 to 0.002 nM in buffer B. After two hours plates were washed, stained with horseradish peroxidase conjugated anti-mouse antibody and assayed. Values obtained represent the concentrations (nM) of each Mab necessary to produce half-maximal binding to the respective hGH variant.

Competitive displacement of the hGH receptor from hGH by anti-hGH Mabs was determined as follows. Assays were carried out by immobilization of wild-type hGH in microtiter plates coated with anti-hGH rabbit polyclonal antibodies as described. Receptor (fixed at 10 nM) and given anti-hGH Mab (diluted over a range of 150 to 0.002 nM) were added to the hGH coated microtiter plate for 16–20 hours at 25° C., and unbound components were washed away. The amount of bound receptor was quantified by adding an anti-receptor Mab that was conjugated to horseradish peroxidase which did not interfere with binding between hGH and the receptor. The normalized displacement value was calculated from the ratio of the concentration of Mab necessary to displace 50% of the receptor to the half-maximal concentration of Mab necessary to saturate hGH on the plate. This value was used to compare the relative ability of each Mab to displace the receptor.

EXAMPLE 5

Active Domains for Somatogenic Receptor Binding

Figure 4:
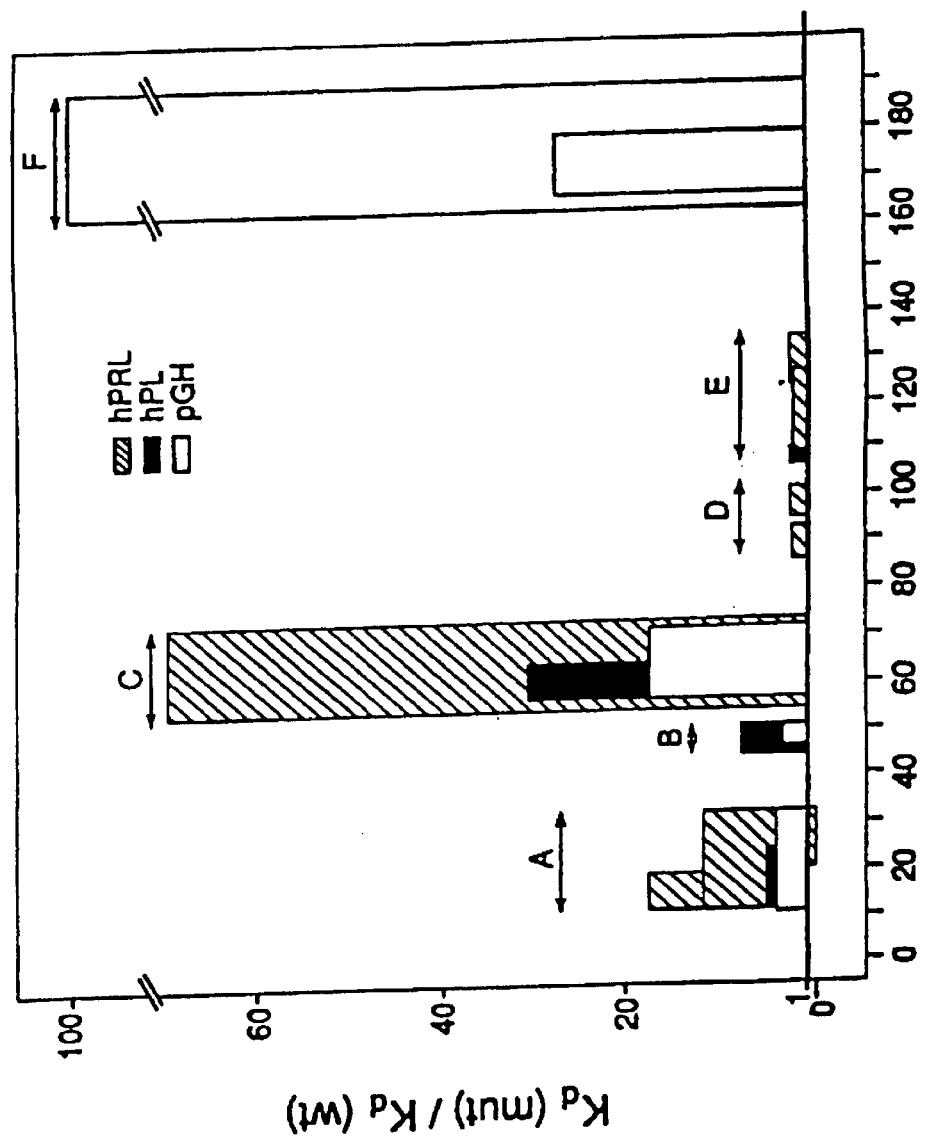
FIG. 4 is a bar graph showing the relative reduction in binding of various segment-substituted hGH variants to the soluble hGH receptor.
Figure 9:
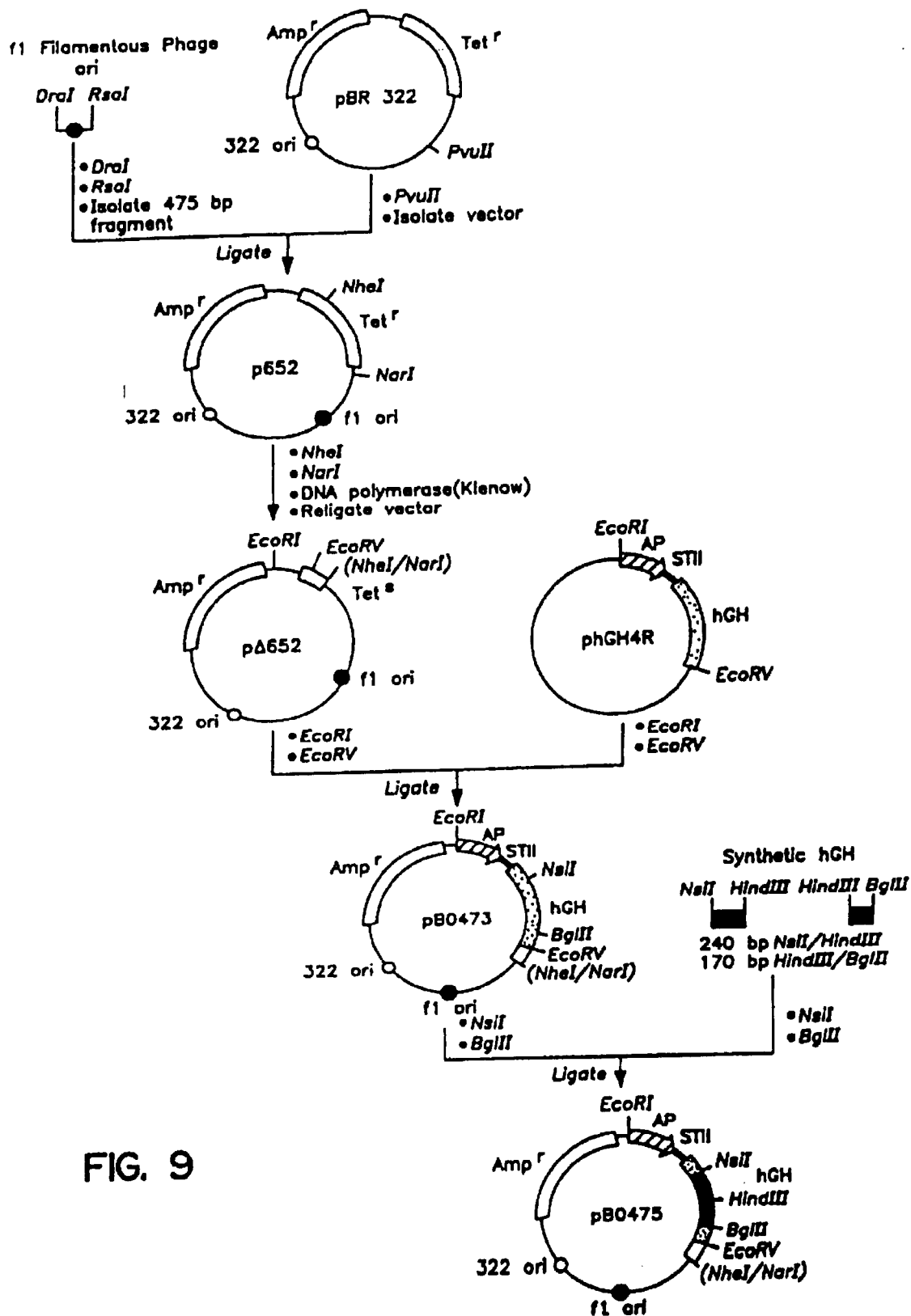
FIG. 9 depicts the construction of vector pB0475 which contains a synthetic hGH gene.

The 17 segment-substituted hGH variants described in Example 1 and Example 2 were assayed for binding to the soluble somatogenic receptor of Example 3 and binding to the monoclonal antibodies as described in Example 4. The results of the binding assay to the somatogenic receptor are shown in Table III. As can be seen, the segment substitutions that are most disruptive to binding are within regions A, C and F of FIGS. 4 and 5. These regions were further directed into smaller segments to further localize the active domains of the hGH molecule involved in binding to the somatogenic receptor. The most significant results from Table III are shown in FIG. 4, which is a bar graph showing the relative reduction in binding to the soluble hGH receptor as a consequence of the substitution of the indicated analogous sequences from the analogs hPRL, hPL and pGH as shown. Three active domains were identified as regions A, C and F comprising amino acid residues 12–19, 54–74 and 164–190) respectively. These regions are identified in the three-dimensional representation of the hGH molecule in FIG. 5.

As can be seen, the three active domains, A, C and F, although discontinuous in the amino acid sequence of hGH, form a continuous region in the folded molecule which defines the somatogenic binding site on hGH.

EXAMPLE 6

Epitope Mapping of hGH

The binding of the eight different monoclonal antibodies to specific segment-substituted hGH variants is shown in Table XI.

TABLE XI

| | Mab | | | | | | | |
|---|---|---|---|---|---|---|---|---|
| hGH Variant | 1 MCA | 2 Hybr 33.2 | 3 Medix 1 | 4 Hybr 72.3 | 5 Medix 2 | 6 Chemicon | 7 MCD | 8 MCB |
| wt hGH | 0.4 | 0.4 | 0.1 | 0.05 | 0.2 | 0.2 | 0.08 | 0.1 |
| hPL(12–25) | 0.4 | 0.4 | >75 | >50 | 0.2 | 0.2 | 0.08 | 0.1 |
| pGH(11–33) | 0.4 | >100 | 1.5 | 0.05 | 0.2 | 0.2 | 0.08 | 0.1 |
| hPRL(12–33) | 0.4 | >100 | >75 | >50 | 0.2 | 0.2 | 0.08 | 0.1 |
| hPRL(12–19) | 0.4 | >12 | >75 | >50 | 0.2 | 0.2 | 0.08 | 0.1 |
| hPRL(22–33) | 0.4 | 0.4 | 0.1 | 0.05 | 0.2 | 0.2 | 0.08 | 0.1 |
| hPL(46–52) | 0.4 | 0.4 | 0.1 | 0.05 | 0.2 | 0.2 | 0.40 | 0.1 |
| pGH(48–52) | 0.4 | 0.4 | 0.1 | 0.05 | 0.2 | 0.2 | 0.08 | 0.1 |
| hPL(56–64) | 0.4 | 0.4 | 0.1 | 0.05 | 0.2 | 0.8 | 0.08 | 0.1 |
| pGH(57–73) | 0.4 | 0.4 | 0.1 | 0.05 | >200 | >200 | 0.08 | 0.1 |
| hPRL(54–74) | 0.4 | 0.4 | 0.1 | 0.05 | 0.2 | 0.6 | 0.08 | 0.1 |
| hPRL(88–95) | >400 | 0.4 | 0.1 | 0.05 | 0.2 | 0.2 | 0.08 | 0.1 |
| hPRL(97–104) | >400 | >12 | 0.1 | 0.05 | 0.2 | 0.2 | 0.08 | 0.1 |
| hPL(109–112) | >12 | 0.4 | >75 | 15 | 0.2 | 0.2 | 0.08 | 0.1 |
| hPRL(111–129) | >12 | 0.4 | >75 | >50 | 0.2 | 0.2 | 0.08 | 0.1 |
| hPRL(126–136) | 0.4 | 0.4 | 0.1 | 0.05 | 0.2 | 0.2 | 0.08 | 0.1 |
| pGH(164–190) pGH(167–182) | 0.4 | 0.4 | 0.5 | 0.3 | >25 | 12.5 | 0.20 | 0.4 |

TABLE XI-continued

|  | Mab | | | | | | | |
| --- | --- | --- | --- | --- | --- | --- | --- | --- |
| hGH Variant | 1 MCA | 2 Hybr 33.2 | 3 Medix 1 | 4 Hybr 72.3 | 5 Medix 2 | 6 Chemicon | 7 MCD | 8 MCB |
| hGH(Δ32–46) | 0.4 | 0.4 | 0.1 | 0.05 | 0.2 | 0.2 | >100 | >100 |
| N12A | 0.4 | 0.4 | >75 | >50 | 0.2 | 0.2 | 0.08 | 0.1 |
| C182A | 0.4 | 0.4 | 0.1 | 0.05 | 2.0 | 0.2 | 0.08 | 0.1 |

With the possible exception of the pGH (167–190) variant, disruption of binding to each monoclonal antibody was dramatic and highly selective. FIGS. 13 through 20 localize the epitope for each of the Mabs on the three-dimensional structure of hGH. FIG. 6 comprises these epitopes to the binding site for the somatogenic receptor.

Figure 13:
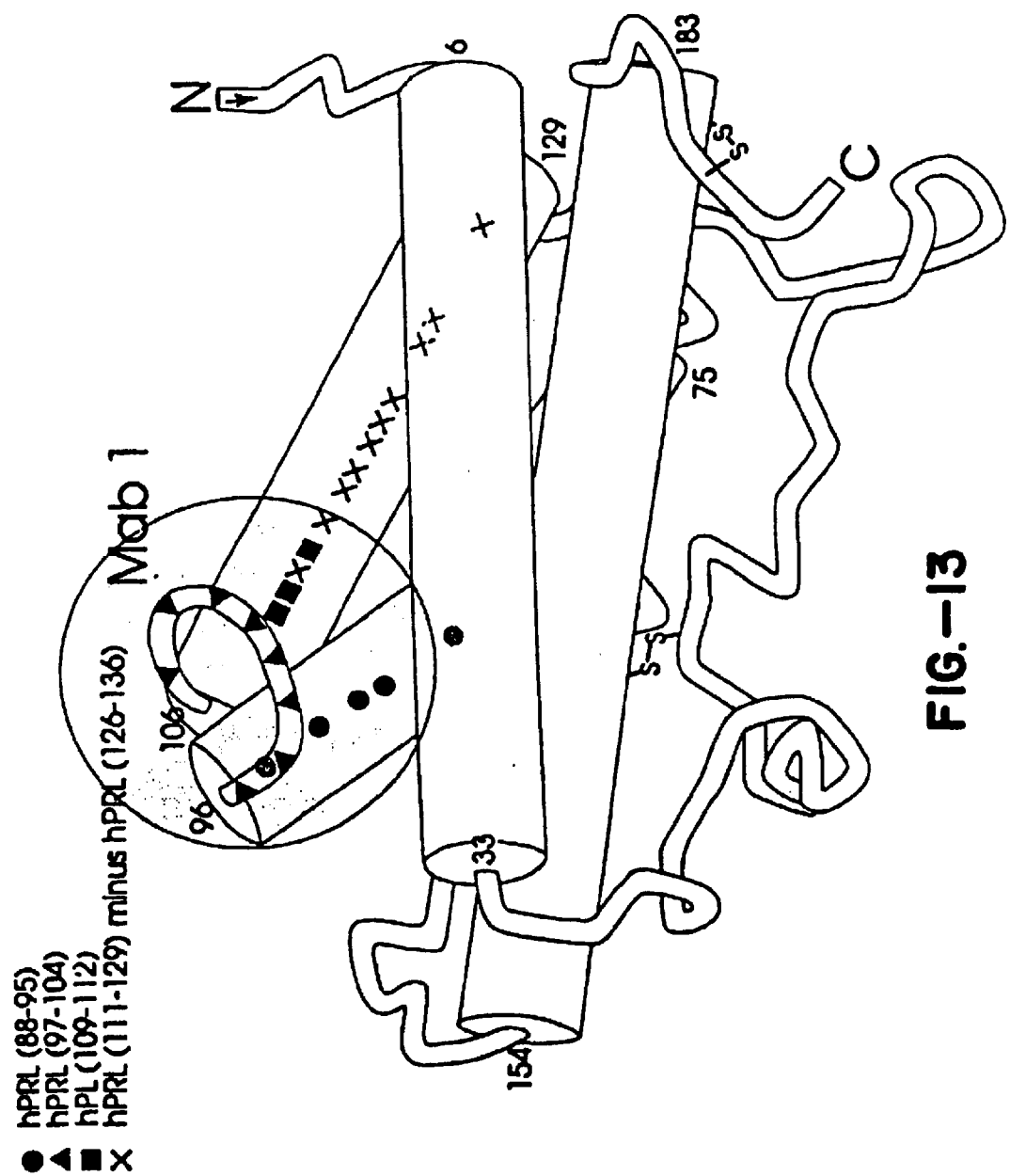
FIGS. 13 through 20 depict the epitope binding sites on hGH for each of eight different monoclonal antibodies.
Figure 14:
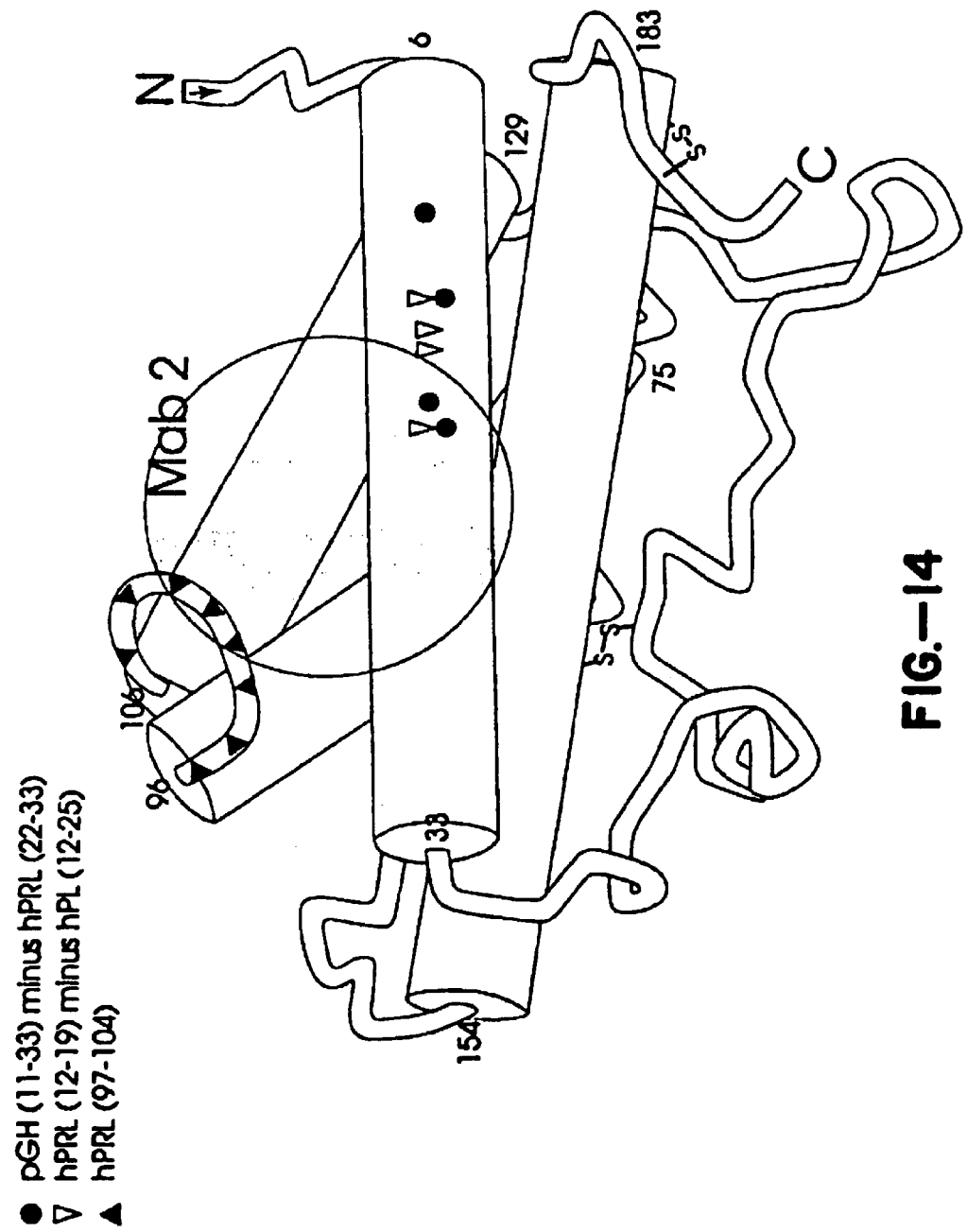
Figure 15:
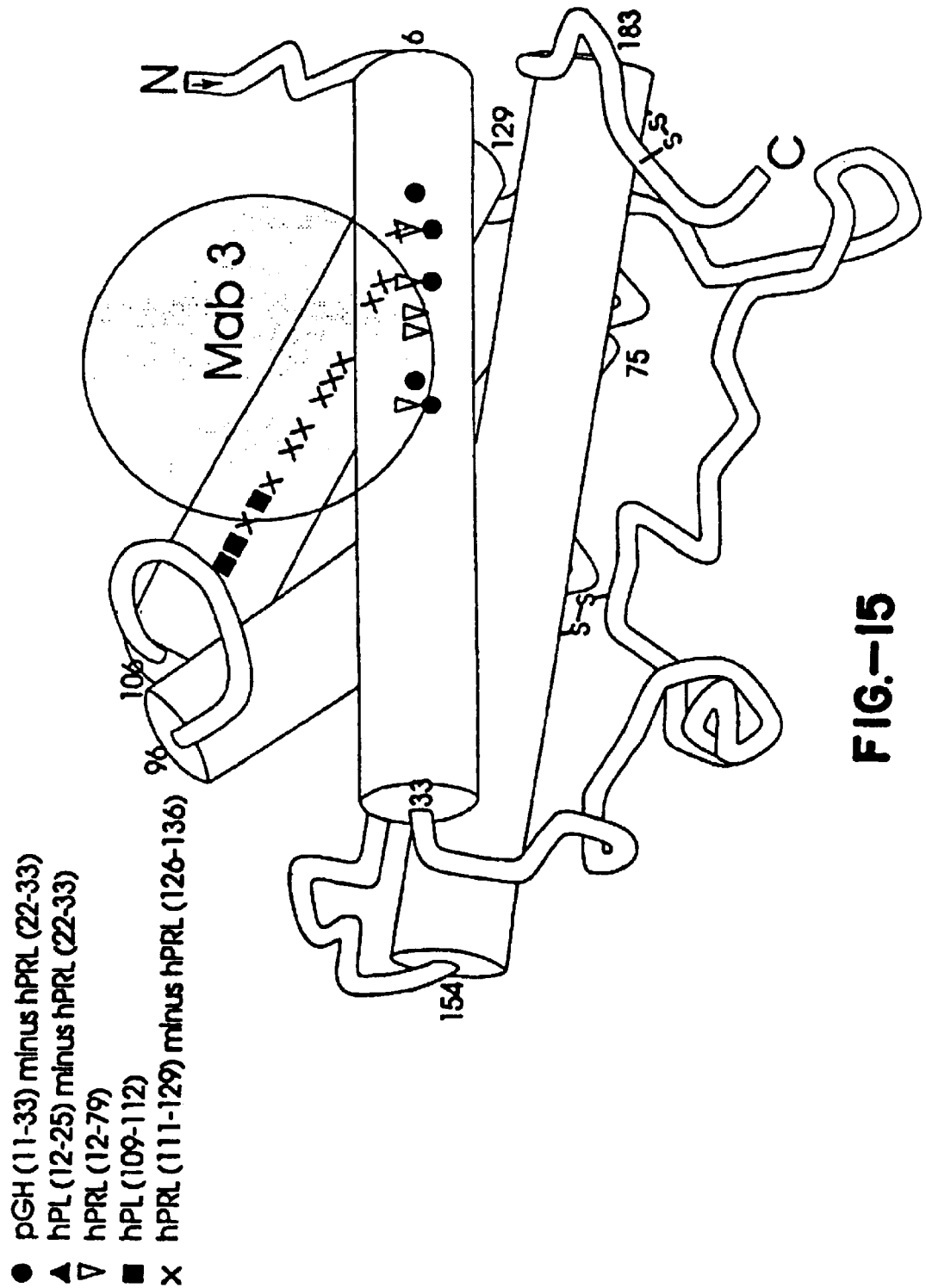
Figure 16:
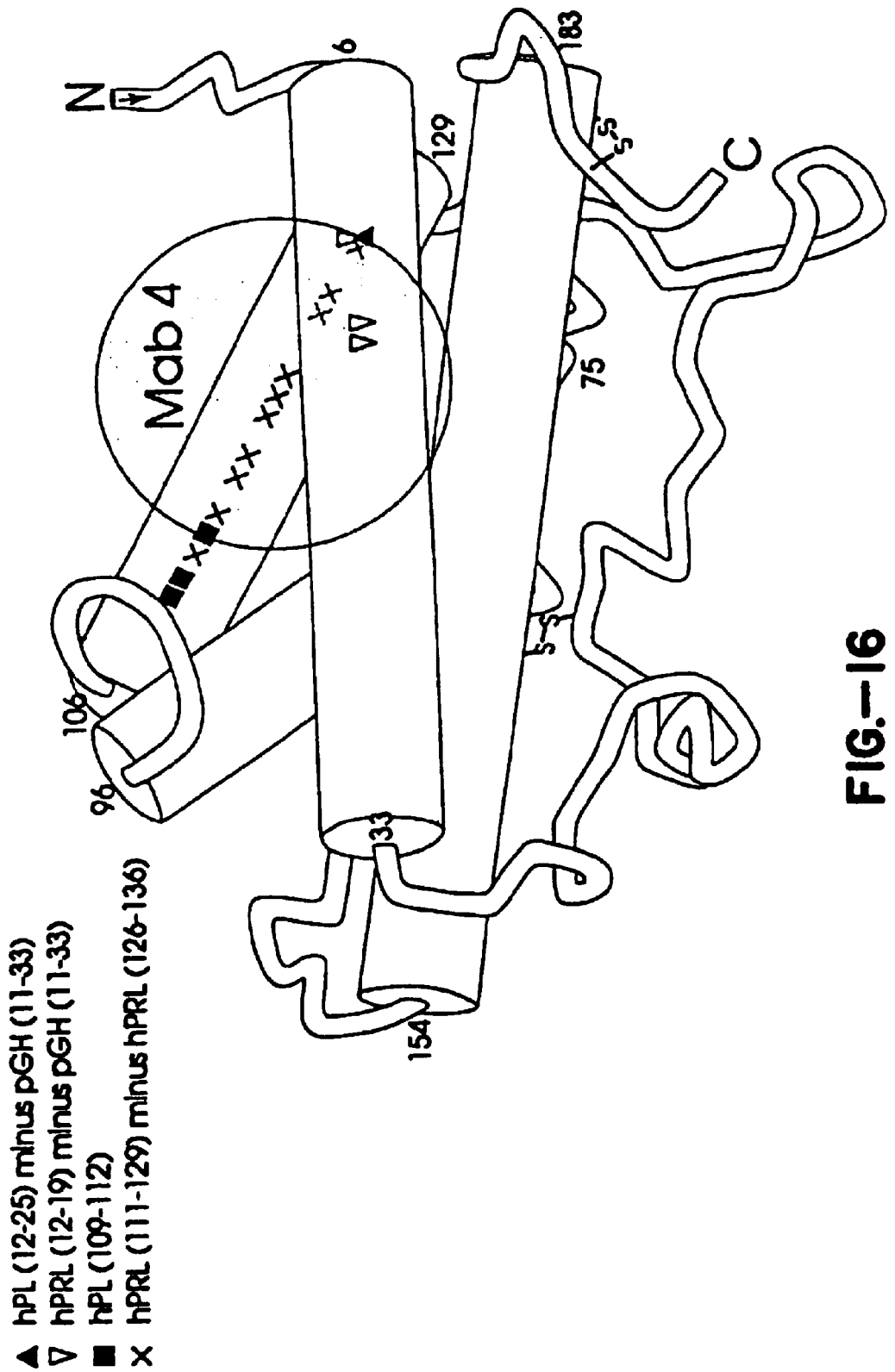
Figure 17:
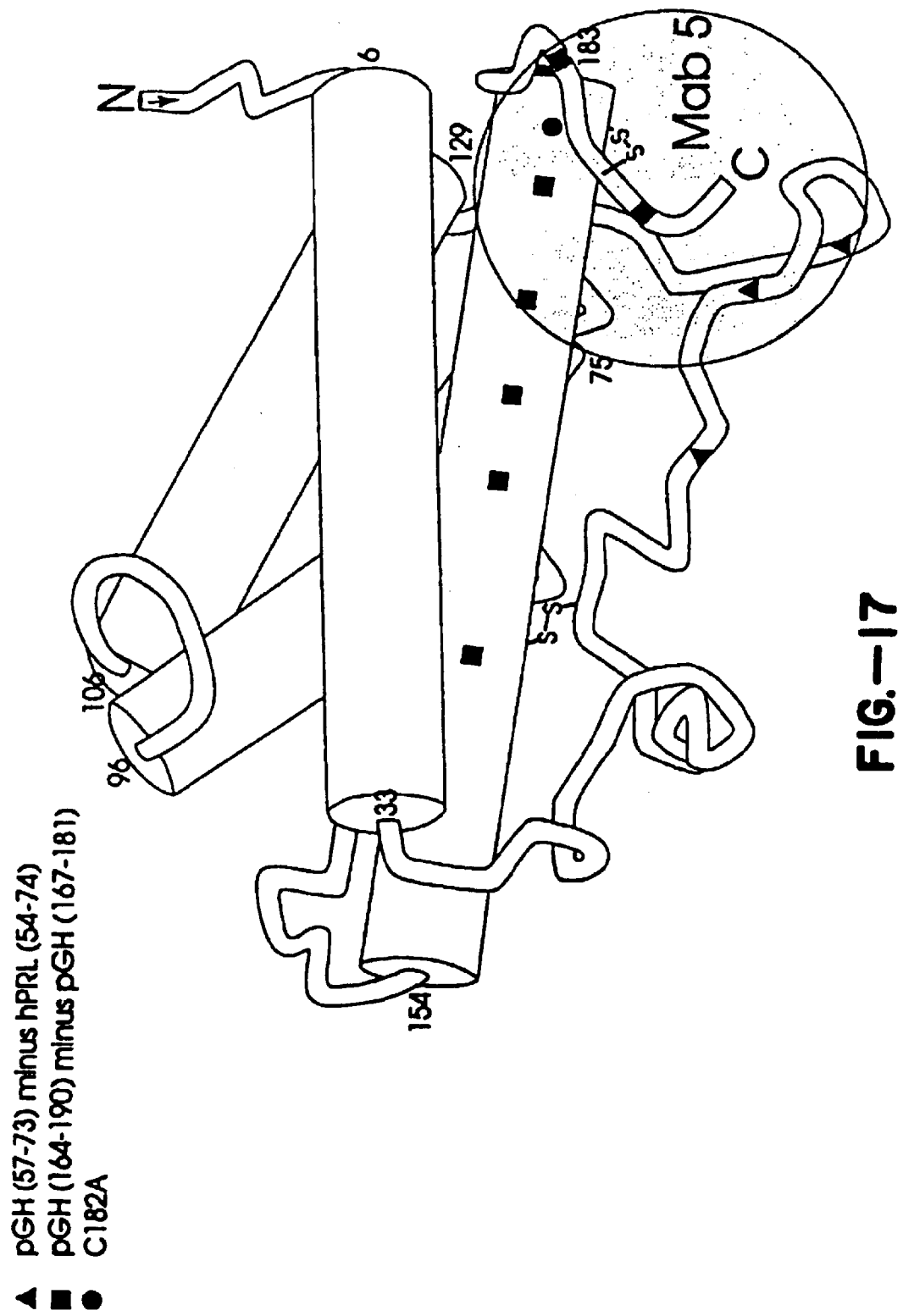
Figure 18:
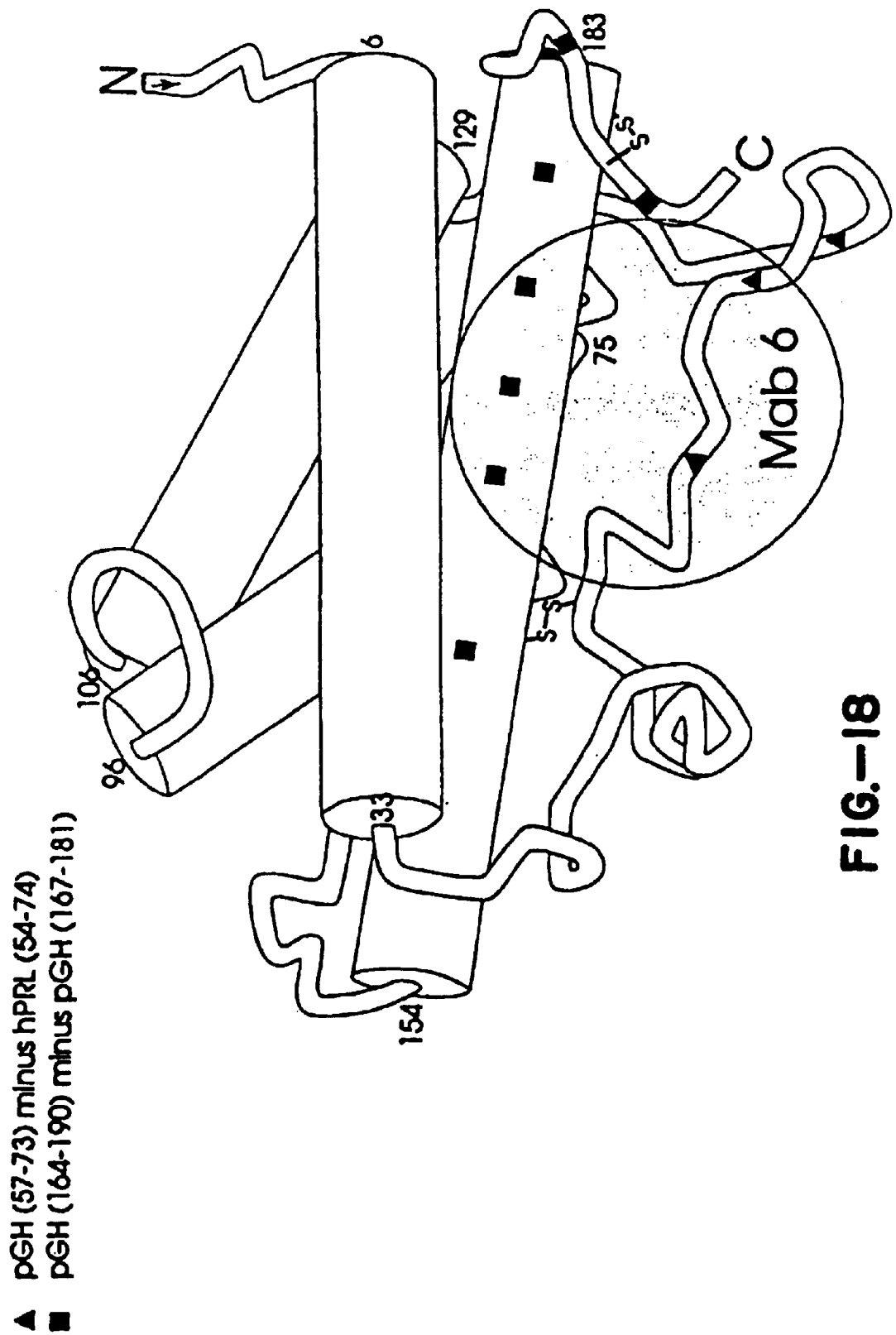
Figure 19:
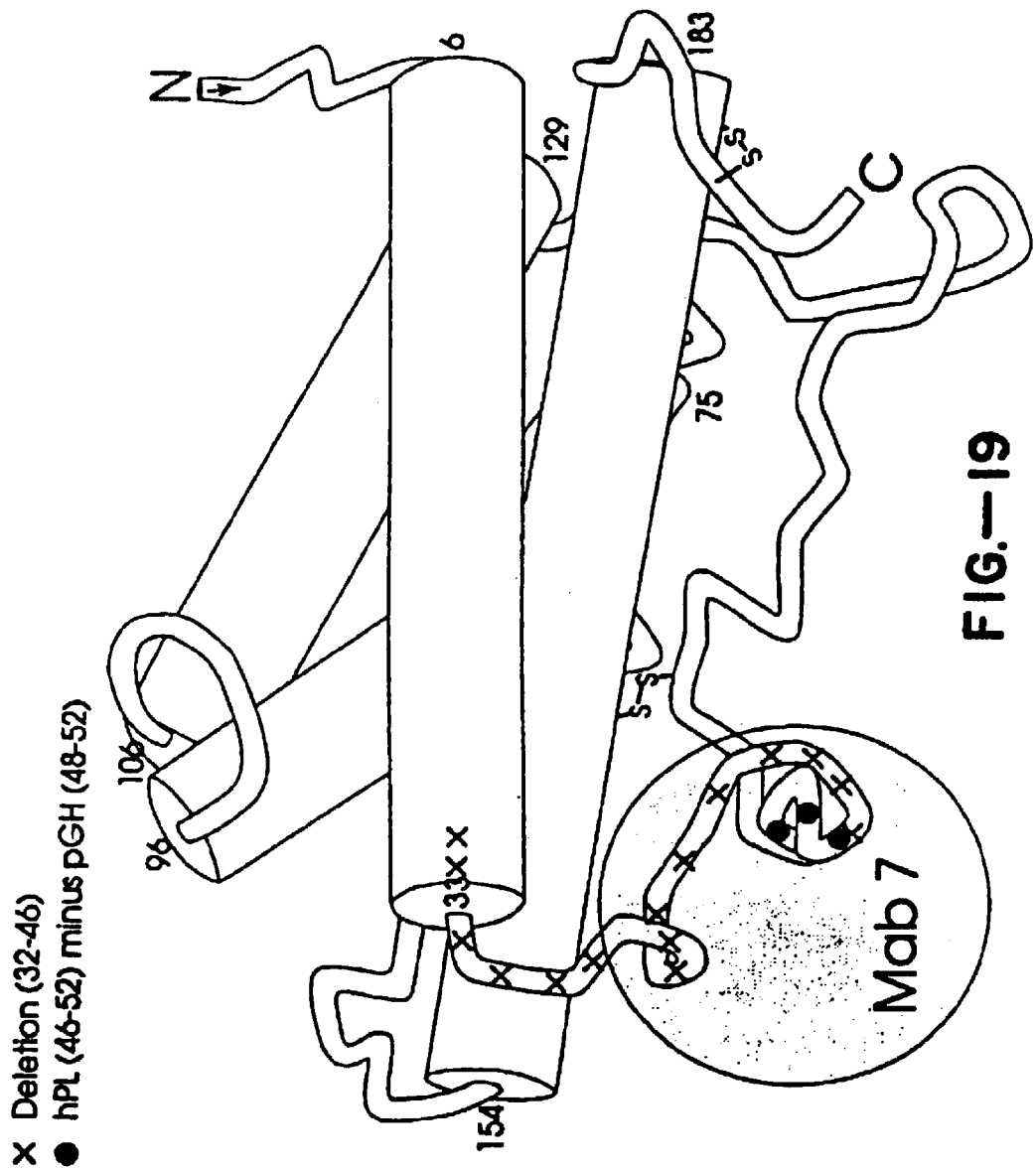
Figure 20:
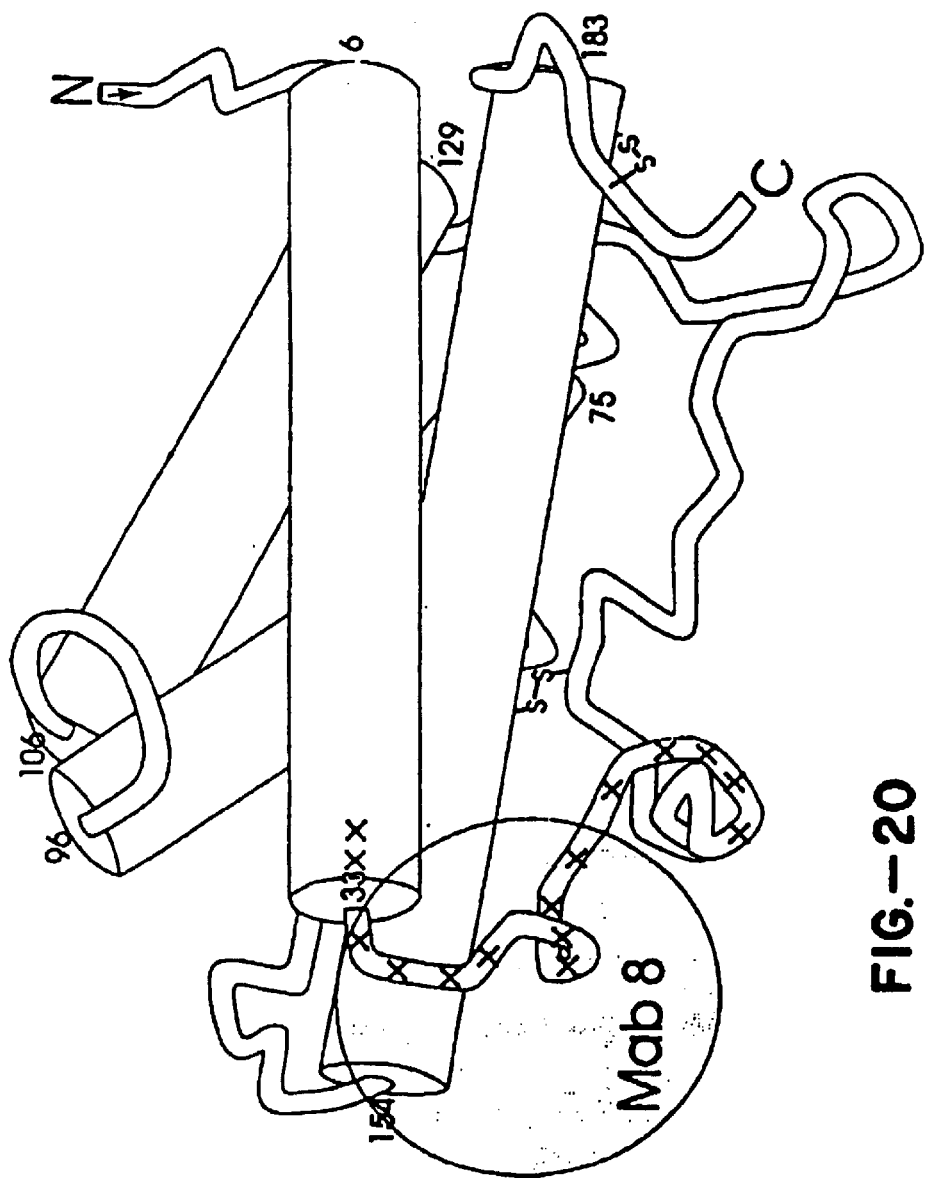

For example, the hPRL (88–95), hPRL (97–104), hPL (109–112) and hPRL (111–129) variants do not bind to Mab1, yet the other segment-substituted hGHs outside of these regions bound as effectively as wild-type hGH. Binding to Mabs 2, 3, 4, 5 and 6 was disrupted by mutations in discontinuous regions in the primary sequence but in close proximity in the folded hormone (see FIGS. 6 and 14 through 19). In contrast, Mabs 1, 7 and 8 were disrupted by mutations defined by a continuous sequence as shown in FIGS. 13, 19 and 20.

The regions disrupting binding to a given monoclonal antibody were further analyzed by dissecting specific segment-substituted hGH variants into subdomains or by analyzing variants that had common substitutions that still bound to the particular Mab. For example, pGH (11–33) retained tight binding to Mab 4 yet hPRL (12–33) disrupted binding. Thus, the disruptive mutations in the hPRL (12–33) variant can be confined to residues not mutated in pGH (11–33): N12, L15, R16, D26 and E30. This set can be further restricted to N12, L15 and R16 because the hPRL (12–19) variant disrupts binding, but the hPRL (22–23) variant does not (see FIG. 16). The N12H mutation in hPL (12–25) can entirely account for the disruption in binding to Mab 4 because this is the only mutation not in common with pGH (11–33). This was tested by substituting alanine for Asn-12. The binding of Mabs 3 or 4 to the N12A residue-substituted hGH variant was reduced by over 100-fold whereas binding to the other Mabs was unaffected.

Using this set of hGH variants, it was possible to resolve the epitopes from all eight Mabs even though binding for most of these Mabs was blocked by a common set of mutations. For example, although hPRL (12–19) disrupted binding to Mabs 2, 3 and 4, other variants indicated that these Mabs recognized different structures. Specifically, Mabs 2 and 3 were blocked by pGH (11–33) yet Mab 4 was unaffected. Binding of Mabs 3 and 4 was blocked by hPL (12–25) yet binding to Mab 2 was unaffected. Thus, the eight antibodies may have epitopes that overlap but none superimposed. Mutations that disrupt binding are present in both helices and loops and are always in close proximity in the folded hormone.

Collectively, the epitopes with a set of eight Mabs cover most of the hormone. However, there are still regions where these Mabs did not bind. For example, three of the 20 variants did not significantly disrupt binding to any of the Mabs tested (hPRL (22–33), pGH (48–52) and hPRL (126–136)).

There are significant differences between the antibody epitopes and the receptor binding site. Firstly, the patch defined by disruptive mutations is larger for the receptor than for any of the Mabs. A second difference is that the receptor has more tolerance to disruptive substitutions in the hormone than do the Mabs. This is evidenced by the fact that the maximum reduction in binding to the receptor for any of the mutants is about 70-fold, whereas almost every antibody has at least one variant that causes more than a 1000-fold reduction in binding, some of which may be the result of single substitutions such as N12A.

EXAMPLE 7

Competitive Binding of Mabs and shGHr

Many of the variants which cause disruption of receptor binding also disrupt the binding of one or more of the Mabs. The ability of each of the eight Mabs to block the binding of the hGH receptor to hGH was therefore evaluated. Results of this assay are shown in Table XII.

TABLE XII

| Mab | 50% binding to hGH† | displace 50% of receptor | $\left[\dfrac{\text{Normalized displacement}}{\text{conc. for 50\% displacement}}\right]$ conc. for 50% binding |
| --- | --- | --- | --- |
| 1 | 0.4 | >150 | >375 |
| 2 | 0.4 | 0.8 | 2 |
| 3 | 0.1 | 150 | 1500 |
| 4 | 0.05 | 150 | 3000 |
| 5 | 0.2 | 0.2 | 1 |
| 6 | 0.2 | 0.2 | 1 |
| 7 | 0.08 | 0.4 | 5 |
| 8 | 0.1 | >150* | >1500 |

*Binding of Mab 8 appears to slightly enhance binding of receptor to hGH.
†Data from Table X for binding of each Mab to hGH.

As can be seen Mabs 5 and 6 are the most efficient at blocking binding of the hGH receptor. This is because these Mabs have antigenic determinants located in the loop from residues 54 through 74 and in helix 4, closely overlap determinants for the receptor (see FIGS. 5, 6, 17 and 18). Mab 2 was the next most competitive antibody and it too shared a common disruptive mutation with the receptor (hPRL (12–19)). In contrast, Mabs 3 and 4 were roughly 1000-fold less competitive than Mab 2 yet they also shared overlapping disruptive mutations with the receptor in helix 1. See FIGS. 15 and 16. This apparent discrepancy may be easily reconciled if the mutations in helix 1 that disrupt Mabs 3 and 4 differ from those residues which disrupt binding to Mab 2 or the receptor. Indeed, one such mutant (N12A) disrupts binding of either Mab 3 or 4 without affecting binding to Mab 2 or the receptor.

Mab 7 competes relatively strongly with the receptor for hGH and it is disrupted by segment-substituted hGH variants that cause a minor disruption of receptor binding, e.g., hPL (46–52). Thus, it appears that Mabs 2 and 7 sit on the border of the receptor binding site. Mabs 1 and 8 were unable to give detectable displacement of the receptor, and as expected these contain no overlapping antigenic determinants with the receptor. These competitive binding data taken together with the direct epitope mapping and receptor binding data strongly support the general location of the receptor binding site as shown in FIG. 5.

EXAMPLE 8

Receptor Active Amino Acid Residues

The analysis of hGH in Examples 5, 6 and 7 implicates the amino terminal portion of helix 1 (residues 11–19) as being of moderate importance to receptor binding. In addition, residues 54–74 and 167–191 were identified as being important to receptor binding. Identification of which amino acids in these domains are active in receptor binding was carried out by analyzing a total of 63 single alanine variants. See Tables XIII, XIV and XV.

TABLE XIII

Amino acid scanning of positions 2–19 in hGH

| Variant | $K_d$ (nM) | $K_d$ (variant)/$K_d$ (wt) |
|---|---|---|
| wt | 0.34 | 1.0 |
| P2A | 0.31 | 0.90 |
| T3A | 0.31 | 0.90 |
| I4A | 0.68 | 2.0 |
| P5A | 0.71 | 2.1 |
| L6A | 0.95 | 2.8 |
| S7A | 0.61 | 1.8 |
| R8A | 0.48 | 1.4 |
| L9A | 0.32 | 0.95 |
| F10A | 2.0 | 5.9 |
| D11A | NE | — |
| N12A | 0.40 | 1.2 |
| A13 (WT) | | |
| M14A | 0.75 | 2.2 |
| L15A | 0.44 | 1.3 |
| R16A | 0.51 | 1.6 |
| A17 (WT) | | |
| H18A | 0.24 | 0.71 |
| R19A | 0.37 | 1.1 |

TABLE XIV

Amino acid scanning of positions 54–74 in hGH

| Variant | $K_d$ (nM) | $K_d$ variant/$K_d$ WT |
|---|---|---|
| WT | 0.31 | 1.0 |
| F54A | 1.5 | 4.4 |
| S55A | 0.41 | 1.2 |
| E56A | 1.4 | 4.1 |
| S57A | 0.48 | 1.4 |
| I58A | 5.6 | 17.0 |
| P59A | 0.65 | 1.9 |
| T60A | NE | — |
| P61A | NE | — |
| S62A | 0.95 | 2.8 |
| N63A | 1.12 | 3.3 |
| R64A | 7.11 | 21.0 |
| E65A | 0.20 | 0.6 |
| E66A | 0.71 | 2.1 |
| T67A | NE | — |
| Q68A | 1.8 | 5.2 |
| Q69A | 0.31 | 0.9 |
| K70A | 0.82 | 2.4 |
| S71A | 0.68 | 2.0 |
| N72A | NE | — |
| L73A | 0.24 | 0.70 |
| E74A | NE | — |

TABLE XV

Amino acid scanning of positions 167–191 in hGH

| Variant | $K_d$ (nM) | $K_d$ variant/$K_d$ WT |
|---|---|---|
| WT | 0.34 | 1 |
| R167A | 0.26 | 0.75 |
| K168A | 0.37 | 1.1 |
| D169A | NE | — |
| M170A | NE | — |
| D171A | 2.4 | 7.1 |
| K172A | 4.6 | 14 |
| V173A | NE | — |
| E174A | 0.075 | 0.22 |
| T175A | NE | — |
| T175S | 5.9 | 16 |
| F176A | 5.4 | 16 |
| L177A | NE | — |
| R178A | NE | — |
| R178N | 1.4 | 4.2 |
| I179A | 0.92 | 2.7 |
| V180A | 0.34 | 1.0 |
| Q181A | 0.54 | 1.6 |
| C182A | 1.9 | 5.7 |
| R183A | 0.71 | 2.1 |
| S184A | 0.31 | 0.90 |
| V185A | 1.5 | 4.5 |
| E186A | 0.27 | 0.80 |
| G187A | 0.61 | 1.8 |
| S188A | 0.24 | 0.7 |
| C189A | NE | — |
| G190A | NE | — |
| F191A | 0.20 | 0.60 |

The substitution of alanine was extended to include residues 2–19 because of uncertainties in the position of the amino-terminal residue (Abdel-Meguid, S. S., et al. (1987) *Proc. Natl. Acad. Sci. USA* 84, 6434). Indeed, the most pronounced reduction in binding occurred for F10A (6-fold) followed by alanine substitutions at residues 4–6 at the N-terminus of helix 1 (see FIG. 21). Substantially larger effects on binding (greater than 20-fold) occurred for specific alanine substitutions within the -54 to 74 loop and the carboxy, terminal sequence 167–191. For several alanine variants, binding was enhanced up to 4.5-fold. The most dramatic example was E174A, which was located in the midst of a number of disruptive alanine mutations. See FIG. 4, 7 and 21.

Figure 21:
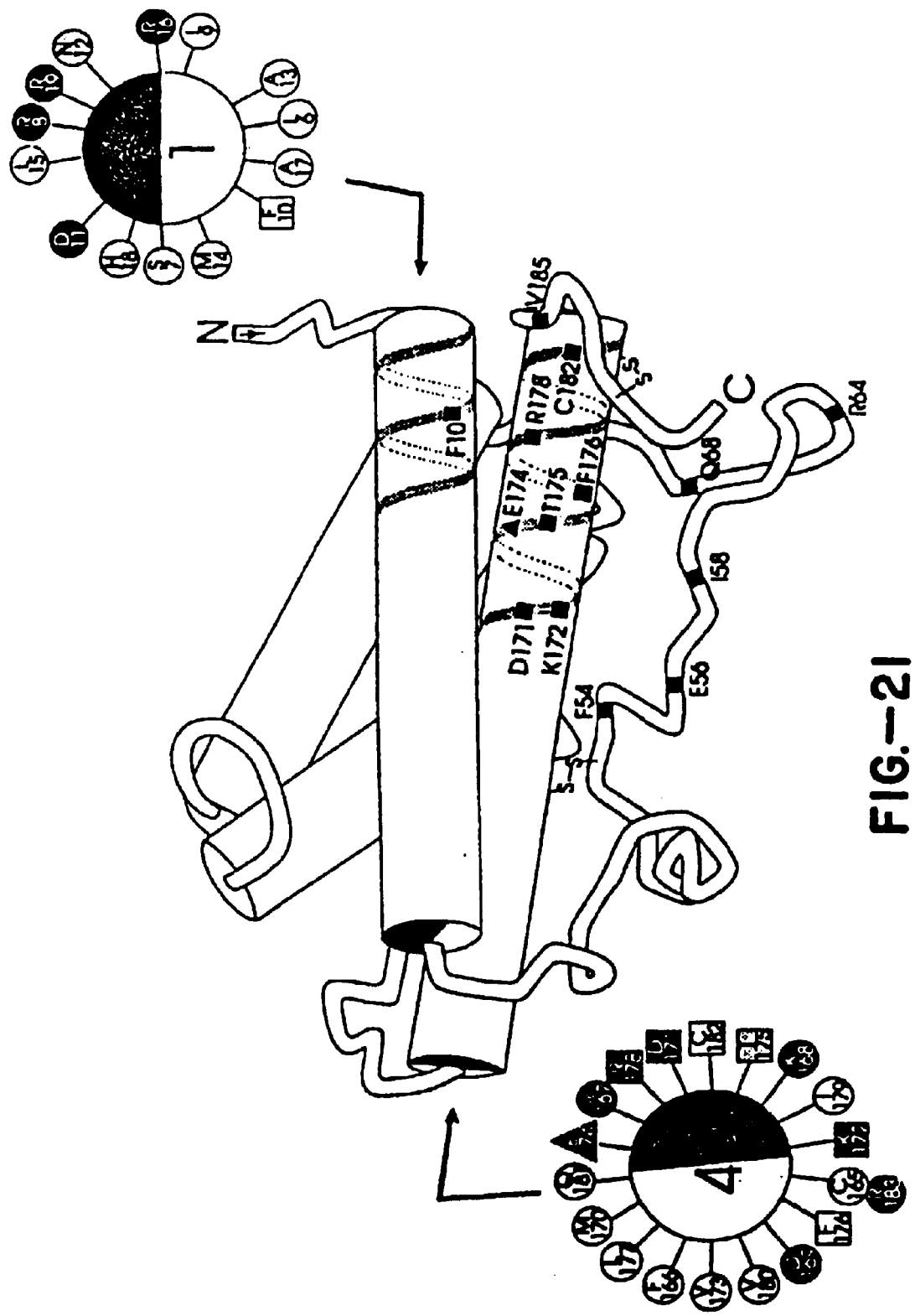
FIG. 21 shows the active amino acids involved in binding to the somatogenic receptor in hGH and helical wheel projections for helices 1 and 4.
Figure 22:
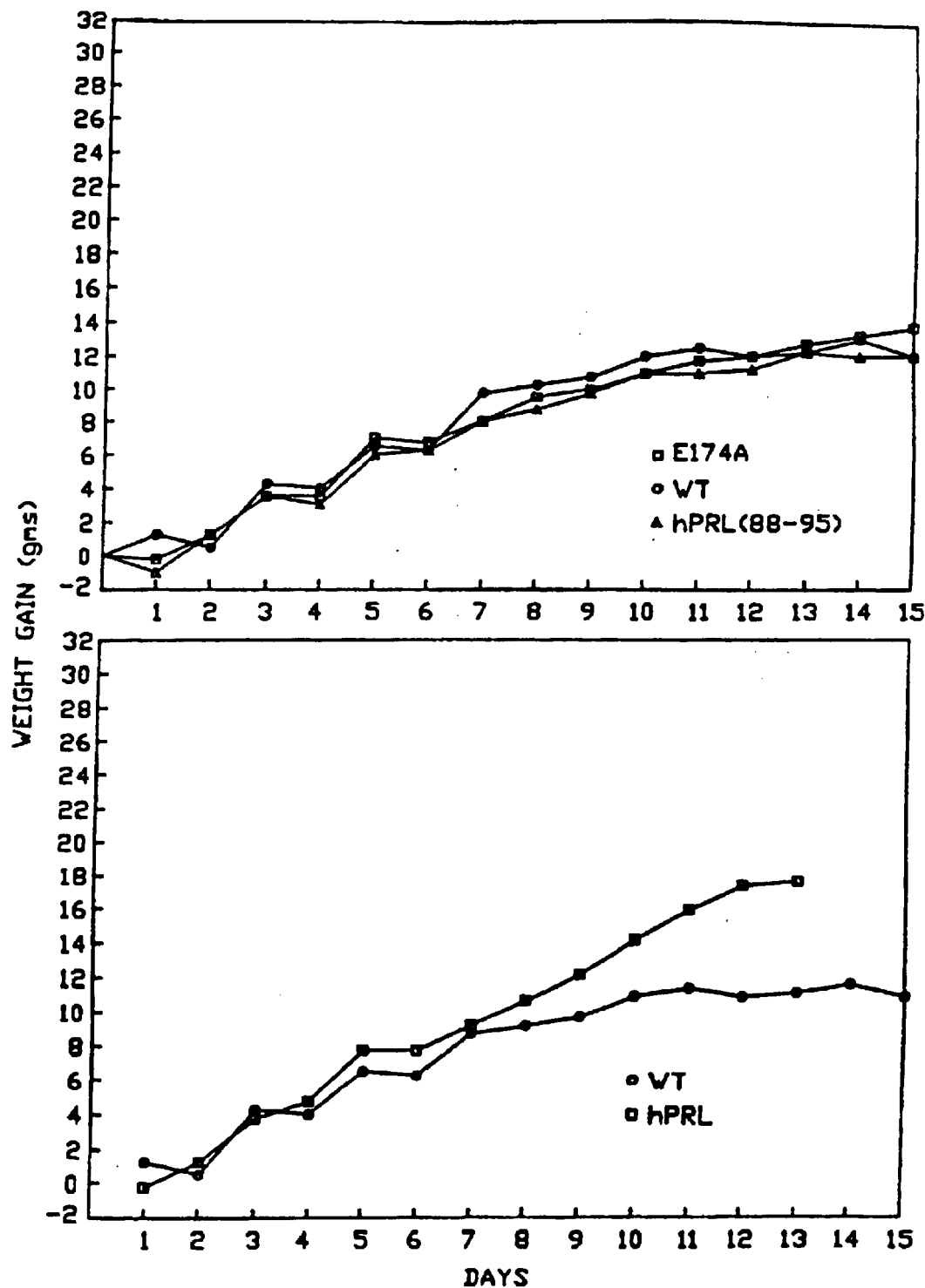
FIG. 22 shows the rat weight gain versus time for hGH and hGH, variants administered at 50 micrograms/kg/day. The top panel shows weight gain in rats treated with wild type hGH (WT), the E174A variant of hGH, and the segment-substituted hGH variant hPRL (88–95). The bottom panel shows weight gain in rats treated with wild type hGH as compared to hPRL.
Figure 23:
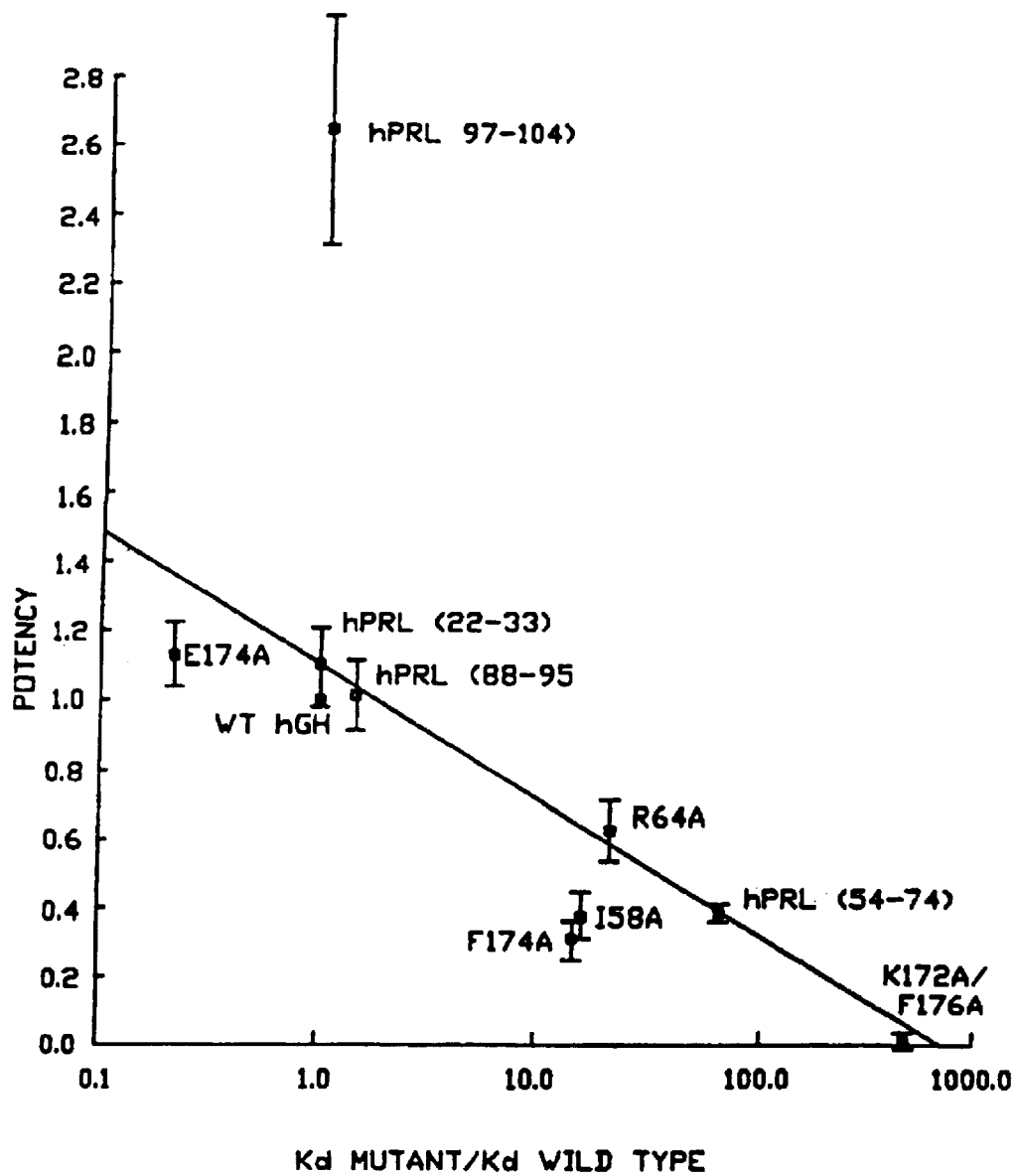
FIG. 23 is a semilog plot of Kd ratio versus potency for hGH variants as compared to wild-type hGH.

The most disruptive alanine substitutions form a patch of about 25 Å by 25 Å on the hormone that extends from F10 to R64 and from D171 to V185 (see FIG. 21). Furthermore, these side chains appear to be facing in the same direction on the molecule. For example, all of the alanine mutants that most affect binding on helix 4 (D171A, K172A, E174A, F176A, I179A, C182A and R183A) are confined to three and one-half turns of this helix, and their side chains project from the same face of the helix (see FIG. 21). Based upon this model, it was predicted that T175 and R178 should be involved in binding because they occupy a central position as shown in FIG. 21.

Although the T175A mutant could not be expressed in high enough yields in shake flasks to be assayed, a more conservative mutant (T175S) was. Accordingly, the T175S mutant caused a 16-fold reduction in receptor binding. Similarly, although R178A was poorly expressed, R178N could be expressed in yields that permitted analysis. R178N exhibited a greater than four-fold reduction in binding affinity.

The next most disruptive mutant in the carboxy terminus was V185A. Although V185A is outside of helix 4, it is predicted by the model to face in the same direction as the disruptive mutations within helix 4. In contrast, alanine mutations outside the binding patch, or within it facing in the opposite direction from those above (R167A, K168A, V180A, Q181A, S184A, E186A, S188A), generally had no or little effect on receptor binding.

A similar analysis applied to alanine mutants in helix 1, albeit with more moderate effects on binding. Within the helix, the alanine substitutions that most disrupted binding were at residue 6, 10 and 14 which were located on the same face of the helix. The least disruptive alanine mutations (L9A, N12A and L15A) were located on the opposite face of helix 1. This is further confirmed by the fact that anti-hGH Mabs 3 and 4, which do not compete with the receptor for binding to hGH, both bind to Asn-12. See Table XVI.

TABLE XVI

Binding of hGH and alanine variants to eight different anti-hGH monoclonal antibodies (Mab).

| | Mab | | | | | | | |
|---|---|---|---|---|---|---|---|---|
| Hormone | 1 | 2 | 3 | 4 | 5 | 6 | 7 | 8 |
| hGH | 0.4 | 0.4 | 0.1 | 0.05 | 0.2 | 0.2 | 0.08 | 0.1 |
| F10A | 0.4 | 0.4 | 0.1 | 0.05 | 0.2 | 0.2 | 0.08 | 0.1 |
| N12A | 0.4 | 0.4 | >75 | >50 | 0.2 | 0.2 | 0.08 | 0.1 |
| I58A | 0.4 | 0.4 | 0.1 | 0.05 | 0.2 | 0.2 | 0.08 | 0.1 |
| R64A | 0.4 | 0.4 | 0.1 | 0.05 | 0.2 | 1.6 | 0.08 | 0.1 |
| Q68A | 0.4 | 0.4 | 0.1 | 0.05 | 0.2 | 0.2 | 0.08 | 0.1 |
| K168A | 0.4 | 0.4 | 0.1 | 0.05 | 0.2 | 0.2 | 0.08 | 0.1 |
| D171A | 0.4 | 0.4 | 0.1 | 0.05 | 0.2 | 0.2 | 0.08 | 0.1 |
| K172A | 0.4 | 0.4 | 0.1 | 0.05 | 0.2 | 0.2 | 0.08 | 0.1 |
| E174A | 0.4 | 0.4 | 0.1 | 0.05 | 0.2 | 0.2 | 0.08 | 0.1 |
| F176A | 0.4 | 0.4 | 0.1 | 0.05 | 0.2 | 0.2 | 0.08 | 0.1 |
| C182A | 0.4 | 0.4 | 0.1 | 0.05 | 2.0 | 0.2 | 0.08 | 0.1 |
| V185A | 0.4 | 0.4 | 0.1 | 0.05 | 0.2 | 0.2 | 0.08 | 0.1 |

The relative positions of side chains within the 54–74 loop cannot be fixed in the model as they can be for those within helices 1 and 4. However, there is a striking periodicity in the binding data in which mutations of even-numbered residues cause large reductions in binding relative to odd-numbered residues. This is especially true for the first part of this region (54–59) and may reflect a structure in which even residues project toward the receptor and odd ones away.

EXAMPLE 9

Conformational Integrity and Binding Energetics of Alanine-Substituted hGH Variants Several lines of evidence indicate that the alanine substitutions that disrupt the receptor binding do not do so by causing the molecule to be misfolded. Firstly, the eight Mabs react as well with almost all of the alanine mutants that disrupt binding to the receptor as they do with hGH. See Table XII supra.

The exceptions are R64A and C182A which selectively disrupt binding to the anti-hGH Mabs 6 and 5, respectively. These two Mabs as previously indicated compete with the somatogenic receptor for binding to hGH. In addition, two alanine variants were made which do not affect receptor binding. One of these affects the binding of two Mabs (N12A) and the other affects none of the Mabs (K168A). This data indicates that binding to either the Mabs or receptors is disrupted by a very local perturbation in the structure of the variant. Moreover, the far UV circular dichroic spectra of all the hGH variants tested are virtually identical to wild-type hGH.

About 20% of the alanine mutants (D11A, T60A, P61A, T67A, N72A, E74A, D169A, M170A, V173A, T175A, L177A, K178A, C189A, G190A) were not secreted at high enough levels in shake flasks to be isolated and analyzed. Since genes encoding such variants were expressed in the same vector and expression was independent of the specific alanine codon, variations in steady-state expression levels most likely reflect differences in secretion level and/or proteolytic degradation of the hGH variants. Several of the non-expressing alanine variants in helix 4 are located on its hydrophobic face (M170A, V173A and L177A) as shown in FIG. 21 wherein the hydrophobic side of the helix is identified by open shading. However, this is not a general effect because several alanine substitutions were tolerated on the hydrophobic face of helix 1 (L6A, L9A and F10A) and helix 4 (F176A and V180A).

In addition, impaired expression of hGH variants was sometimes observed when charged or neutral amino acids were replaced with alanine (D11A, T60A, T67A, N72A, E74A, D169A, T175A, R178A). Mutations such as T175S and R178N, which preserved the hydrogen bonding group at those sites, could be expressed albeit at levels below wild-type. The non-expressing C189A variant disrupts the carboxy-terminal disulfide and its counterpart (C182A) was also expressed at levels far below wild-type. Several other non-expressing alanine mutants (T60A, T61A and T67A) were located in a loop structure. Thus, low levels of expression or non-expression can result from a multitude of structural effects but can be obviated by isosteric or isofunctional substitutions.

The substitutions that cause a ten fold or greater effect upon binding (I58A, R64A, K172A, T175S, F176A) are likely to be directly involved in binding. The strengths of hydrogen bonds or salt bridges present in nature (Fersht, A. R. (1972) *J. Mol. Biol.* 64, 497; Brown, L. R., et al. (1978) *Eur. J. Biochem.* 88, 87; Malivor, R., et al. (1973) *J. Mol. Biol.* 76 123) or engineered by site-directed mutagenesis experiments (Fersht, A. R., et al. (1985) *Nature* 314, 225; Bryan, P., et al. (1986) *Proc. Natl. Acad. Sci USA* 83, 3743; Wells, J. A., et al. (1987) *Proc. Natl. Acad. Sci USA* 84, 5167; Wells, J. A., et al. (1987) *Proc. Natl. Acad. Sci. USA* 84, 1219; Cronin, C. N., et al. (1987) *J. Am. Chem. Soc.* 109 2222; Graf, L., et al. (1988) *Proc. Natl. Acad. Sci. USA* 85 4961) overlap and range widely from 1 to 5 kcal/mole depending upon the microenvironment. For hGH, reductions in binding free energy of 0.8, 1.0, 1.2, 1.6 and 1.8 kcal/mol ($\Delta\Delta G_{binding}$=+RT in Kd (var)/Kd(wt)) occurred for alanine substitutions at E56, Q68, D171, K172 and R64, respectively. The energetics for burial of a hydrophobic side chain into a protein tends to parallel its free energy of transfer into ethanol (Estell, D. A., et al. (1986) *Science* 233, 659; Nozaki, Y. et al. (1980) in The Hydrophobic Effect (Wiley, N.Y. pp. 4–21)).

Accordingly, the reductions in binding free energies for F175A, F10A, F54A, I58A, and V185A were 1.6, 1.0, 0.9, 1.7 and 0.9 kcal/mol, respectively. These are slightly below the predicted change in hydrophobic free energy in going from Phe, Ile or Val to Ala of 2.0, 2.4 and 1.0 kcal/mol, respectively. By this analysis the effect of the T175S mutant ($\Delta\Delta G_{binding}$=1.6 kcal/mol) is larger than expected for loss of a γ methyl groups ($\Delta\Delta G_{hydrophobic}$=0.7 kcal/mol). To fully characterize the nature of the molecular contacts between hGH and its somatogenic receptor requires direct structural information. However, the energetics of binding of these alanine mutants shows them to be in the range of previous measurements made on contact residues in entirely different systems. In fact, the sum of binding free energies for these alanine-substituted variants exclusive of C182A that are most disruptive to receptor binding (−13.2 kcal/mol.) is comparable to the total free energy binding between hGH and its receptor (−13 kcal\mol).

EXAMPLE 10

Reactivity of hGH Variants with Anti-hGH Polyclonal Antibodies

The hGH variants hPRL (22–33), E174A and hPRL (88–95) were tested in a rat weight gain assay. The results of that assay are presented in FIG. 22. As can be seen, all the variants except hPRL (22–33) have a reduced potency after about 14 days of growth. The leveling off of growth is attributed to the development of antibodies to the various growth hormones which neutralize the biological effect. The fact that the hPRL (22–33) variant continues to induce growth suggests that it is not as immunogenic as wild-type hGH or the other variants used.

A comparison of the reactivity of various hGH variants with human and murine serum containing polyclonal antibodies to hGH is shown in Table XVII.

TABLE XVII

Serum Anti-hGH Antibodies Binding to hGH Variants

| | Average % of Reduction of Anti-PROTROPIN® brand hGH Binding ± SD | | % Incidence | |
|---|---|---|---|---|
| | Human Sera N = 22 | Mouse Sera (N = 6) | Human Sera | Mouse Sera |
| hGH | 0 | 0 | 100 | 100 |
| pGH 11–33 | 86 ± 13 | 65 ± 16 | 100 | 100 |
| hPRL 12–33 | 79 ± 19 | 52 ± 13 | 100 | 100 |
| hPL 12–25 | 35 ± 19 | 16 ± 11 | 81 | 33 |
| hPRL 12–19 | 29 ± 20 | 11 ± 12 | 71 | 33 |
| hPRL 22–33 | 69 ± 15 | 38 ± 8 | 100 | 100 |
| hPL 46–52 | 6 ± 8 | 2 ± 4 | 10 | 0 |
| pGH 48–52 | 7 ± 8 | 4 ± 4 | 10 | 0 |
| pGH 57–73 | 43 ± 15 | 39 ± 12 | 95 | 100 |
| hPRL 54–74 | 14 ± 9 | 8 ± 7 | 24 | 0 |
| D80 | 13 ± 15 | 7 ± 7 | 14 | 0 |
| hPRL 88–95 | 14 ± 22 | 4 ± 5 | 19 | 0 |
| hPL 109–112 | 10 ± 11 | 9 ± 9 | 24 | 17 |
| hPRL 126–136 | 8 ± 12 | 2 ± 2 | 19 | 0 |
| C182A | 1 ± 5 | 1 ± 3 | 5 | 0 |

As can be seen, variants containing substitutions within the region from residues 22 to 33 have substantially reduced binding activity, and in some cases no activity, with individual human and mouse anti-serum for wild-type hGH.

Except for the variant pGH 57–73, variants containing substitutions in the other regions shown do not have a significant reduction in reactivity. Since the segment-substituted mutants between residues 11 and 33 retain their ability to bind the somatogenic receptor, such variants demonstrate the production of variants which maintain the ability to promote somatogenesis but have another property which is modified, in this case reactivity with anti-hGH polyclonal antibodies.

EXAMPLE 11

Relationship Between $K_d$ and Potency

A semi-log plot of the ratio of $K_d$ (variant)/$K_d$ (wild type) for specific hGH variants versus the potency of such variants in a rat weight gain assay is shown in FIG. 23. As can be seen a linear relationship exists which suggests that a decreased-binding affinity for the somatogenic receptor will result in a decrease in potency.

As can be seen, the hGH variant E174A has a higher binding affinity for the somatogenic receptor than the wild-type hGH. Its potency is also greater than that of wild-type hGH by about 12%.

Further, the variant pPRL (97–104) has essentially the same binding constant as wild-type hGH but about a 2.7-fold increase in potency.

EXAMPLE 12

Active Domains in hGH for Prolactin Receptor Binding

Human growth hormone (hGH) elicits a myriad of physiological effects including linear growth, lactation, nitrogen retention, diabetogenic and insulin-like effects, and macrophage activation. R. K. Chawla, J. S. Parks and D. Rudman, Annu. Rev. Med. 34, 519–547 (1983); O. G. P. Isaksson, et al. (1985) *Annu. Rev. Physiol.* 47, 483–499; C. K. Edwards, et al., (1988) *Science* 239, 769–771. Each of these effects begins with the interaction of hGH with specific cellular receptors. J. P. Hughs, et al. (1985) *Annu, Rev. Physiol.* 47, 469–482. Thus far, the only cloned genes whose products bind hGH are the hGH receptor from liver (D. W. Leung, et al., (1987) *Nature* (London) 33, 537–543) and the human prolactin (hPRL) receptor from mammary gland (J. M .Boutin, et al., (1988) *Cell* 53, 69–77). Receptor "spill-over" of hGH onto the hPRL receptor has clinical precedence in cases where acromegalics, who produce high levels of hGH, develop a hyperprolactinemic syndrome despite having normal levels of hPRL (J. E. Fradkin, et al., (1989) *New Engl. J. Med.* 320, 640–644). However, other receptors exist that bind hGH, including the placental lactogen (PL) receptor (M. Freemark, et al., (1987) *Endocrinology* 120, 1865–1872). It previously was not known if the binding sites on hGH for these receptors are identical or which receptor (or combination of receptors) is responsible for which pharmacological effect. To begin to address these issues the hGH and hPRL receptor binding sites on hGH were mapped. The results obtained indicate that these receptor binding sites overlap but are not identical. This has allowed the rational design of receptor-specific variants of hGH.

The hGH and hPRL receptors both contain an extracellular hormone binding domains that share 32% sequence identity, single transmembrane domains, and cytoplasmic domains which differ widely in sequence and length. The extracellular binding domain of the hGH receptor has been expressed in *E. coli* and has identical binding properties to that found naturally as a soluble serum binding protein (S. A. Spencer, et al., (1988) *J. Biol. Chem.* 26, 7862–7867). Similarly, the extracellular domain of the hPRL receptor has been expressed in *E. coli* and purified. The hPRL receptor fragment extends from residues Gln1 to Thr211 and terminates just before the single transmembrane domain. It retains high binding affinity and specificity that is virtually identical to its full-length receptor. The gene encoding the hPRL receptor used in the experiments was kindly provided by Dr. P. A. Kelly, Laboratory of Molecular Endocrinology, McGill University, Montreal, Canada. This DNA sequence was obtained from a human mammary cDNA library and identified with a probe covering known conserved regions amongst cross-species members of the prolactin receptor family. See e.g., Davies, J. A., et al., (1989) *Mol. Endrocrinology* 3, 674–680; Edery, et al. (1989) *Proc. Natl. Acad. Sci. USA* 86 2112–2116; Jolicoeur, et al. (1989) *Mol. Endro-*

*cinology* 3, 895–900. These truncated and highly purified receptors are extremely useful reagents for rapid and accurate assessment of binding affinity for mutants of hGH.

Relationship Between hPRL and hGH Receptor Binding Sites.

To determine if the epitopes for the hGH and hPRL receptors overlapped we analyzed whether or not the hPRL receptor fragment could displace the hGH receptor fragment from hGH (results not shown). Indeed, the hPRL receptor fragment competed for the hGH receptor binding site with an apparent Kd of 1 nM. This is virtually the same affinity as that measured by direct binding of the hPRL receptor to hGH (results not shown).

Eleven of the segment-substituted hGH variants from Table III were used to localize the epitope on hGH for the hPRL receptor. The hGHΔ32–46 variant was also used in this experiment. The approach was similar to that used to determine the epitope on hGH for the hGH receptor as previously described, i.e. by the disruption in binding of variants of hGH except that the receptor was hPRLr rather than hGHs. The results for the above twelve segment-substituted hGH variants are summarized in Table XVIII.

TABLE XVIII

Binding of hGH variants produced by homolog-scanning mutagenesis to the extracellular domain of the hPRL receptor (hPRLr). Mutants are named according to the extremes of segments substituted from the various hGH homologs: pGH, hPL, or hPRL. The exact description of the mutations introduced is given by the series of single mutants separated by commas. The component single mutants are designated by the single letter code for the wild-type residue followed by its codon position in mature hGH and then the mutant residue. Mutants of hGH were produced and purified as previously described herein. Binding to hPRLr was measured essentially as described for the hGHr (Spencer, S. A. et.al. (1988) J. Biol. Chem. 263, 7862–7867) except that affinity purified rabbit polyclonal antibodies raised against the hPRLr were used to precipitate the hPRLr complex with GIBCO ™ brand BSA (crude) as carrier protein. Standard deviations in values of $K_D$ were typically at or below 20% of the reported value. The relative reduction in binding affinity ($K_D$ (mut)/$K_D$ (hGH)) for the hGHr was taken from Table III herein. The change in receptor preference was calculated from the ratios of the relative reductions in binding affinity for the hGHr to the hPRLr. WT = wild-type.

| Mutant Name | Mutations Introduced | hPRLr $K_D$ (nM) | hPRLr $\frac{K_D \text{(mut)}}{K_D \text{(hGH)}}$ | hGHr $\frac{K_D \text{(mut)}}{K_D \text{(hGH)}}$ | Change in receptor preference $\frac{\text{hGHr}}{\text{hPRLr}}$ |
|---|---|---|---|---|---|
| WT hGH | none | 2.3 | (1) | (1) | (1) |
| pGH (11–33) | D11A, M14V, H18Q, R19H, F25A, Q29K, E33R | 852 | 370 | 3.4 | 110 |
| pGH (48–52) | P48A, T50A, S51A, L52F | 2.0 | 0.9 | 2.8 | 0.32 |
| pGH (57–73) | S57T, T60A, S62T, N63G, R64K, E65D, T67A, K70R, N72D, L73V | 167 | 73 | 17 | 4.3 |
| hGH (Δ32–46) | Deletion of residues 32 to 46 | 14 | 6.1 | ND | |
| hPL (46–52) | Q46H, H47D, P48S, Q49E, L52F | 4.4 | 1.9 | 7.2 | 0.26 |
| hPL (56–64) | E56D, R64M | 4.1 | 1.8 | 30 | 0.06 |
| hPRL (12–19) | N12R, M14V, L15V, R16L, R19Y | 3.2 | 1.4 | 17 | 0.08 |
| hPRL (22–33) | Q22N, F25S, D26E, Q29S, E30Q, E33K | 168 | 73 | 0.85 | 85 |
| hPRL (54–74) | F54H, S55T, E56S, I58L, P59A, S62E, N63D, R64K, E66Q, T674, K70M, S71N, N72Q, L73K, E74D | 2.5 | 1.1 | 69 | 0.02 |
| hPRL (88–95) | E88G, Q91Y, F92H, R94T, S95E | 3.8 | 1.6 | 1.4 | 1.1 |
| hPRL (97–104) | F97R, A98G, N99M, S100Q, L101D, V102A, Y103P, G104E | 12.1 | 5.2 | 1.6 | 3.2 |

TABLE XVIII-continued

| | | | | | |
|---|---|---|---|---|---|
| hPRL (111–129) | Y111V, L113I, K115E, D116Q, E118K, E119R, G120L, Q122E, T123G, G126L, R127I, E129S | 2.6 | 1.1 | 1.5 | 0.73 |
| WT hPRL | none | 7.6 | 3.3 | >100,000 | — |

As can be seen, pGH (11–33) and pGH (57–73) cause large disruptions in hPRL receptor binding affinity, whereas pGH (48–52) has no effect. Unlike the hGH receptor, the hPRL receptor will bind hPRL and hPL but not pGH. As expected, virtually all of the substitutions tested from the binding-competent hormones, hPRL or hPL, did not disrupt binding. The only exception was hPRL (22–33), which caused a >70-fold reduction in binding affinity for the hPRL receptor. Thus, the hPRL receptor is very sensitive to mutations in hGH near the central portion of helix 1 and the loop between residues 57 and 73.

The homolog-scan data also suggest that the hPRL and hGH receptor epitopes are not identical because several segment-substituted variants cause huge changes in receptor binding preference (Table XVIII). For example, the disruption in binding caused by the pGH (11–33) or hPRL (22–33) are about 100-fold greater for the hPRL receptor than for the hGH receptor. In contrast, the hPL (56–64) and hPRL (54–74) have almost no effect on the hPRL receptor, whereas they weaken binding to the hGH receptor by factors of 17 and 69, respectively. These preferential binding effects (along with binding of monoclonal antibodies as previously discussed) further substantiate that reductions in receptor binding affinity are caused by local and not global structural changes in the mutants of hGH.

The specific side-chains in hGH that strongly modulate binding to the hPRL receptor were identified by alanine-scanning mutagenesis and homologous substitutions. The hGH variants shown in Table XIX were prepared. The hPRL substitutions, F25S and D26E, cause the largest reductions in binding affinity (21 and 4.5-fold, respectively) in helix 1. These residues project from the hydrophilic face of helix 1 (FIG. 25B) and are on the same side as other mutations in helix 1 (notably H18A and F10A) that have milder effects on binding.

Four residues in the loop region (54 to 68) known to affect binding of hGH receptor as well as two residues (Q49A and T50A) preceding this region that are nearby and do not affect hGH receptor binding were tested. The most disruptive mutants are I58A and R64A, which reduced binding affinity by 32 and 6-fold, respectively; the other four mutations have negligible effects.

The fact that helix 1 and the loop region (58–64) contain strong binding determinants for the hPRL receptors implicate helix 4 because this helix is wedged between these two structures (FIG. 25B). Indeed, alanine-scanning of the helix 4 region between a disulfide linked to C165 through V185 reveals strong binding determinants (Table XIX). The most disruptive mutations extend nearly four helical turns, from R167 to R178, and are located on the same hydrophilic face.

TABLE XIX

Binding of single mutants of hGH to hPRL or hGH receptor fragments (hPRLr or hGHr). Mutants of hGH were prepared and purified as previously described except for Q22N, F25S, D26E, Q29S and E33K, which were produced by site-directed mutagenesis (Cunningham, B. C. and Wells, J. A. (1989) Science 244, 1330–1335; Zoller, M. J. and Smith, M. (1982) Nucleic Acids Res. 10, 6487–6499). Receptor binding assays and mutant nomenclature are described in Table XVIII. Data for the reduction in binding affinity to the hGHr is taken from Table III. ND indicates not determined.

| | hPRLr | | hGHr | Change in receptor preference |
|---|---|---|---|---|
| Mutant | $K_D$ (nM) | $\frac{K_D \text{ (mut)}}{K_D \text{ (hGH)}}$ | $\frac{K_D \text{ (mut)}}{K_D \text{ (hGH)}}$ | $\frac{hGHr}{hPRLr}$ |
| WT hGH | 2.3 | (1) | (1) | (1) |
| P2A | 1.3 | 0.6 | 0.9 | 0.7 |
| T3A | 3.4 | 1.5 | 0.9 | 1.7 |
| P5A | 2.5 | 1.1 | 2.1 | 0.5 |
| L6A | 4.0 | 1.8 | 2.8 | 0.6 |
| S7A | 1.9 | 0.8 | 1.8 | 0.4 |
| F10A | 8.1 | 3.5 | 5.9 | 0.6 |
| N12A | 1.9 | 0.8 | 1.2 | 0.7 |
| M14A | 1.3 | 0.6 | 2.2 | 0.3 |
| L15A | 1.2 | 0.5 | 1.3 | 0.4 |
| H18A | 3.9 | 1.7 | 1.6 | 0.6 |
| R19A | 1.4 | 0.6 | 0.7 | 2.4 |
| Q22N | 2.1 | 0.9 | ND | — |
| F25S | 48 | 21 | ND | — |
| D26E | 10 | 4.5 | ND | — |
| Q29S | 3.2 | 1.4 | ND | — |
| E33K | 1.8 | 0.8 | ND | — |
| Q49A | 1.5 | 0.7 | ND | — |
| T50A | 1.9 | 0.8 | ND | — |
| F54A | 1.8 | 0.8 | 4.4 | 0.2 |
| I58A | 73 | 32 | 17 | 1.9 |
| R64A | 13 | 5.7 | 21 | 0.3 |
| Q68A | 3.1 | 1.2 | 5.2 | 0.3 |
| R167A | 7.4 | 3.2 | 0.75 | 4.3 |
| K168A | 58 | 25 | 1.1 | 23 |
| D171A | 3.6 | 1.6 | 7.1 | 0.2 |
| K172A | 143 | 62 | 14 | 4.4 |
| E174A | 59 | 26 | 0.22 | 120 |
| F176A | 129 | 56 | 16 | 3.5 |
| R178N | 2.4 | 1.0 | 8.5 | 0.1 |
| R178K | 6.7 | 2.9 | ND | — |
| I179M | 1.3 | 0.6 | 2.7 | 0.2 |
| V185A | 3.9 | 1.7 | 4.5 | 0.4 |

Functional contour maps were derived based upon the location of the mutations in hGH that disrupt binding to the hGH and hPRL receptors (FIG. 28). The maximal extent of the epitope for the hPRL receptor (FIG. 25B) is approximated by mutations having less than a two-fold reduction in binding affinity. By this criteria the epitope for the hPRL receptor is essentially confined to the front face of helix 1 from F10 to Q29, the loop from F54 to Q68, and the hydrophilic face helix 4 from R167 to R178. In contrast, the hGH receptor epitope (FIG. 25A) is comprised of residues in the amino terminal region through the front face of helix 1 from I4 through M14, the loop region from F54 through S71, and the hydrophilic face of helix 4 from D171 through V185. Although further mutagenic analysis will be necessary to fill in remaining gaps in the hPRL epitope, it is clear this epitope overlaps but is not identical to that for the hGH receptor. These data suggest that not all of the binding determinants for recognizing hGH are the same in the hGH and hPRL receptors despite them sharing 32% sequence identity in their extracellular binding domains.

Residues that cause large changes in receptor binding affinity may do so by indirect structural effects. However, it is believed that most of these disruptive effects are due to local effects because all of the single mutants tested retain full binding affinity to a panel of 8 hGH monoclonal antibodies and often lead to changes in receptor preference (see Table XIX and infra) and not uniform disruptions in receptor affinity.

Design of Receptor-specific Variants of hGH.

A number of the single hGH mutants cause enormous changes in receptor binding preference (Table XIX). The most notable is E174A, which causes a 4-fold strengthening in affinity for the hGH receptor while weakening binding to the hPRL receptor by more than 20-fold. This represents a 120-fold shift in receptor preference. Other mutations (notably R178N and I179M) cause hGH to preferentially bind to the hPRL receptor. Typically, the variants that cause the greatest changes in receptor specificity are located in the non-overlap regions of the two receptor epitopes.

It was reasoned that if the changes in receptor binding free energy were additive, it could be possible to design highly specific variants of hGH with only a few mutations. Indeed, when the two most hGH-receptor-selective single mutants (K168A and E174A) are combined, the double mutant exhibits a 2300-fold preference for binding to the hGH receptor (Table XX). As previously indicated, the preference for binding the hPRL receptor can be enhanced by nearly 20-fold by hPL (56–64), which contains only two mutations, E56D and R64M (Table XIII). These hGH variants (K168A, E174A or E56D, R64M) do not substantially reduce the affinity for the preferred receptor, hGH or hPRL, respectively. It is also possible to reduce binding to both receptors simultaneously.

TABLE XX

Binding of double mutants of hGH designed to discriminate between the hGH and hPRL receptors (hGHr and hPRLr). Mutants of hGH were prepared by site-directed mutagenesis, purified, and assayed for binding to the hGHr or hPRLr as described in Table XIII. Standard deviations in the determination of $K_D$ were at or below 20% of the reported value except where the $K_d$ is above 10 $\mu$M, in which case they were ± 100% of the reported value.

| Mutant | hPRLr $K_D$ (nM) | hPRLr $\frac{K_D (mut)}{K_D (hGH)}$ | hGHr $K_D$ (nM) | hGHr $\frac{K_D (mut)}{K_D (hGH)}$ | Change in receptor preference $\frac{hGHr}{hPRLr}$ |
|---|---|---|---|---|---|
| WThGH | 2.3 | (1) | 0.34 | (1) | (1) |
| K168A, E174A | 1950 | 590 | 0.09 | 0.26 | 2300 |
| R18N, I179M | ND | — | ND | — | — |
| K172A, F176A | ~40,000 | ~20,000 | 190 | 50 | ~40 |

For example, combining K172A and F176A, which individually cause large reductions in binding affinity to the hGH and hPRL receptors, produces much larger disruptions in affinity of 550—and 15,000-fold, respectively.

In all these instances the changes in the free energy of binding ($\Delta\Delta_{binding}$) are strikingly additive (Table XXI). Additive effects of mutations have been observed in enzyme-substrate interactions (P. J. Carter, et al. (1984) Cell 38, 835–840; J. A. Wells, et al., (1987) Proc. Natl. Acad. Sci. USA 84, 5167–5171), protease-protease inhibitor interactions (M. Laskowski, et al. in Protease Inhibitors: Medical and Biological Aspects, (1983), eds. N. Katunuma, Japan Sci. Soc. Press, Tokyo, pp. 55–68, and protein stability (D. Shortle, et al., (1986) Proteins 1, 81–89 (1986); M. H. Hecht, J. M. Sturtevant and R. T. Sauer. Proteins 1, 43–46) and, as disclosed in these references, are most commonly found when the mutant residues function independently and are in contact with each other. This suggests the residues paired in the multiple mutants of hGH function independently. Such additivity creates an extremely predictable situation for engineering variants of hGH with desirable receptor binding affinity and specificity.

TABLE XXI

Additive effects of mutations in hGH upon binding to the hGH or hPRL receptors (hGHr or hPRLr). The change in the free energy of binding ($\Delta\Delta G_{binding}$) for the variant relative to wild-type hGH was calculated from the reduction in binding affinity according to: $\Delta\Delta G_{binding} = RT \ln[K_D (mut)/K_D (hGH)]$. The values of ($K_D$ (mut)/$K_D$ (hGH) for the single-or multiple-mutant hormones were taken from Tables XIII–XX.

| | Change in binding free energy, $\Delta\Delta G_{binding}$ (kcal/mol) | |
|---|---|---|
| Mutation | hGH | hPRLr |
| K168A | +0.04 | +1.9 |
| E174A | −0.90 | +1.9 |
| K168A, E174A (expected) | −0.86 | +3.8 |
| (actual) | −0.80 | +3.8 |
| K172A | +2.5 | +1.6 |
| F176A | +2.4 | +1.6 |
| K172A, F176A (expected) | +4.9 | +3.2 |
| (actual) | +5.7 | +3.8 |
| Q22N | −0.06 | ND |
| F25S | +1.81 | ND |
| D26E | +0.89 | ND |
| Q29S | +0.20 | ND |
| E30Q | ND | ND |
| E33K | −0.13 | ND |
| hPRL 22–33 (expected) | +2.7 | — |
| (actual) | +2.6 | — |
| E56A | ND | +0.8 |
| R64M | ND | +1.8 |
| E56A, R64M (expected) | — | +2.6 |
| hPL (56–64) (actual) | — | +2.0 |

There are a number of other cases like hGH where two or more receptors or receptor subtypes are known to exist such as for the adrenergic receptors (for review see R. J. Lefkowitz and M. G. Caron (1988) J. Biol Chem. 263, 4993–4996), IGF-I receptors (M. A. Cascieri, et al., (1989) J. Biol. Chem. 264, 2199–2202), IL-2 receptors (R. J. Robb, et al. (1984) J. Exp. Med. 160, 1126–1146; R. J. Robb, et al. (1988) Proc. Natl. Acad. Sci. USA 85, 5654–5658) and ANP receptors (D. Lowe and D. Goeddel, unpublished results). In these situations it is difficult to link specific receptor function to a specific pharmacological effect. However, the use of receptor-specific hormone analogs can greatly simplify this task. For example, catecholamine analogs were used to characterize β-adrenergic receptor subtypes and link receptor function to physiologic responses (for review see R. J. Lefkowitz, et al. (1983) Annu. Rev. Biochem. 52, 159–186).

By analogy, the receptor-specific variants of hGH should provide a key tool for identifying other receptors for hGH, and for probing the role of the hGH and hPRL receptors in the complex pharmacology of hGH. This work represents a systematic approach to identifying receptor binding sites in hormones that permits rational design of receptor-specific variants.

EXAMPLE 13

Engineering Human Prolactin to Bind to Human Growth Hormone

Prolactin (PRL) is a member of a large family of homologous hormones that includes growth hormones (GH), placental lactogens (PL), and proliferins. Nicoll, C. S. et. al. (1986) *Endocrinol. Rev.* 7, 169–203. Collectively, this group of hormones regulates a vast array of physiological effects involved in growth, differentiation, electrolyte balance, and others. Chawla, R. K. et.al. (1983) *Ann. Rev. Med.* 34, 519–547: Isaksson, O. G. P. et.al. (1985) *Ann. Rev. Physiol.* 47, 483–499. These pharmacological effects begin with binding to specific cellular receptors. For instance, hPRL binds to the lactogenic but not somatogenic receptor and stimulates lactation but not bone growth; hGH can bind to both the lactogenic and somatogenic receptors and stimulates both lactation and bone growth. The molecular basis for the differences in receptor binding specificity is not understood.

Cloning and Expression of hPRL.

The cDNA for hPRL was cloned from a human pituitary cDNA library in λgt10 (Huynh, T. V., et al. (1985) in *DNA Cloning Techniques: A Practical Approach,* Vol. 1, D. M. Glover, ed. (Oxford IRL Press) pp. 49–78) by hybridization (Maniatis, T., et al., eds. (1982) *Molecular Cloning A Laboratory Manual* (Cold Spring Harbor Laboratory, Cold Spring Harbor, N.Y.)) with oligonucleotide probes corresponding to 5' and 3' extremes of the published DNA sequence (Cooke, N. E., et al. (1981) *J. Biol. Chem.* 256, 4007–4016). A near full-length cDNA clone was identified and the 720-bp BstII-HindIII fragment, extending from codon 12 to 55 bp past the stop codon, was subcloned into pUC118. The sequence was determined by the dideoxy method (Sanger, F., et al. (1977) *Proc. Natl. Acad. Sci. USA* 74, 5463–5467) and matched exactly that previously reported (Cooke, N. E., et al. (1981) *J. Biol. Chem.* 25, 4007–4016).

The intracellular expression vector, pBO760 (FIG. 26), was created in several steps by standard methods (Maniatis, T., et al., eds. (1982) *Molecular Cloning A Laboratory Manual* (Cold Spring Harbor Laboratory, Cold Spring Harbor, N.Y.)). The *E. coli* trp promoter derived from pHGH207-1 (deBoer, H. A., et al. (1982) in *Promoters Structure and Function,* eds. Rodriguez, R. L. & Chamberlin, M. J. (Praeger, New York) pp. 462–481) was used to transcribe the hPRL gene. The hPRL coding sequence consisted of a 47-bp XbaI-BstEII synthetic DNA cassette and the 720-bp BstEII-HindIII fragment derived from the hPRL cDNA. The synthetic DNA cassette had the sequence where the initiation codon is indicated by asterisks. The phage f1 origin, pBR322 replication origin, and the pBR322 β-lactamase gene were derived from pBO475 (Cunningham, B. C., et al. (1989) *Science* 243, 1330–1335).

*E. coli* cells (MM 294) containing pBO760 were grown at 370° C. for 4 hr (or early log phase; $A_{550}$=0.1 to 0.3) in 0.5-L shake flasks containing 100 ml of M9 Hycase media (Miller, J. H. (1972) *Experiments in Molecular Genetics* (Cold Spring Harbor Laboratory, Cold Spring Harbor, N.Y.)) plus 15 µg/ml carbenicillin. Indole acrylic acid was added (50 µg/ml final) to induce the trp promoter. Cells were grown an additional 6–8 hr and harvested by centrifugation. Cell fractionation experiments showed the hPRL was located almost exclusively in inclusion particles and represented 2–5% of the total cell protein as analyzed by SDS-PAGE (not shown).

Purification and Refolding of hPRL.

Inclusion particles containing hPRL were isolated essentially as described (Winkler, M. E., et al. (1986) *Biochemistry* 25, 4041–4045). Briefly, 50 g of wet cell paste was suspended in 0.25 liters, 10 mM, TRIS HCl Tris (hydroxymethyl)aminomethane hydrochloride (pH 8.0), 1 mm EDTA (TE buffer) and cells were lysed by vigorous sonication. Insoluble material was collected by centrifugation (10,000×g for 15 min) and resuspended in 25 ml of TE buffer. The suspension was layered on a 0.2-liter cushion of 50% glycerol, and centrifuged at 9,000×g for 25 min to pellet the hPRL inclusion particles. The hPRL from the inclusion particles (about 20% pure) was suspended in 5 ml of TE buffer.

The hPRL was refolded by solubilizing the inclusion particles in 156 ml of 8N GnHCl in TE buffer plus 0.3 g reduced glutathione (Sigma). After gentle stirring at room temperature for 30 min, the mixture was chilled to 0° C. and diluted with 844 ml of cold TE buffer plus 0.6 g oxidized glutathione. The solution was stirred slowly overnight at 4° C., and dialyzed with 4 liters of TE buffer that was changed three times over 24 hr. Insoluble material was removed by centrifugation (10,000×g for 20 min).

The refolded and solubilized hPRL was further purified by precipitation with $(NH_4)_2SO_4$ to 45% saturation and stirred 2.5 hr at room temperature. The precipitate was collected by centrifugation (12,000×g for 30 min) and redissolved in 5 ml of TE buffer. After 30 min at room temperature, the solution was clarified (10,000×g for 10 min) and filtered through a millipore filter (0.45 µm). The solution was dialyzed against 0.5 liters of TE buffer overnight at 4° C. The hPRL (85% pure) was finally purified to homogeneity (>95%) by FPLC using DEAE fast-flow matrix essentially as described for purifying hGH (Cunningham, B. C., et al. (1989) *Science* 243, 1330–1335).

Mutagenesis and Binding Properties of hGH and hPRL Variants.

Site-specific mutagenesis (Zoller, M. J., et al. (1982) *Nucleic Acids Res.* 10, 6487–6500) was carried out with the aid of a methylation repair deficient strain of *E. coli,* Mut L (Kramer, B., et al. (1984) *Cell* 38, 879–887). Additional enrichment for mutant clones was obtained by designing mutagenic oligonucleotides to either introduce or eliminate a nearby unique restriction site so that restriction-purification or restriction-selection (Wells, J. A., et al. (1986)

```
                    * * *
5'-CT-AGA-ATT-ATG-TTA-CCA-ATT-TGT-CCA-GGT-GGT-GCA-GCA-AGG-TGT-CAA
   3'-T-TAA-TAC-AAT-GGT-TAA-ACA-GGT-CCA-CCA-CGT-CGT-TCC-ACA-GTT-CAC-TG,
```

Phil. Trans. R. Soc. Lond. A 317, 415–423), respectively, could be applied to the first pool of plasmid DNA obtained after transformation of the in vitro-generated heteroduplex. All oligonucleotides were designed to have 12 bp of exact match 5' to the most upstream mismatch and 10 bp 3' to the most downstream mismatch. For mutagenesis of hGH, the previously described hGH synthetic gene contained multiple restriction sites and was cloned into the plasmid, pBO475. Variants of hGH were secreted into the periplasmic space of E. coli (Chang, C. N., et al. (1987) Gene 55, 189–196) and purified as previously described.

The $K_d$ of each analog was determined by competitive displacement of [$^{125}$I]hGH bound to the purified recombinant hGH binding protein as previously described herein and in Spencer, S. A., et al. (1988) J. Biol. Chem. 263, 7862–7867. The previously described hGH binding protein (containing residues 1 to 238 of the cloned human liver receptor) was secreted and purified from E. coli as described in Fuh, G., et al. (1989) (submitted). Displacement curves were generated in triplicate and the standard deviations in the $K_d$ values were generally at or below 20% of the reported values and did not exceed 50% of the reported value except when Kd values were greater than 10 μM.

The concentrations of hPRL and hPRL mutants were determined by $A_{280}$ using a calculated extinction coefficient of ±S(0.1%,280)=0.9 (Wetlaufer, D. B. (1962) Adv. in Prot. Chem. 17, 303–390). This was adjusted accordingly when variants contained mutations in aromatic residues. Concentration values determined by absorbance agreed to within 10% with those determined by laser densitometry of proteins run on SDS-PAGE and stained with Coomassie blue for hGH. Circular dichroic spectra were collected on an Aviv Cary 60 spectropolarimeter.

In order to probe which of the divergent residues in hPRL were most disruptive for binding to the hGH receptor (FIG. 27), a number of hPRL residues were first introduced into hGH (Table XXII).

TABLE XXII

Comparison of hPRL and alanine substitutions introduced into hGH

| hGH variant | $K_d$ (nM) | $\frac{K_d \text{ (mut)}}{K_d \text{ (hGH)}}$ |
|---|---|---|
| WT | 0.34 | (1) |
| I58L | 0.58 | 1.7 |
| I58A | 5.6 | 16 |
| R64K | 0.20 | 0.6 |
| R64A | 7.1 | 21 |
| F176Y | 2.9 | 8.6 |
| F176A | 5.4 | 16 |
| R178K | 1.7 | 5.1 |
| R178N | 2.9 | 8.5 |

Whereas single alanine substitutions in hGH at positions 58, 64, 176 and 178 strongly disrupted receptor binding, substitutions of hPRL residues into hGH at these positions had less of an effect. The largest effects for hPRL substitutions were in the helix 4 residues that included positions 176 and 178. These data suggested that residues in the helix 4 region of hPRL could best account for the lack of binding to the hGH receptor.

The recombinant hPRL retained native-like structural and functional properties. First, the near and far ultraviolet CD spectra (FIG. 28) are identical to published spectra of natural hPRL (Bewley, T. A. (1979) in Recent Progress in Hormone Research, vol. 35, pp. 155–213, Acad. Press, N.Y.). The far ultraviolet spectrum is similar to that of hGH, suggesting a similar 4-helix bundle structure, although important differences in the mean residue ellipticity at 208 and 224 nm have been noted (Id) These hormones differ markedly in the near ultraviolet CD spectra which reflects variation in number and microenvironment of the aromatic residues between hGH and hPRL. In other studies (not shown), the recombinant hPRL retained full immunological cross-reactivity in an hPRL ELISA, and was equipotent with hGH in causing rat lymphoma Nb2 cells to proliferate (Tanaka, T., et al. (1980) J. Clin. Endo. Metab. 51, 1058–1063). Upon reduction, the purified hPRL showed a pronounced retardation in mobility by SDS-PAGE (as seen for hGH) suggesting that disulfide bonds had formed (Pollitt, S., et al. (1983) J. Bacteriol. 153, 27–32). Amino-terminal sequence analysis showed that the intracellularly expressed hPRL retained the amino-terminal methionine; however, as with methionyl-hGH (Olson, K. C., et al. (1981) Nature (London) 29, 408–411), this does not apparently affect its structure or function.

Binding of hPRL to the hGH binding protein is reduced by more than $10^5$-fold compared to hGH (Table XXIII), which is below the detection limit of our binding assay.

TABLE XXIII

Engineering residues in hPRL to permit binding to the hGH binding protein[1]

| hPRL Variant | $K_d$ (nM)[2] | $\frac{K_d \text{ (mut)}}{K_d \text{ (hGH)}}$ |
|---|---|---|
| hPRL WT | >40,000 | >100,000 |
| A = H171DN175TY176F | 4,900 | 14,000 |
| B = A + K178R | 220 | 660 |
| B + hGH (184–188) | 260 | 740 |
| hGH (54–74) | 25,000 | 66,000 |
| B + hGH (54–74) | 2,000 | 5,800 |
| B + H54FS56E:L58I:E62S:D63N:Q66E | 36 | 110 |
| B + H54F:S56E:L58I | 670 | 2,000 |
| C = B + E174A | 68 | 200 |
| D = C + E62S:D63N:Q66E | 2.1 | 6.2 |
| D + H54F | 4.4 | 13 |
| D + S56E | 2.5 | 7.4 |
| D + L58I | 3.6 | 11 |
| D + A59P | 2.5 | 7.4 |
| D + N71S | 3.6 | 11 |
| D + L179I | 2.1 | 6.2 |

[1]Mutants of hPRL were generated, purified and analyzed as described. Multiple mutants are indicated by a series of single mutants (Table XXII) separated by colons. Codon numbering is based upon the hGH sequence (FIG. 2).
[2]Average standard errors are at or below 20% of the reported values, except in cases where the $K_d$ exceeds 1 μM, where errors can be as large as 50%, and errors are much larger still when $K_d$ exceeds 10 μM.

A combination of three divergent residues in helix 4 from hGH (H171D, N175T, and Y176F) were introduced into hPRl. Alanine-scanning mutagenesis and hPRL substitutions (Table XXII) had shown that these residues were very important for binding hGH to the hGH receptor. This triple mutant of hPRL exhibited detectable binding to the hGH binding protein albeit 14,000-fold weaker than hGH. Installation of another important helix 4 residue (K178R) to produce a tetramutant (called variant B in Table XIII) further strengthened binding to a level now only 660-fold below wild-type hGH. Additional incorporation of hGH residues 184 to 188 into hPRL variant B did not enhance binding to the hGH binding protein. However, introduction of E174A to give hPRL variant C (Table XXIII) caused an additional 3.5-fold increase in binding affinity to the hGH binding protein as was found when E174A was incorporated into hGH.

Having engineered binding with the helix 4 region, the loop region containing residues 54 to 74 was analysed.

Complete replacement of the loop region in hPRL with the sequence from hGH (hGH (54–74) in Table XIII) gave barely detectable binding to the hGH binding protein. When this mutant was combined with variant B, the binding affinity increased substantially. However, this new variant [B plus hGH (54–74)] was reduced in binding affinity by almost 10-fold from variant B alone. Thus, it appeared that some of the hGH residues in the 54–74 loop were not compatible with the hGH substitutions in helix 4. We then selected from the 54 to 74 loop of hGH only those seven residues that were shown by alanine-scanning mutagenesis to most greatly influence binding. Although the R64A mutation in hGH caused more than a 20-fold reduction in binding affinity, the R64K variant of hGH (which is an hPRL substitution) slightly enhanced binding to the hGH binding protein (Table XXII). The Lys64 in hPRL therefore was left unchanged. As a consequence, only six of the seven substitutions from hGH were incorporated into hPRL that were most disruptive when changed to alanine in hGH. This new mutant (B plus H65F:S56E:L58I:E56S:D68N:Q66E) binds fifty-fold stronger than B plus hGH (54–74) and was only 110-fold reduced in binding affinity from wild-type hGH (Table XXIII). However, this represented only a modest improvement (six-fold) over variant B alone, which was less than expected for strongly favorable interactions previously observed in the loop region for hGH. Therefore, the six mutations within the loop were further dissected and revealed that the combination of H54F:S56E:L58I plus variant B bound three-fold weaker than variant B alone. Finally, incorporating the mutations E62S:D63N:Q66E into variant C (to give variant D) produced an analog with highest affinity that was only 6-fold reduced in binding affinity relative to hGH. Additional single mutations (H54F, S56E, L58I, A59P, N71S and L179I) did not enhance the binding affinity of hPRL variant D to the hGH binding protein. The conformation of variant D was virtually indistinguishable from that of native hPRL by CD spectral analysis (FIG. 28) or by ELISA reactivity (not shown).

Figure 27:
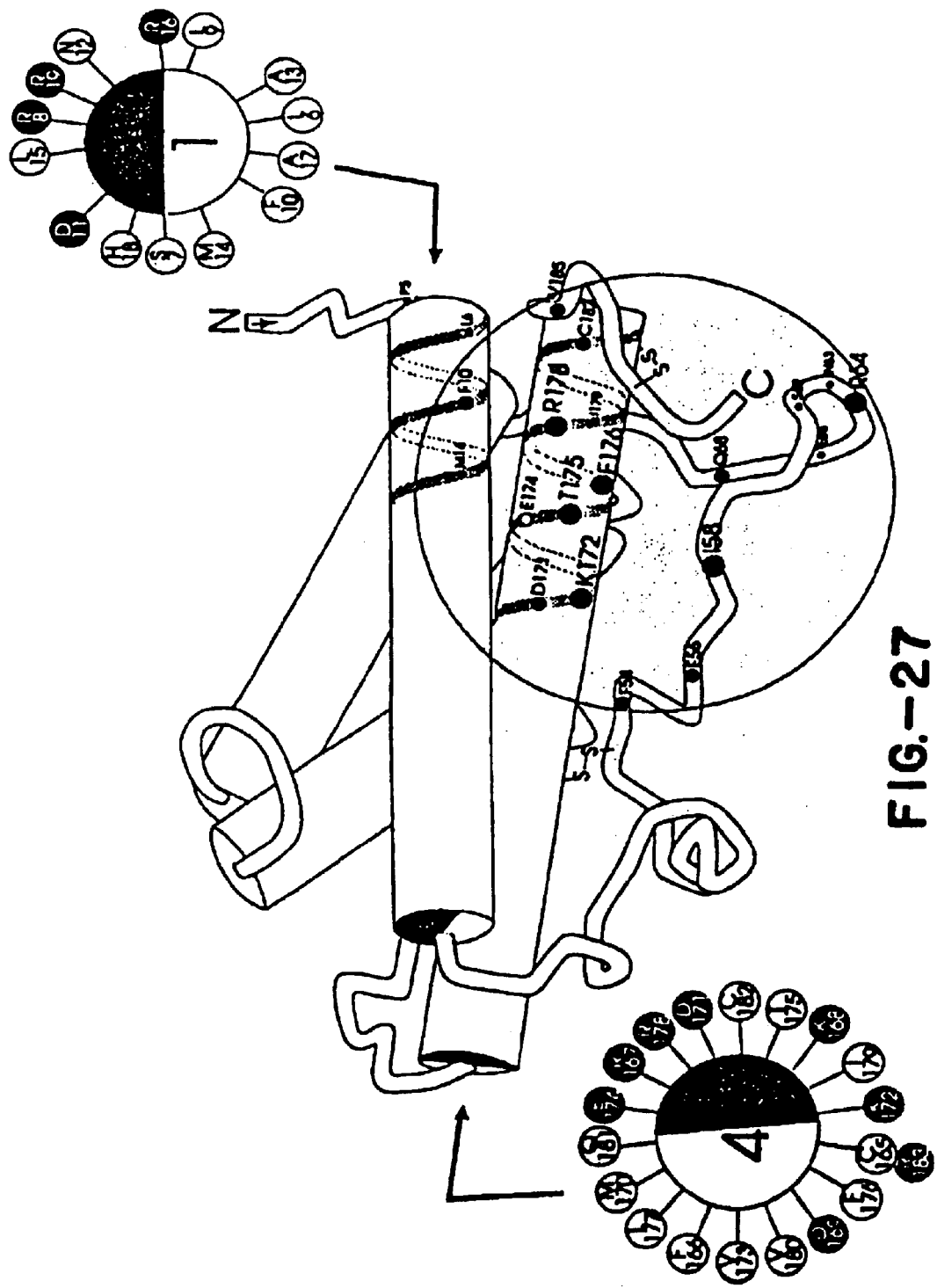
FIG. 27. Location of residues in hGH that strongly modulate its binding to the hGH binding protein. Alanine substitutions (serine or asparagine in the case of T175 or R178, respectively) are indicated that cause more than a 10-fold reduction (○), a 4- to 10-fold reduction (■), or more than a 4-fold increase (▲) in binding affinity. Helical wheel projections in regions of α-helix reveal their amphipathic quality and the fact that in helix 4 the most important determinants are on its hydrophilic face (shaded).

These studies demonstrate the feasibility of recruiting binding properties for distantly related homologs using only functional information derived from site-directed mutagenesis experiments. Alanine-scanning mutagenesis of hGH provided a systematic analysis of side-chains that were important for modulating binding of hGH to its receptor (FIG. 27).

Figure 29:
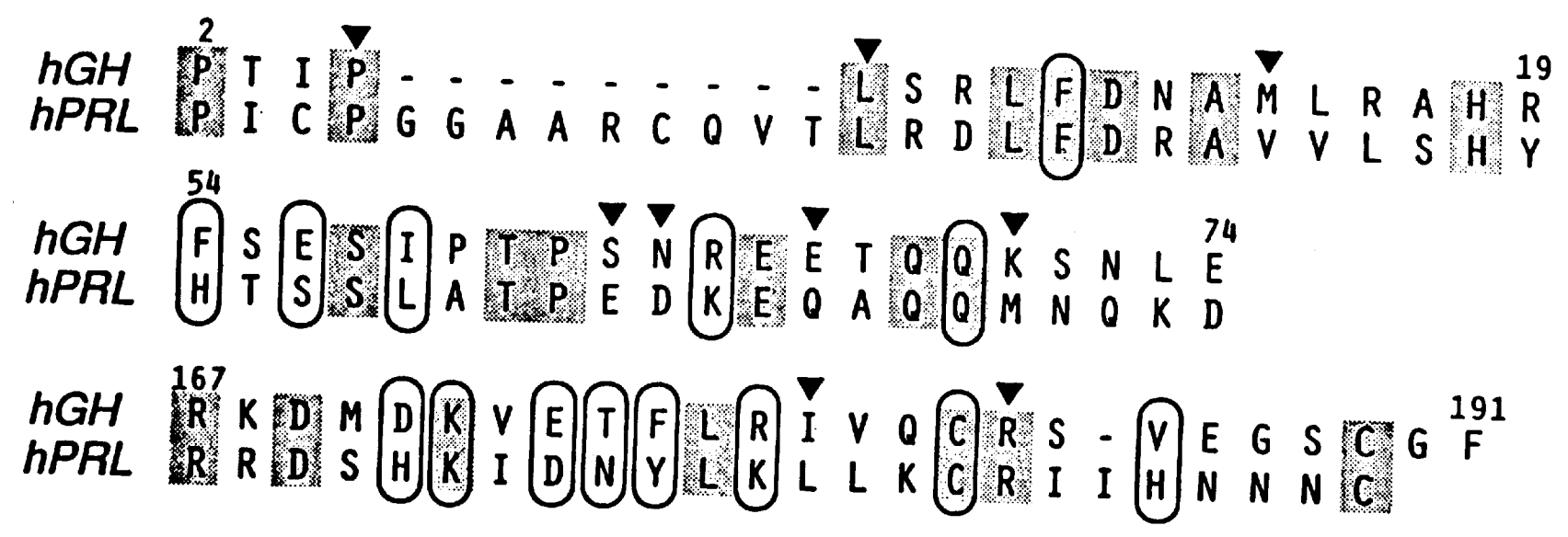

This information highlighted a number of residues in hPRL that could account for its inability to bind to the hGH receptor (FIG. 29). However, further analysis showed that the alanine substitutions in hGH were more disruptive than the hPRL substitutions in hGH (Table XXII). Furthermore, some of the hPRL substitutions were considerably more disruptive than others for binding affinity, especially when a larger side-chain was present in hPRL. For example, the conservative (but larger) F176Y mutation in hGH caused an eight-fold reduction in binding affinity with the hGH receptor, whereas the smaller R64K substitution showed slightly enhanced binding affinity. Thus, the analysis of disruptive hPRL substitutions in hGH suggested the introduction of the cluster of divergent residues in helix 4 to initially achieve binding affinity for hPRL. This was very important because no binding to the hGH receptor with wild-type hPRL had been observed, and it was necessary to introduce several hGH substitutions simultaneously into hPRL in order to bring the binding affinity within the range of the assay used ($K_d \leq 50$ $\mu$M).

Readily detectable binding affinity was engineered into hPRL by incorporating functionally important residues into helix 4. However, engineering the loop region between 54–74 turned out to be more difficult. Installing the entire loop from hGH into hPRL produced less enhancement in binding than expected, and was disruptive to binding when combined with the optimized helix 4 variant B. Our data suggest that the 54–74 loop structure in hPRL is supported by other interactions in the protein. This problem was solved in stages. First, only those six loop residues from hGH that the alanine scan together with the hPRL substitutions in hGH had identified to be important were introduced into hPRL. Although this improved the situation, the combination of some of these hGH mutations (narrowed down to H54F, S56E, and L58I) were disruptive to hPRL. These data suggest that some of the residues in the loop are crucial for its structure and are better off being left alone.

A number of iterative cycles of mutagenesis were necessary to converge upon a combination of residues that permitted tight binding of hPRL to the hGH receptor. This strategy relies on the assumption that the mutational effects will be somewhat additive as was, in fact, observed. For example, the E174A mutation enhanced the binding three to five-fold when added to either hPRL variant C or hGH. Moreover, the product of the disruptive effects of the H54F, S56E, and L58I single mutants to variant D (4.4-fold) is about the same as the disruption caused by the combination of all three mutations added to variant B (3-fold).

Even though variant D is only six-fold reduced in binding affinity, there are several other residues that could be incorporated into variant D to try to improve further on the binding, such as V14M and H185V; these are sites where alanine substitutions in hGH cause two to five-fold reductions in binding of hGH (FIG. 29). Although a high resolution structure would have aided in the design process, it was clearly not essential. The cumulative nature of the mutational effects allows one to converge upon the binding property in much the same way as proteins evolve, by cycles of natural variation and selection.

Previous protein engineering experiments have shown it is possible using highs resolution structural analysis to virtually exchange the substrate specificity of natural variant enzymes by site-directed mutagenesis of substrate contact residues (Wells, J. A., et al. (1987) *Proc. Natl. Acad. Sci. USA* 84, 5167–5171; Wilks, H. M., et al. (1988) *Science* 242, 1541–1544). Similarly, others have shown that binding properties can be engineered by replacement of entire regions of secondary structure units including antigen-binding loops (Jones, P. T., et al. (1986) *Nature* 321, 522–525) or DNA recognition helices (Wharton, R. P., et al. (1985) *Nature* 316, 601–605). However, to recruit the hGH receptor binding properties into hPRL required selective residue replacements within the structural scaffold of hPRL. Furthermore, the CD spectral data show that the overall structure of the hPRL variant D resembles more closely the structure of hPRL not hGH even though it attains binding properties like hGH.

The fact that the binding specificity for the hGH receptor could be incorporated into hPRL confirms the functional importance of particular residues for somatogenic receptor binding. These studies also provide compelling proof for structural relatedness between hGH and hPRL despite them having only 23% identity. This provides a rational approach to access new receptor binding functions contained within this hormone family starting with either a growth hormone, prolactin, proliferin or placental lactogen scaffold. Such hybrid molecules should be useful for distinguishing receptor binding and activation as well as the pharmacological importance of receptor subtypes. These analogs could lead to the design of new receptor-specific hormones having more useful properties as agonists or antagonists.

EXAMPLE 14

Recruitment of Binding Properties of Human Growth Hormone into Human Placental Lactogen Human placental lactogen (hPL) is reduced over thirty-fold in binding affinity compared to hGH for the hGH receptor (G. Baumann, et al., (1986) *J. Clin. Endocrinol, Metab.* 62, 134; A. C. Herington, et al. (1986) *J. Clin. Invest.* 77, 1817). Previous mutagenic studies showed the binding site on hGH for the hGH receptor is located primarily in two regions (including residues 54–74,) and 171–185), with some minor determinants near the amino terminus (residues 4–14).

The overall sequence of hPL is 85% identical to hGH. Within the three regions that broadly constitute the receptor binding epitope on hGH, hPL differs at only seven positions and contains the following substitutions: P2Q, I4V, N12H, R16Q, E56D, R64M, and I179M. (In this nomenclature the residue for wild-type hGH is given in single letter code, followed by its position in mature hGH and then the residue found in hPL; a similar nomenclature is used to describe mutants of hGH.) Single alanine substitutions have been produced in hGH at each of these seven positions. Of these, four of the alanine substitutions were found to cause two-fold or greater reductions in binding affinity, including I4A, E56A, R64A, and I179A. Generally, the alanine substitutions have a greater effect on binding than homologous substitutions from human prolactin. Therefore, the effect of some of the substitutions from hPL introduced into hGH were investigated. Whereas the I179A substitution caused a 2.7-fold reduction in affinity the I179M substitution caused only a slight 1.7-fold effect. However, the R64A and R64M substitutions caused identical and much larger reductions (about 20-fold) in binding affinity. Moreover, the double mutant (E56D:R64M) in hGH was even further reduced in affinity by a total of 30-fold (Table I). Thus, E56D and R64M primarily determine the differences in receptor binding affinity between hGH and hPL. The double mutant D56E, M64R in hPL therefore substantially enhances its binding affinity for the hGH receptor. Additional modifications such as M179I and V4I also enhance binding of hPL to the hGH receptor.

EXAMPLE 15

Effect of Amino Acid Replacement at Position 174 on Binding to the Human Growth Hormone As previously indicated, replacement of Glu174 with Ala (E174A) resulted in more than a 4-fold increase in the affinity of human growth hormone (hGH) for its receptor. To determine the optimal replacement residue at position 174 hGH variants substituted with twelve other residues were made and measured to determine their affinities with the hGH binding protein (Table XXIV). Side-chain size, not charge, is the major factor determining binding affinity. Alanine is the optimal replacement followed by Ser, Gly, Gln, Asn, Glu, His, Lys, Leu, and Tyr.

TABLE XXIV

| Mutant[a] | Side chain Charge | Side chain Size(Å$^3$)[b] | Kd (nM)[c] | Kd (mut) / Kd (wild type) |
|---|---|---|---|---|
| E174G | 0 | 9 | 0.15 | 0.43 |
| E174A | 0 | 26 | 0.075 | 0.22 |
| E174S | 0 | 33 | 0.11 | 0.30 |
| E174D | − | 59 | NE | — |
| E174N | 0 | 69 | 0.26 | 0.70 |
| E174V | 0 | 76 | 0.28 | 0.80 |
| wild-type | — | 89 | 0.37 | 1.0 |
| E174Q | 0 | 95 | 0.21 | 0.60 |
| E174H | 0 | 101 | 0.43 | 1.2 |
| E174L | 0 | 102 | 2.36 | 6.4 |
| E174K | + | 105 | 1.14 | 3.1 |
| E174R | + | 136 | NE | — |
| E174Y | 0 | 137 | 2.9 | 8.6 |

[a]Mutations were generated by site-directed mutagenesis (Carter, P., et al. (1986) Nucleic Acid Res. 13, 4431–4443) on a variant of the hGH gene thatcontains a KpnI site at position 178 cloned into pB0475. Oligonucleotides used for mutagenesis had the sequence: 5'-AC-AAG-CTC-NNN-ACA-TTC-CTG-CGC-ATC-GTG-CAG-T-3', where NNN represents the new codon at position 174 and asterisks indicate the mismatches to eliminate the KpnI site starting at codon 178. Mutant codons were as follows: Gln, CAG; Asn, AAC; Ser, AGC; Lys, AAA; Arg, AGG; His, CAC; Gly, GGG; Val, GTG; Leu, CTG. Following heteroduplex synthesis the plasmid pool was enriched for the mutation by restriction with KpnI to reduce the background of wild-type sequence. All mutant sequences were confirmed by dideoxy sequence analysis (Sanger, F., et al. (1977) Proc. Natl. Acad. Sci. USA 74, 5463–5467).
[b]Side-chain packing values are from C. Chothia (1984) Annu. Rev. Biochem. 53, 537.
[c]Dissociation constants were measured by competitive displacement of [$^{125}$I]hGH from the hGH binding protein as previously described. NE indicates that the mutant hormone was expressed at levels too low to be isolated and assayed.

EXAMPLE 16

The hGH variants shown in Table XXV were constructed. Their relativity potency as compared to wt-hGH are shown.

TABLE XXV

| hGH mutant | Relative potency in rat weight gain assay |
|---|---|
| F97A | 0.87 |
| S100A | 2.12 |
| L101A | 3.03 |
| V102A | 1.39 |
| Y103A | 1.73 |
| T175S | 1.21 |

Having described the preferred embodiments of the present invention, it will appear to those ordinarily skilled in the art that various modifications may be made to the disclosed embodiments, and that such modifications are intended to be within the scope of the present invention.

What is claimed is:
1. A DNA molecule comprising a nucleic acid sequence encoding a variant of a human growth hormone that binds to a target with an affinity different from the affinity of said human growth hormone for said target, wherein the amino acid sequence of said variant is not found in nature, and said variant comprises an amino acid substitution at an amino acid residue selected from the group consisting of P2, T3, P5, S7, L9, N12, L15, R16, R19, E30, E33, S43, F44, Q46, N47, P48, Q49, T50, F54, S55, E56, S57, I58, P59, S62, N63, F66, Q68, K70, S71, L73, R77, L80, F97, A98, N99, S100, L101, V102, Y103, G104, D169, T175, R178, Q181, C182, R183, S184, V185, E186, G187, S188, and F191, numbered from the N-terminus of 191-amino acid human growth hormone, wherein said variant is not hGH-V.

2. The DNA molecule of claim 1, wherein said amino acid residue is selected from the group consisting of F97, S100, L101, V102, Y103, and T175, numbered from the N-terminus of 191-amino acid human growth hormone.

3. An expression vector comprising the DNA molecule of claim 2.

4. An expression host comprising an expression vector including the DNA molecule of claim 2.

5. An expression vector comprising the DNA molecule of claim 1.

6. An expression host comprising an expression vector including the DNA molecule of claim 1.

7. A method of producing a growth hormone variant comprising culturing the expression host of claim 6 and recovering said growth hormone variant from the culture.

8. The DNA molecule of claim 1 further comprising an amino acid substitution at amino acid residue G120.

9. The DNA molecule of claim 1, wherein the variant comprises an amino acid substitution at an amino acid residue selected from the group consisting of P2, N12, L15, R16, and R19.

10. The DNA molecule of claim 1, wherein the variant comprises an amino acid substitution at an amino acid residue selected from the group consisting of T3, P5, S7, and L9.

11. The DNA molecule of claim 1, wherein the variant comprises amino acid substitution at an amino acid residue selected from the group consisting of E30, E33, S43, F44, and Q46.

12. The DNA molecule of claim 1, wherein the variant comprises an amino acid substitution at an amino acid residue selected from the group consisting of N47, P48, Q49, T50, and F54.

13. The DNA molecule of claim 1, wherein the variant comprises an amino acid substitution at an amino acid residue selected from the group consisting of S55, E56, S57, I58, and P59.

14. The DNA molecule of claim 1, wherein the variant comprises an amino acid substitution at an amino acid residue selected from the group consisting of S62, N63, E66, Q68, and K70.

15. The DNA molecule of claim 1, wherein the variant comprises an amino acid substitution at an amino acid residue selected from the group consisting of S71, L73, R77, L80, and F97.

16. The DNA molecule of claim 1, wherein the variant comprises an amino acid substitution at an amino acid residue selected from the group consisting of A98, N99, S100, L101, and V102.

17. The DNA molecule of claim 1, wherein the variant comprises an amino acid substitution at an amino acid residue selected from the group consisting of Y103, G104, D169, T175, and R178.

18. The DNA molecule of claim 1, wherein the variant comprises an amino acid substitution at an amino acid residue selected from the group consisting of Q181, C182, R183, S184, and V185.

19. The DNA molecule of claim 1, wherein the variant comprises an amino acid substitution at an amino acid residue selected from the group consisting of E186, G187, S188, and F191.

20. A DNA molecule comprising a nucleic acid sequence encoding a variant of human growth hormone that binds to a target with an affinity different from the affinity of said human growth hormone for said target, wherein the amino acid sequence of said variant is not found in nature, and said variant consists of a set of amino acid substitutions selected from the group consisting of;

N12H: F25L;

D11A: M14V: H18Q: R19H: F25A: Q29K: E33R;

N12R: M14V: L15V: R16L: R19Y: F25S: D26E: Q29S: E30Q: E33K;

N12R: M14V: L15V: R16L: R19Y;

Q22N: F25S: D26E: Q29S: E30Q: E33K;

Q46H: N47D: P48S: Q49E; L52F;

P48A: T50A: S51A: L52F;

E56D: R64M;

S57T: T60A: S62T: N63G: R64K: E65D: T67A: K70R; N72D: L73V;

F54H: S55T: F56S: I58L: P59A: S62E: N63D: R64K: E66Q: T67A: K70M: S71N: N72Q: L73K: E74D;

E88G: Q91Y: F92H: R94T: S59E;

F97R: A98G: N99M: S100Q: L101D: V102A: Y103P: G104 E;

N109D: V110D: D112H;

Y111V: L131I: K115E: D116Q: E118K: E119R: G120L: Q122E: T123G: G126L: R127I: E129S;

R127D: L128V: E129H: D130P: G131E: S132T: P133K: R134E: T135N; and

R167K: D171H: T179V: Q181K, numbered from the N-terminus of 191-amino acid human growth hormone.

21. An expression vector comprising the DNA molecule of claim 20.

22. An expression host comprising an expression vector including the DNA molecule of claim 20.

23. A variant of a human growth hormone that binds to a target with an affinity different from the affinity of said human growth hormone for said target, wherein the amino acid sequence of said variant is not found in nature, and said variant consists of a set of amino acid substitutions selected from the group consisting of:

N12H: F25L;

D11A: M14V: H18Q: R19H: F25A: Q29K: E33R;

N12R: M14V: L15V: R16L: R19Y: F25S: D26E: Q29S: E30Q: E33K;

N12R: M14V: L15V: R16L: R19Y;

Q22N: F25S: D26E: Q29S: E30Q: E33K;

Q46H: N47D: P48S: Q49E: L52F;

P48A: T50A: S51A: L52F;

E56D: R64M;

S57T: T60A: S62T: N63G: R64K: E65D: T67A: K70R: N72D: L73V;

F54H: S55T: E56S: I58L: P59A: S62E: N63D: R64K: E66Q: T67A: K70M: S71N: N72Q: L73K: E74D;

E88G: Q91Y: F92H: R94T: S95E;

F97R: A98G: N99M: S100Q: L101D: V102A: Y103P: G104E;

N109D: V110D: D112H;

Y111V: L113I: K115E: D116Q: E118K: E119R: G120L: Q122E: T123G: G126L: R127I: E129S;

R127D: L128V: E129H: D130P: G131E: S132T: P133K: R134E: T135N; and

R167K: D171H: I179V: Q181K, numbered from the N-terminus of 191-amino acid human growth hormone.

24. A variant of a human growth hormone that binds to a target with an affinity different from the affinity of said human growth hormone for said target, wherein the amino acid sequence of said variant is not found in nature, and said variant comprises an amino acid substitution at an amino acid residue selected from the group consisting of P2, T3, P5, S7, L9, N12, L15, R16, R19, E30, E33, S43, F44, Q46, N47, P48, Q49, T50, F54, S55, E56, S57, I58, P59, S62, N63, E66, Q68, K70, S71, L73, R77, L80, F97, A98, N99, S100, L101, V102, Y103, G104, D169, T175, R178, Q181, C182, R183, S184, V185, E186, G187, S188, and F191, numbered from the N-terminus of 191-amino acid human growth hormone, wherein said variant is not hGH-V.

25. The human growth hormone variant of claim 24 wherein said amino acid residue is selected from the group consisting of P2, F54, E56, I58, Q68, Q69, L73, T175, R178, C182, S184, V185, E186, S188, and F191, numbered from the N-terminus of 191-amino acid human growth hormone.

26. The human growth hormone variant of claim 25 wherein said amino acid substitution is selected from the group consisting of P2A, F54G, F54E, F54M, F54A, F54R, F54Q, F54S, F54Y, F54W, F54L, F54I, F54V, E56G, E56M, E56F, E56A, E56R, E56Q, E56S, E56D, E56N, E56K, E56L, E56H, I58G, I58E, I58M, I58F, I58A, I58R, I58Q, I58S, I58V, I58T, Q68G, Q68E, Q68M, Q68F, Q68A, Q68R, Q68S, Q68H, Q68K, Q68D, Q68N, Q69A, L73A, T175G, T175E, T175M, T175F, T175R, T175Q, T175S, T175V, T175I, R178G, R178E, R178M, R178F, R178A, R178S, R178H, R178K, R178D, R178N, C182G, C182E, C182M, C182F, C182A, C182R, C182Q, C182S, S184A, V185G, V185E, V185M, V185F, V185A, V185R, V185Q, V185S, V815I, V185T, V185L, V185Y, V815W, E186A, S188A, and F191A.

27. The human growth hormone variant of claim 24 wherein said amino acid residue is selected from the group consisting of N12, L15, R16, R19, S55, S57, P59, S62, N63, E66, K70, S71, C182, R183, and G187, numbered from the N-terminus of 191-amino acid human growth hormone.

28. The human growth hormone variant of claim 24 wherein said amino acid residue is selected from the group consisting of P2, Q69, L73, S184, E186, S188, and F191, numbered from the N-terminus of 191 amino acid human growth hormone.

29. The human growth hormone variant of claim 24 wherein said amino acid residue is selected from the group consisting of L73, E186, S188, and F191, numbered from the N-terminus of 191-amino acid human growth hormone.

30. The human growth hormone variant of claim 29 wherein said amino acid substitution is selected from the group consisting of L73A, E186A, S188A, and F191A.

31. The human growth hormone variant of claim 24 wherein said no acid residue is selected from the group consisting of Q46, N47, P48, Q49, T50, S51, K72, and V173, numbered from the N-terminus of 191-amino acid human growth hormone.

32. The human growth hormone variant of claim 31 wherein said amino acid substitution is selected from the group consisting of N47A and S51A.

33. The human growth hormone variant of claim 24 wherein said amino acid residue is selected from the group consisting of R19, E30, E33, S43, F44, L73, F97, A98, N99, S100, L101, V102, Y103, G104, E186, S188, and F191, numbered from the N-terminus of 191-amino acid human growth hormone.

34. The human growth hormone variant of claim 33 wherein said amino acid residue is selected from the group consisting of F97, A98, N99, S100, L101, V102, Y103, and G104, numbered from the N-terminus of 191-amino acid human growth hormone.

35. The human growth hormone variant of claim 34 wherein said amino acid substitution is selected from the group consisting of F97G, F97E, F97M, F97A, F97R, F97Q, F97S, F97Y, F97W, F97L, F97I, F97V, A98G, A98E, A98M, A98F, A98R, A98Q, A98S, A98D, A98N, A98H, A98K, N99G, N99E, N99M, N99F, N99A, N99R, N99Q, N99S, N99D, N99K, N99Y, S100G, S100E, S100M, S100F, S100A, S100R, S100Q, S100H, S100D, S100N, S100K, S100Y, L101G, L101E, L101M, L101F, L101A, L101R, L101Q, L101S, L101I, L101V, L101Y, V102G, V102E, V102M, V102F, V102A, V102R, V102Q, V102S, V102I, V102T, V102L, V102Y, V102W, Y103G, Y103E, Y103M, Y103F, Y103A, Y103R, Y103Q, Y103S, Y103W, Y103L, Y103I, Y103V, G104E, G104M, G104F, G104A, G104R, G104Q, G104S, and G104P.

36. The human growth hormone variant of claim 24 wherein said amino acid residue is selected from the group consisting of E33, Q49, T50, I58, R167, and R178, numbered from the N-terminus of 191-amino acid human growth hormone.

37. The human growth hormone variant of claim 36 said amino acid substitution is selected from the group consisting of R178K and R178N.

38. The human growth hormone variant of claim 24 wherein said amino acid residue is selected from the group consisting of F97, S100, L101, V102, Y103, and T175, numbered from the N-terminus of 191-amino acid human growth hormone.

39. The human growth hormone variant of claim 38 wherein said amino acid substitution is selected from the group consisting of F97A, S100A, L101A, V102A, Y103A, and T175S.

40. The human growth hormone variant of claim 24 further comprising an amino acid substitution at amino acid residue G120.

41. The variant of claim 24, wherein the variant comprises an amino acid substitution at an amino acid residue selected from the group consisting of P2, N12, L15, R16, and R19.

42. The variant of claim 24, wherein the variant comprises an amino acid substitution at an amino acid residue selected from the group consisting of T3, P5, S7, and L9.

43. The variant of claim 24, wherein the variant comprises an amino acid substitution at an amino acid residue selected from the group consisting of E30, E33, S43, F44, and Q46.

44. The variant of claim 24, wherein the variant comprises an amino acid substitution at an amino acid residue selected from the group consisting of N47, P48, Q49, T50, and F54.

45. The variant of claim 24, wherein the variant comprises an amino acid substitution at an amino acid residue selected from the group consisting of S55, E56, S57, I58, and P59.

46. The variant of claim 24, wherein the variant comprises an amino acid substitution at an amino acid residue selected from the group consisting of S62, N63, E66, Q68, and K70.

47. The variant of claim 24, wherein the variant comprises an amino acid substitution at an amino acid residue selected from the group consisting of S71, L73, R77, L80, and F97.

48. The variant of claim 24, wherein the variant comprises an amino acid substitution at an amino acid residue selected from the group consisting of A98, N99, S100, L101, and V102.

49. The variant of claim 24, wherein the variant comprises an amino acid substitution at an amino acid residue selected from the group consisting of Y103, G104, D169, T175, and R178.

50. The variant of claim 24, wherein the variant comprises an amino acid substitution at an amino residue selected from the group consisting of Q181, C182, R183, S184, and V185.

51. The variant of claim 24, wherein the variant comprises an amino acid substitution at an amino acid residue selected from the group consisting of E186, G187, S188, and F191.

* * * * *